United States Patent
Kousteni

(10) Patent No.: US 10,350,216 B2
(45) Date of Patent: Jul. 16, 2019

(54) METHODS OF TREATING, PREVENTING AND DIAGNOSING LEUKEMIA AND OTHER BLOOD DISEASES AND DISORDERS

(71) Applicant: The Trustees of Columbia University in the City of New York, New York, NY (US)

(72) Inventor: Stavroula Kousteni, Glen Ridge, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/760,026

(22) PCT Filed: Jan. 13, 2014

(86) PCT No.: PCT/US2014/011295
§ 371 (c)(1),
(2) Date: Jul. 9, 2015

(87) PCT Pub. No.: WO2014/110506
PCT Pub. Date: Jul. 17, 2014

(65) Prior Publication Data
US 2015/0359799 A1 Dec. 17, 2015

Related U.S. Application Data

(60) Provisional application No. 61/752,047, filed on Jan. 14, 2013.

(51) Int. Cl.
| | | |
|---|---|---|
| *A61K 39/395* | (2006.01) |
| *C07K 16/18* | (2006.01) |
| *C07K 16/22* | (2006.01) |
| *A61K 31/55* | (2006.01) |
| *C07K 16/28* | (2006.01) |
| *A01K 67/027* | (2006.01) |
| *C07K 14/47* | (2006.01) |
| *C12Q 1/6886* | (2018.01) |
| *A61K 45/06* | (2006.01) |
| *G01N 33/574* | (2006.01) |
| *C07K 14/435* | (2006.01) |
| *C07K 14/475* | (2006.01) |
| *C07K 16/30* | (2006.01) |
| *A61K 39/00* | (2006.01) |

(52) U.S. Cl.
CPC .......... *A61K 31/55* (2013.01); *A01K 67/0276* (2013.01); *A61K 39/3955* (2013.01); *A61K 45/06* (2013.01); *C07K 14/4702* (2013.01); *C07K 16/18* (2013.01); *C07K 16/22* (2013.01); *C07K 16/28* (2013.01); *C07K 16/2896* (2013.01); *C12Q 1/6886* (2013.01); *G01N 33/57426* (2013.01); *A01K 2217/052* (2013.01); *A01K 2217/075* (2013.01); *A01K 2217/15* (2013.01); *A01K 2217/206* (2013.01); *A01K 2227/105* (2013.01); *A01K 2267/03* (2013.01); *A01K 2267/0331* (2013.01); *A61K 2039/505* (2013.01); *A61K 2039/804* (2018.08); *C07K 16/30* (2013.01); *C07K 16/3061* (2013.01); *C07K 2317/73* (2013.01); *C07K 2317/76* (2013.01); *C12Q 2600/156* (2013.01); *C12Q 2600/158* (2013.01); *G01N 2333/4703* (2013.01)

(58) Field of Classification Search
CPC .......... A61K 2039/505; A61K 39/3955; A61K 39/39558; A61K 39/39533; C07K 2317/76; C07K 2317/92; C07K 2317/73; C07K 2317/565; C07K 16/30; C07K 2317/56; C07K 16/18; C07K 16/22; C07K 16/00; C07K 16/24; C07K 2316/96; C07K 14/475; C07K 14/52
See application file for complete search history.

(56) References Cited

U.S. PATENT DOCUMENTS

| | | | |
|---|---|---|---|
| 2004/0005561 A1 | 1/2004 | Gaiger et al. | |
| 2005/0261477 A1* | 11/2005 | Champion | A61K 38/00 530/350 |
| 2007/0092519 A1 | 4/2007 | Nakamura et al. | |
| 2008/0058316 A1* | 3/2008 | Eberhart | A61K 31/38 514/221 |
| 2008/0317760 A1* | 12/2008 | Gurney | C07K 16/2896 424/158.1 |
| 2010/0196385 A1* | 8/2010 | Bedian | C07K 16/22 424/141.1 |

(Continued)

FOREIGN PATENT DOCUMENTS

WO WO 2013/016081 1/2013

OTHER PUBLICATIONS

Huang et al. Gene Therapy for leukemia and lymphoma. Molec Pathol Hematolymphoid Diseases vol. 4: 81-89, 2010.*

(Continued)

*Primary Examiner* — Bridget E Bunner
(74) *Attorney, Agent, or Firm* — Leason Ellis LLP

(57) ABSTRACT

The present invention relates to preventing and treating leukemia and diseases and disorders of the blood, by inhibiting canonical Wnt signaling in the osteoblasts. The inhibition is accomplished by blocking specific molecules and receptors in the pathway. The present invention also relates to a method of diagnosing leukemia and disorders of the blood, and methods and assay for drug screening and basic research.

4 Claims, 57 Drawing Sheets

(56) References Cited

U.S. PATENT DOCUMENTS

| | | | |
|---|---|---|---|
| 2011/0189097 A1 | 8/2011 | Agalliu et al. | |
| 2012/0301489 A1* | 11/2012 | Gurney | A61K 39/3955 424/174.1 |
| 2013/0309246 A1* | 11/2013 | Kang | C12Q 1/6886 424/158.1 |
| 2014/0010810 A1* | 1/2014 | West | C07K 16/18 424/134.1 |
| 2015/0232568 A1* | 8/2015 | Siebel | C07K 16/28 424/139.1 |

OTHER PUBLICATIONS

Juengst, E.T. What next for human gene therapy? BMJ 326: 1410-1411, 2003.*

Phillips, A.J. The challenge of gene therapy and DNA delivery. J Pharmacy Pharmacol 53: 1169-1174, 2001.*

Rubanyi, G.M. The future of human gene therapy. Mol Aspects Med 22: 113-142, 2001.*

Bhatia et al. Innovative approaches for enhancing cancer gene therapy. Discovery Med 15(84): 309-317, 2013.*

Funahashi et al. A Notch1 ectodomain construct inhibits endothelial Notch signaling, tumor growth, and angiogenesis. Cancer Res 68(12): 4727-4735, 2008.*

Kamdje et al. Role of stromal cell-mediated Notch signaling in CLL resistance to chemotherapy. Blood Cancer J 2: e73, 2012; 10 total pages.*

Li et al. Notch signaling maintains proliferation and survival of the HL60 promyelocytic leukemia cell line and promotes the phosphorylation of the Rb protein. Mol Cell Biochem 340: 7-14, 2010.*

Rosati et al. Constitutively activated Notch signaling is involved in survival and apoptosis resistance of B-CLL cells. Blood 113: 856-865, 2009.*

Rosati et al. Gamma-secretase inhibitor I induces apoptosis in chronic lymphocytic cells by proteosome inhibition, endoplasmic reticulum stress increase and Notch down-regulation. Int J Cancer 132: 1940-1953, published online Sep. 24, 2012.*

Tohda et al. Expression of Notch1 and Jagged1 proteins in acute myeloid leukemia cells. Leukemia Lymphoma 42(3): 467-472, 2001.*

Varnum-Finney et al. Immobilization of Notch ligand, Delta-1, is required for induction of Notch signaling. J Cell Sci 113: 4313-4318, 2000.*

Xu et al. Activation of Notch signal pathway is associated with a poorer prognosis in acute myeloid leukemia. Med Oncol 28: S483-S489, 2011.*

Elyaman et al. Jagged1 and Delta1 differentially regulate the outcome of experimental autoimmune encephalomyelitis. J Immunol 179: 5990-5998, 2007.*

Galan-Diez et al. Targeting the endosteal niche in myelodysplasia and acute myeloid leukemia. J Bone Mineral Res 32 (Suppl 1): S63, #FR0038, 2017.*

Nakagawa et al. Targeting osteoblast in myelodysplasia and acute myeloid leukemia. Blood 126(23): 2551, 2015 (abstract).*

Shi et al. Human adipose tissue-derived mesenchymal stem cells facilitate the immunosuppressive effect of cyclosporin A on T lymphocytes through Jagged-1-mediated inhibition of NF-kB signaling. Exp Hematol 39: 214-224, 2011.*

Takam Kamga et al. Role of stromal cell-mediated Notch signaling in AML resistance to chemotherapy. Blood 124(21): 1044, 2014 (abstract).*

Zeuner et al. The Notch2-Jagged1 interaction mediated stem cell factor signaling in erythropoiesis. Cell Death Differentiation 2011(18): 371-380, 2011.*

Reya et al., "Wnt Signaling in Stem Cells and Cancer", Nature, vol. 434, Apr. 14, 2005, pp. 843-850.

Almeida et al., "Oxidative Stress Antagonizes Wnt Signaling in Osteoblast Precursors by Diverting—Catenin from T Cell Factor— to Forkhead Box O-mediated Transcription" Sep. 14, 2007, J Biol. Chem. 282:27298-27305.

Arai et al., "Tie2/Angiopoietin-1 Signaling Regulates Hematopoietic Stem Cell Quiescence in the Bone Marrow Niche", Jul. 23, 2004, Cell 118: 149-161.

Barrett et al., "NCBI GEO: mining millions of expression profiles-database and tools", (2005) Nucleic Acids Res. 33:D562-D566. Downloaded on Apr. 21, 2015.

Butler et al., "Endothelial Cells Are Essential for the Self-Renewal and Repopulation of Notch-Dependent Hematopoietic Stem Cells", Mar. 5, 2010, Cell Stem Cell 6:251-264.

Calvi et al., "Osteoblastic cells regulate the haematopoietic stem cell niche", Oct. 23, 2003, Nature 425:841-846.

Chan et al., "Endochondral ossification is required for haematopoietic stem-cell niche formation", Jan. 22, 2009, Nature 457:490-494.

Chen et al., "Runx1 is required for the endothelial to haematopoietic cell transition but not thereafter", Feb. 12, 2009, Nature 457:887-891.

Dacquin et al., "Mouse 1(I)-Collagen Promoter Is the Best Known Promoter to Drive Efficient Cre Recombinase Expression in Osteoblast", Published on May 6, 2002, Dev. Dyn. 224:245-54.

Day et al., "Wnt/ -Catenin Signaling in Mesenchymal Progenitors Controls Osteoblast and Chondrocyte Differentiation during Vertebrate Skeletogenesis", May 2005, Dev. Cell 8:739-750.

Delaney et al., "Notch-mediated expansion of human cord blood progenitor cells capable of rapid myeloid reconstitution", Feb. 2010, Nat. Med. 16:232-236.

Ding et al., "Clonal evolution in relapsed acute myeloid leukaemia revealed by whole-genome sequencing", Jan. 26, 2012, Nature 481:457-462.

Eghbali-Fatourechi et al., "Circulating Osteoblast-Lineage Cell," (2005) N. Engl. J Med. 352:1959-1966. Downloaded on Apr. 21, 2015.

Essers et al., "Functional Interaction Between β-Catenin and FOXO in Oxidative Stress Signaling", May 20, 2005, Science 308:1181-1184.

Estrach et al., "Jagged 1 is a -catenin target gene required for ectopic hair follicle formation in adult epidermis", Sep. 14, 2006, Development 133:4427-4438.

Flores-Figueroa et al., "Mesenchymal stem cells in myelodysplastic syndromes: phenotypic and cytogenetic characterization", (2005) Leuk. Res. 29:215-224. Accepted Jun. 22, 2004.

Ghosh-Choudhury et al., "Expression of the BMP 2 Gene during Bone Cell Differentitaion", (1994) Crit. Rev. Eukaryot. Gene Expr. 4:345-355.

Glass et al., "Canonical Wnt Signaling in Differentiated Osteoblasts Controls Osteoclast Differentiation", May 2005, Dev. Cell 8:751-764.

Gowen et al., "Cathepsin K Knockout Mice Develop Osteopetrosis Due to a Deficit in Matrix Degradation but Not Demineralization", Nov. 10, 1999, J. Bone Miner. Res. 14:1654-1663.

Graubert and Walter, "Genetics of Myelodysplastic Syndromes: New Insights", (2011) Hematology. Am. Soc. Hematol. Educ. Program. 2011:543-549.

Guangyu Wu et al., "SEL-10 Is an Inhibitor of Notch Signaling That Targets Notch for Ubiquitin-Mediated Protein Degradation", Nov. 2001, Mol. Cell. Biol. 21:7403-7415.

Harada et al., "Intestinal polyposis in mice with a dominant stable mutation of the $^2$-catenin gene", (1999) EMBO 18:5931-42.

Heissig et al., "Recruitment of Stem and Progenitor Cells from the Bone Marrow Niche Requires MMP-9 Mediated Release of Kit-Ligand", May 31, 2002, Cell 109:625-637.

Hill et al., "Canonical Wnt/ -Catenin Signaling Prevents Osteoblasts from Differentiating into Chondrocytes", May 2005, Dev. Cell 8:727-738.

Holmen et al., "Essential Role of -Catenin in Postnatal Bone Acquisition*", Mar. 31, 2005, J. Biol. Chem. 280:21162-68.

Hurlbut et al., "Crossing paths with Notch in the hyper-network", Feb. 20, 2007, Curr. Opin. Cell Biol. 19:166-175.

Hubbell et al., "Robust estimators for expression analysis", (2002) Bioinformatics 18:1585-1592. Downloaded on Apr. 22, 2015.

(56) References Cited

OTHER PUBLICATIONS

Iwamoto et al., "Mesenchymal cells regulate the response of acute lymphoblastic leukemia cells to asparaginase", Apr. 2007, J. Clin. Invest. 117:1049-1067.
Kiel and Morrison, "Uncertainty in the niches that maintain haematopoietic stem cells", Apr. 2008, Nat. Rev Immunol. 8:290-301.
Kiel et al., "SLAM Family Receptors Distinguish Hematopoietic Stem and Progenitor Cells and Reveal Endothelial Niches for Stem Cells", Jul. 1, 2005, Cell 121:1109-1121.
Kiernan et al., "The Notch Ligand JAG1 Is Required for Sensory Progenitor Development in the Mammalian Inner Ear", Jan. 13, 2006, PloS Genetics 2:e4.
Kim et al., "Defective Notch activation in microenvironment leads to myeloproliferative diseas", Sep. 25, 2008, Blood 112:4628-4638.
Klinakis et al., "A novel tumour-suppressor function for the Notch pathway in myeloid leukaemia", May 12, 2011, Nature 473:230-233.
Kogan et al., "Bethesda proposals for classification of nonlymphoid hematopoietic neoplasms in mice", Jul. 1, 2002, Blood 100:238-245.
Kornak et al., "Loss of the CIC-7 Chloride Channel Leads to Osteopetrosis in Mice and Man", Jan. 26, 2001, Cell 104:205-215.
Kuhnert et al., "Dll4-Notch signaling as a therapeutic target in tumor angiogenesis", (2011) Vascular Cell 3:20.
Li and Durbin, "Fast and accurate long-read alignment with Burrows-Wheeler transform", Jan. 15, 2010, Bioinformatics 26:589-595.
Lo et al., "Live-animal tracking of individual haematopoietic stem/progenitor cells in their niche", Jan. 1, 2009, Nature 457:92-96.
Lowell et al., "Deficiency of the Hck and Src Tyrosine Kinases Results in Extreme Levels of Extramedullary Hematopoiesis" Mar. 1, 1996, Blood 87:1780-1792.
Manavalan et al., "Circulating Osteogenic Precursor Cells in Type 2 Diabetes Mellitus", Jun. 27, 2012, J Clin. Endocrinol. Metab 97:3240-3250.
Mayack and Wagers, "Osteolineage niche cells initiate hematopoietic stem cell mobilization", May 2, 2008, Blood 112:519-531.
Mendez-Ferrer et al., "Mesenchymal and haematopoietic stem cells form a unique bone marrow niche", Aug. 12, 2010, Nature 466:829-834.
Mercher et al., "The OTT-MAL fusion oncogene activates RBPJ-mediated transcription and induces acute megakaryoblastic leukemia in a knockin mouse model", Apr. 2009, J Clin. Invest. 119:852-864.
Meyer et al., "New insights to the MLL recombinome of acute leukemias", Mar. 5, 2009, Leukemia 23:1490-1499.
Miyamoto et al., "Osteoclasts are dispensable for hematopoietic stem cell maintenance and mobilization", Sep. 22, 2011, J Exp. Med. 208:2175-2181.
Paik et al., "FoxOs Are Lineage-Restricted Redundant Tumor Suppressors and Regulate Endothelial Cell Homeostasis", Jan. 26, 2007, Cell 128:309-23.
Pajvani et al., Inhibition of Notch signaling ameliorates insulin resistance in a FoxO1-dependent manner, Aug. 2011, Nat. Med. 17:961-967.
Parfitt et al., "Bone Histomorphometry: Standardization of Nomenclature, Symbols, and Units," (1987) J. Bone Miner. Res. 2:595-610.
Raaijmakers et al., "Bone progenitor dysfunction induces myelodysplasia and secondary leukaemia", Apr. 8, 2010, Nature 464:852-857.
Rached et al., "FoxO1 expression in osteoblasts regulates glucose homeostasis through regulation of osteocalcin in mice", Jan. 2010, J. Clin. Invest. 120:357-68.
Rached et al., "FoxO1 Is a Positive Regulator of Bone Formation by Favoring Protein Synthesis and Resistance to Oxidative Stress in Osteoblasts", Feb. 3, 2010, Cell Metab. 11:147-160.
Rankin et al., "The HIF Signaling Pathway in Osteoblasts Directly Modulates Erythropoiesis through the Production of EPO", Mar. 30, 2012, Cell 149:63-74.
Raza and Galili, "The genetic basis of phenotypic heterogeneity in myelodysplastic syndromes", Dec. 2012, Nat. Rev. Cancer 12:849-859.
Real et al., "Y-secretase inhibitors reverse glucocorticoid resistance in T cell acute lymphoblastic leukemia", Jan. 2009, Nat. Med. 15:50-58.
Recker. et al., "Issues in modern bone histomorphometry", Jul. 23, 2011, Bone 49:955-964.
Robert-Moreno et al., "Impaired embryonic haematopoiesis yet normal arterial development in the absence of the Notch ligand Jagged1", Jun. 5, 2008, EMBO J 27:1886-1895.
Rodda and McMahon, "Distinct roles for Hedgehog and canonical Wnt signaling in specification, differentiation and maintenance of osteoblast progenitors", Jun. 7, 2006, Development 133:3231-3244.
Rubin et al., Parathyroid Hormone Stimulates Circulating Osteogenic Cells in Hypoparathyroidism, Jan. 2011, J Clin. Endocrinol. Metab 96:176-186.
Schaniel et al., "Wnt-inhibitory factor 1 dysregulation of the bone marrow niche exhausts hematopoietic stem cell", Sep. 1, 2011, Blood 118:2420-2429.
Shiozawa et al., Human prostate cancer metastases target the hematopoietic stem cell niche to establish footholds in mouse bone marrow, Apr. 2011, J Clin. Invest 121:1298-1312.
Simon et al., "Design and Analysis of DNA Microarray Investigations," Class Comparison in Design and Analysis of DNA Microarray Investigations (ed. K.Dietz,M.G.K.K.J.S.A.T.) 65-94 (Springer, New York, 2003).
Smyth (2004), "Linear Models and Empirical Bayes Methods for Assessing Differential Expression in Microarray Experiments", Stat. Appl. Genet. Mol. Biol 3, Article 3 (2004). Downloaded on Apr. 22, 2015.
Soriano et al., Targeted Disruption of the c-src Proto-Oncogene Leads to Osteoptrosis in Mice, Feb. 22, 1991, Cell 64:693-702.
Sternberg et al., "Evidence for reduced B-cell progenitors in early (low-risk) myelodysplastic syndrome", Aug. 2, 2005, Blood 106:2982-2991.
Sugiyama et al., "Maintenance of the Hematopoietic Stem Cell Pool by CXCL12-CXCR4 Chemokine Signaling in Bone Marrow Stromal Cell Nichesm", Dec. 2006, Immunity 25:977-988.
Sykes et al., "AKT/FOXO Signaling Enforces Reversible Differentiation Blockade in Myeloid Leukemias", Sep. 2, 2011, Cell 146:697-708.
Taichman and Emerson, "Human Osteoblasts Support Hematopoiesis through the Production of Granulocyte Colony-stimulating Factor," May 1994, J. Exp. Med. 179:1677-1682.
Taichman et al., "Human Osteoblasts Support Human Hematopoietic Progenitor Cells in In Vitro Bone Marrow Cultures", Jan. 15, 1996, Blood 87:518-524.
"Genomic and Epigenomic Landscapes of Adult De Novo Acute Myeloid Leukemia", The Cancer Genome Atlas Research Network Genomic and Epigenomic Landscapes of Adult De novo Acute Myeloid Leukemia May 30, 2013, N. Engl. J Med. 368:2059-2074.
Tiacci et al., "BRAF Mutations in Hairy-Cell Leukemia", Jun. 16, 2011, N. Engl. J Med. 364:2305-2315.
Van de Loosdrecht et al., "Identification of distinct prognostic subgroups in low- and intermediate-1-risk myelodysplastic syndromes by flow cytometry", Feb. 1, 2008, Blood 111:1067-1077.
Van Es et al., "Notch/γ-secretase inhibition turns proliferative cells in intestinal crypts and adenomas into goblet cells", Jun. 16, 2005, Nature 435:959.
Visnjic et al., "Hematopoiesis is severely altered in mice with an induced osteoblast deficiency", Jan. 15, 2004, Blood 103:3258-3264.
Walkley et al., "Rb Regulates Interactions between Hematopoietic Stem Cells and Their Bone Marrow Microenvironment", Jun. 15, 2007, Cell 129:1097-1110.
Wei et al., "A critical role for phosphatase haplodeficiency in the selective suppression of deletion 5q MDS by lenalidomid", Apr. 6, 2009, Proc. Natl. Acad. Sci. U S A 106:12974-12979.
Winkler et al., "Anti-inflammatory activity of IgG1 mediated by Fc galactosylation and association of FcγRIIB and dectin-1", Sep. 2012, Nat. Med. 18:1651-1657.

(56) References Cited

OTHER PUBLICATIONS

Wu et al., "Osteoblastic regulation of B lymphopoiesis is mediated by $G_s$-dependent signaling pathway", Sep. 12, 2008, Proc. Natl. Acad. Sci. U S A 105:16976-16981.
Zhang et al., "Identification of the haematopoietic stem cell niche and control of the niche size", Oct. 23, 2003, Nature 425:836-841.
Zhu et al., "Osteoblasts support B-lymphocyte commitment and differentiation from hematopoietic stem cells", Jan. 16, 2007, Blood 109:3706-3712.
Zuniga-Pflucker, "T-cell development made simple", Jan. 2004, Nat. Rev. Immunol. 4:67-72.

* cited by examiner

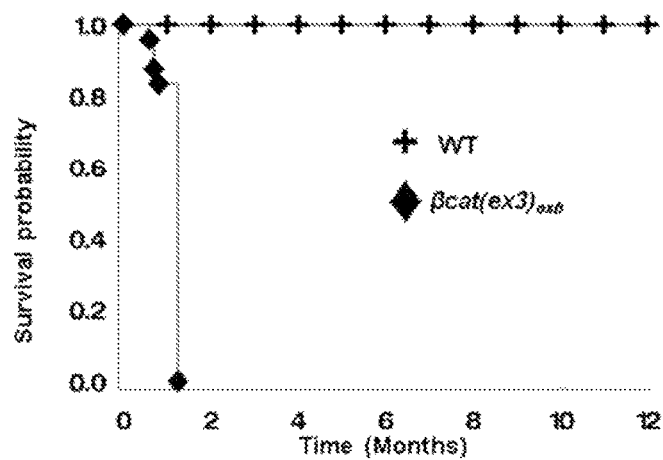
Fig. 1
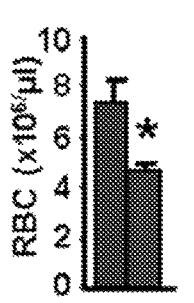 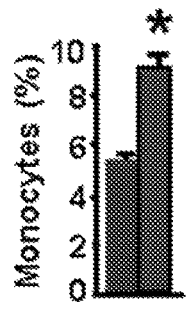 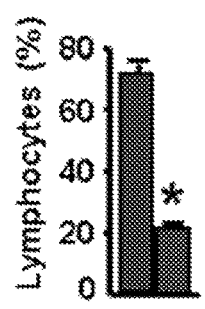 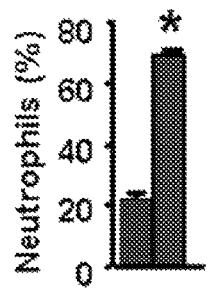
Fig. 2A     Fig. 2B     Fig. 2C     Fig. 2D

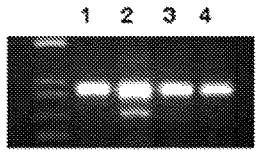
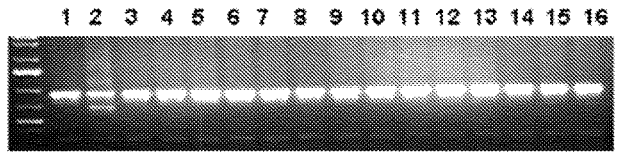

Fig. 8A

Lane 1: WT osteoblasts
Lane 2: βCat(ex3)osb osteoblasts
Lane 3: WT LSK+ve population
Lane 4: βCat(ex3)osb LSK+ve population

Fig. 8B

Lane 1: WT osteoblasts
Lane 2: βCat(ex3)osb osteoblasts
Lane 3: WT LT-HSC population
Lane 4: βCat(ex3)osb LT-HSC population
Lane 5: WT ST-HSC and MPP
Lane 6: βCat(ex3)osb ST-HSC and MPP
Lane 7: WT GMP population
Lane 8: βCat(ex3)osb GMP population
Lane 9: WT MEP population
Lane 10: βCat(ex3)osb MEP population
Lane 11: WT CMP population
Lane 12: βCat(ex3)osb CMP population
Lane 13: WT CLP population
Lane 14: βCat(ex3)osb CLP population
Lane 15: WT Ter119+ve population
Lane 16: βCat(ex3)osb Ter119+ve population

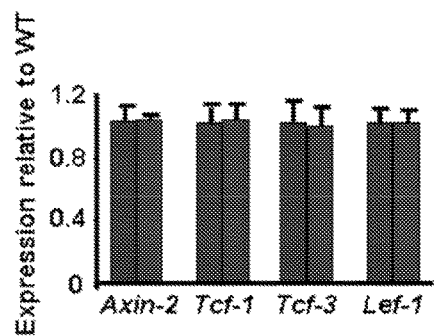

Fig. 9A

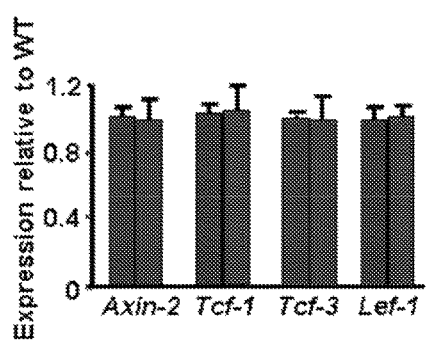

Fig. 9B

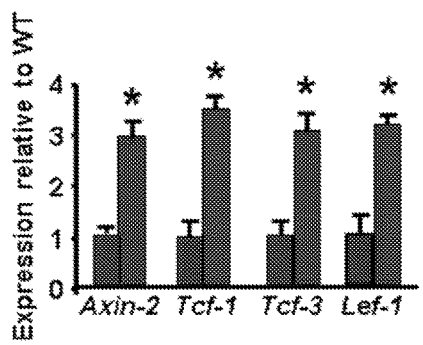

Fig. 9C

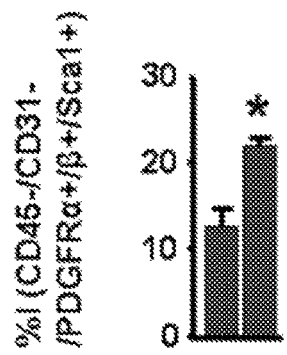
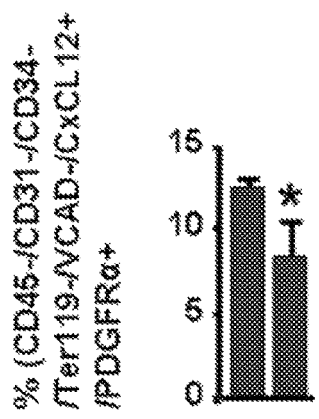
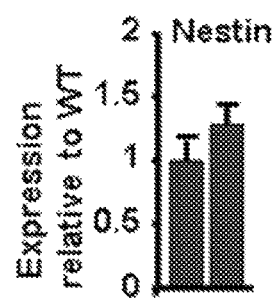
Fig. 16A    Fig. 16B    Fig. 16C
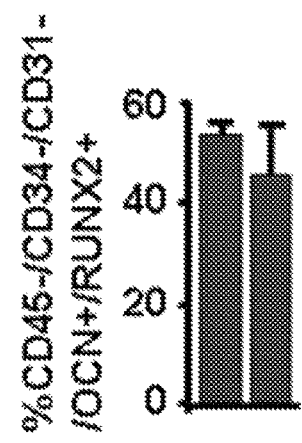
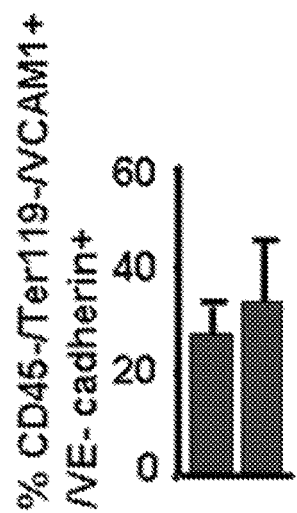
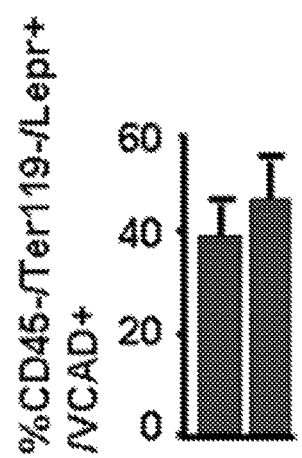
Fig. 16D    Fig. 16E    Fig. 16F

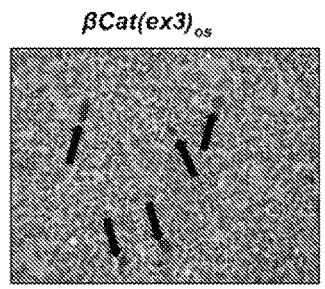
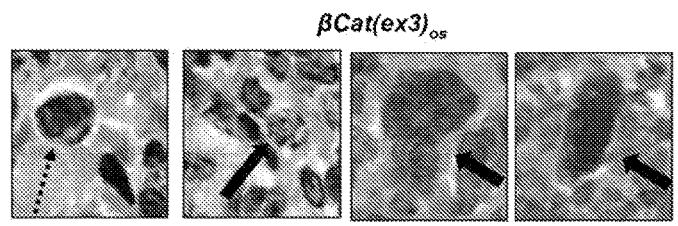
Fig. 17E          Fig. 17F
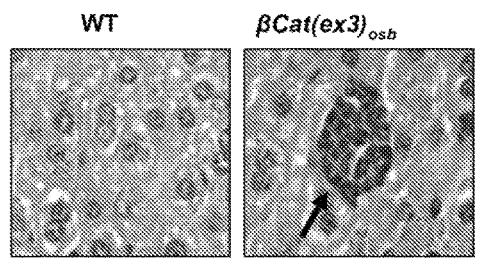
Fig. 17G
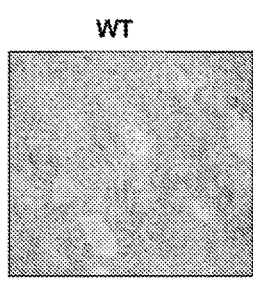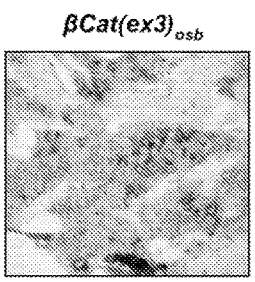  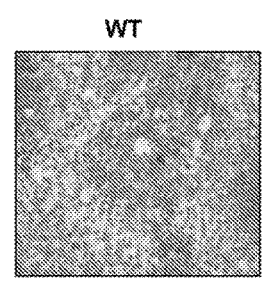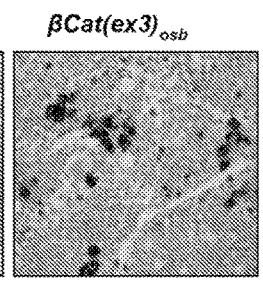
Fig. 18A                              Fig. 18B

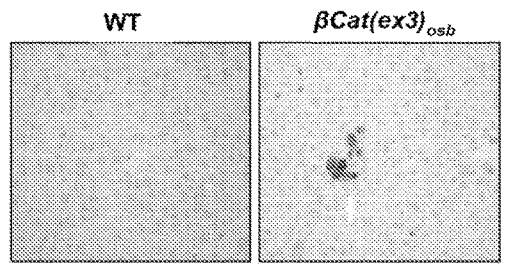
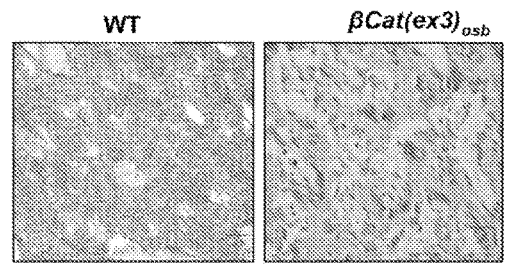
Fig. 18C                                    Fig. 18D
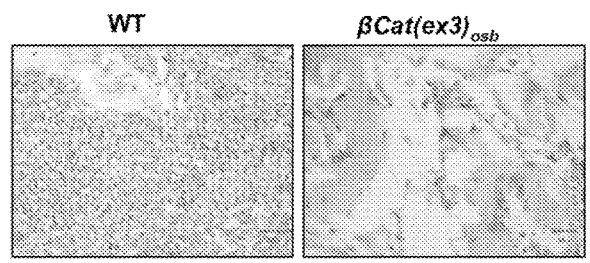
Fig. 18E
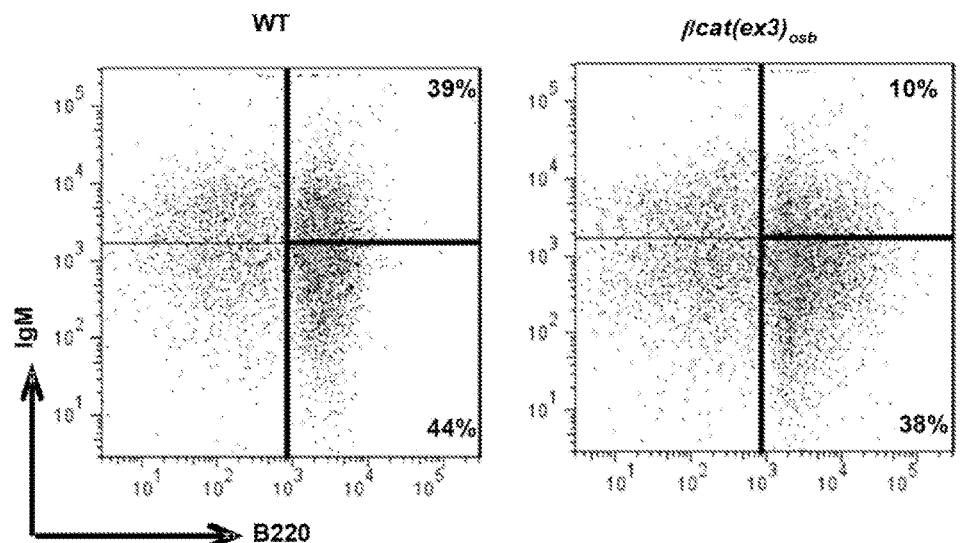
Fig. 19A

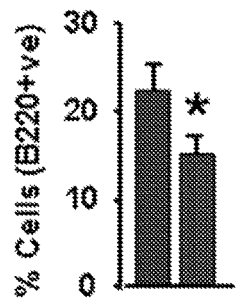
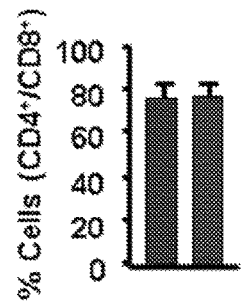
Fig. 21              Fig. 22B
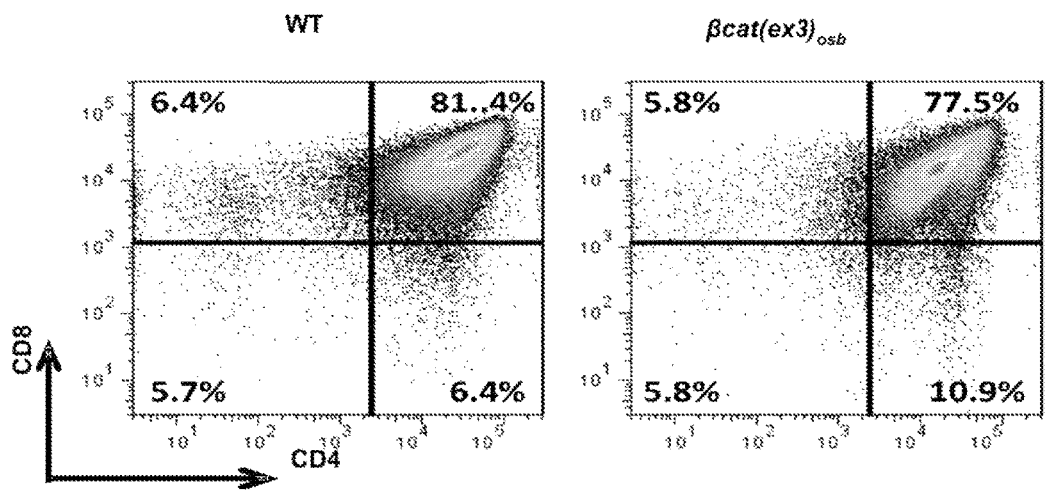
Fig. 22A
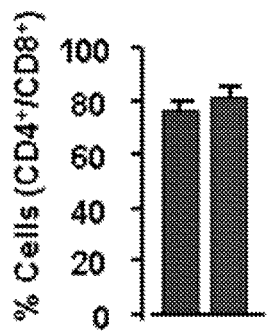
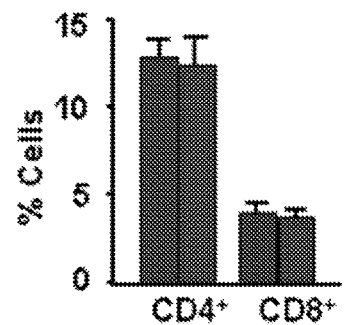
Fig. 23A              Fig. 23B

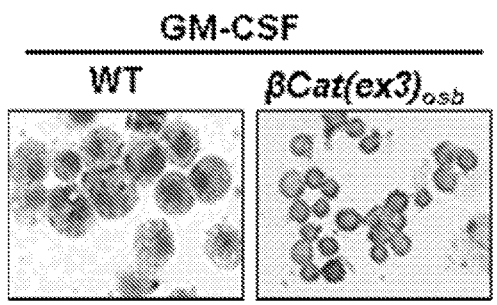
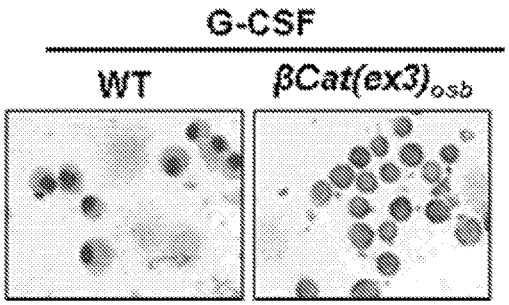
Fig. 25A  Fig. 25B
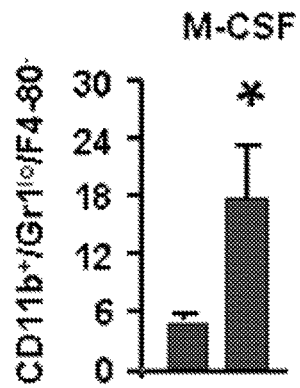
Fig. 26A
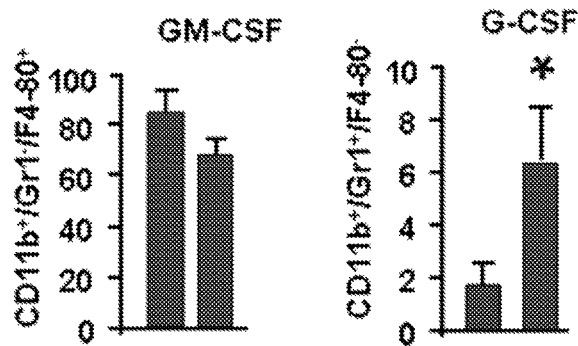
Fig. 26B  Fig. 26C

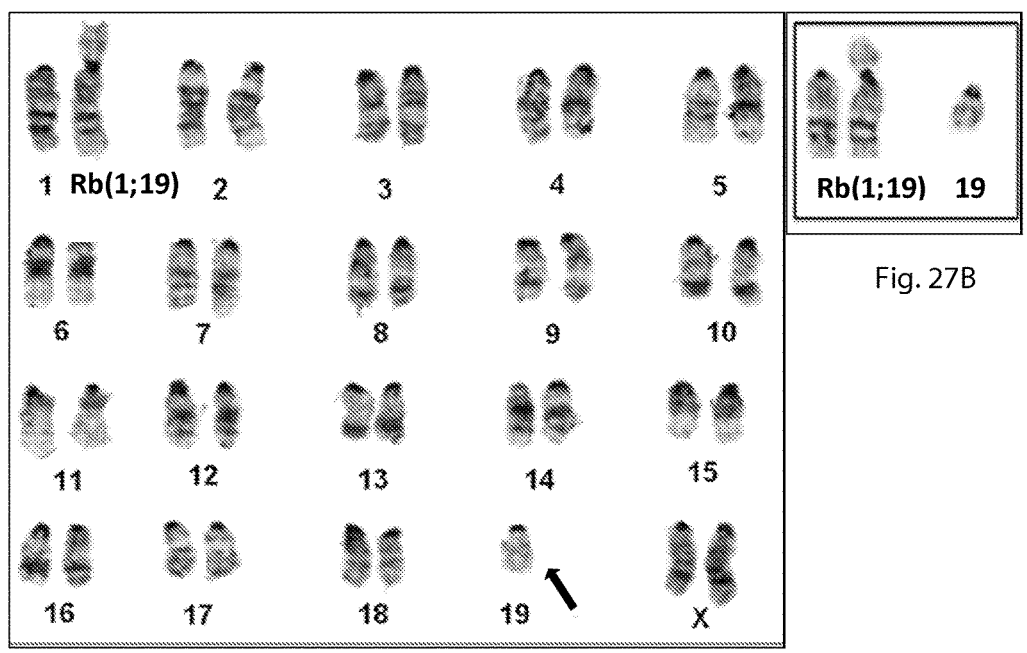
Fig. 27B
Fig. 27A
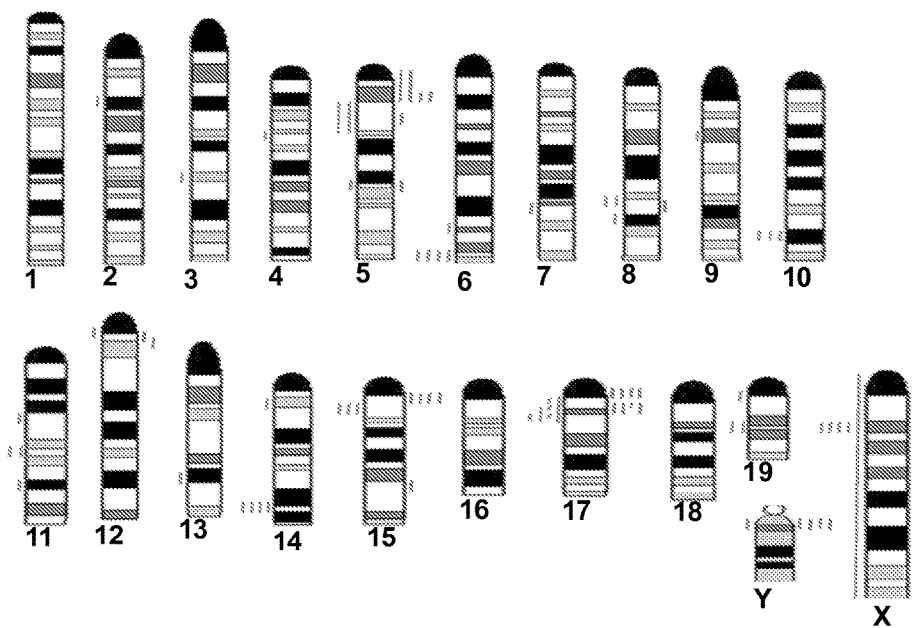
Fig. 28

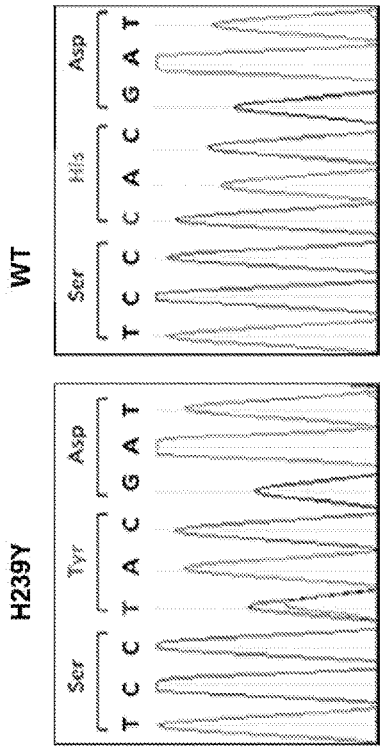
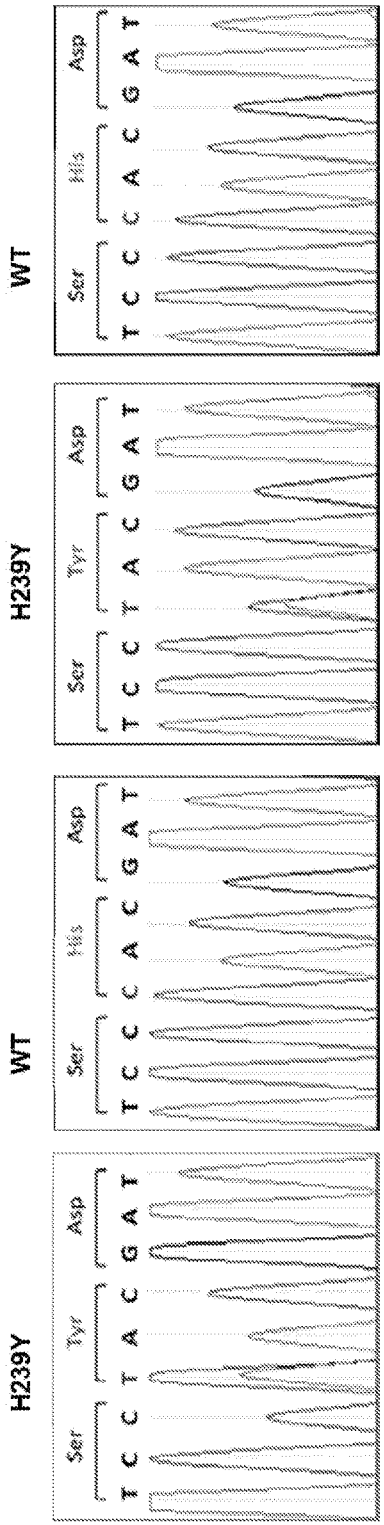
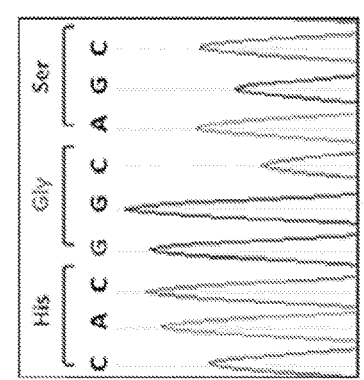
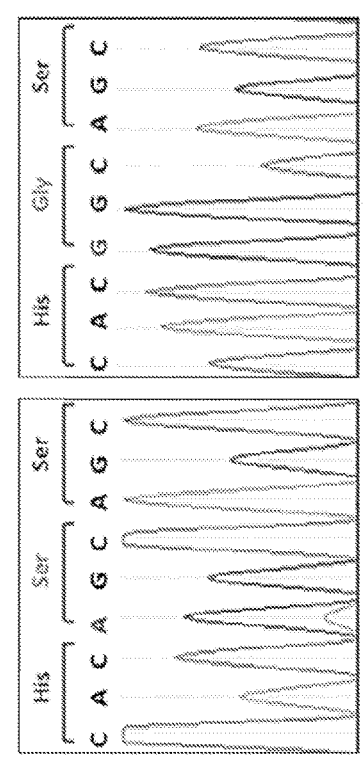
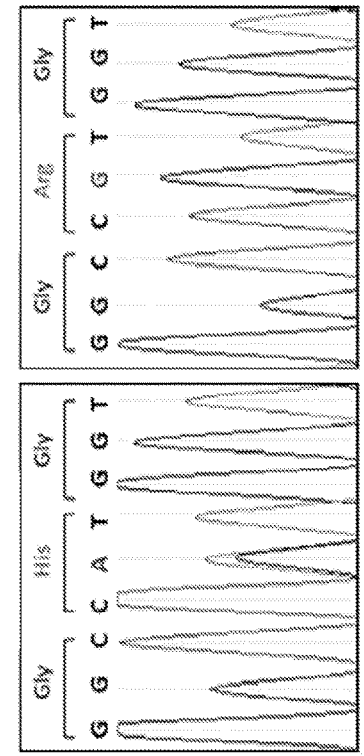
Fig. 29A
Fig. 29B
Fig. 29C
Fig. 29D

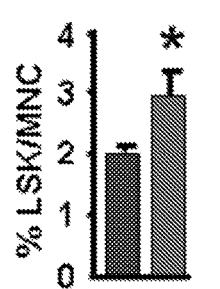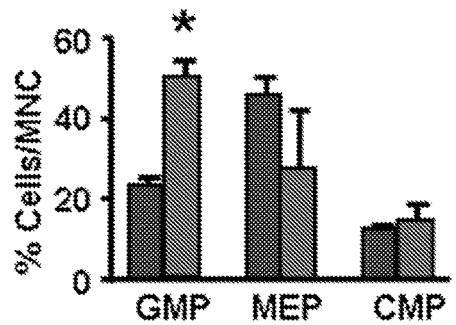
Fig. 30A    Fig. 30B
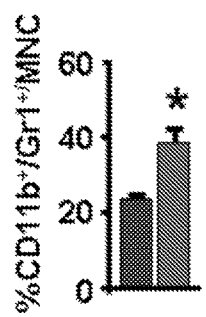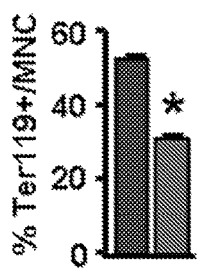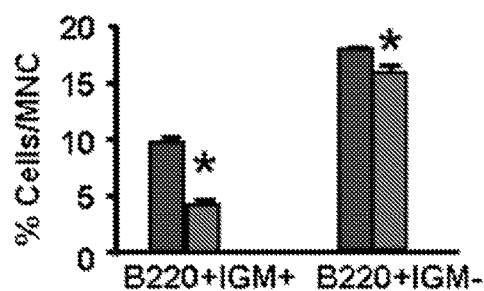
Fig. 30C    Fig. 30D    Fig. 30E
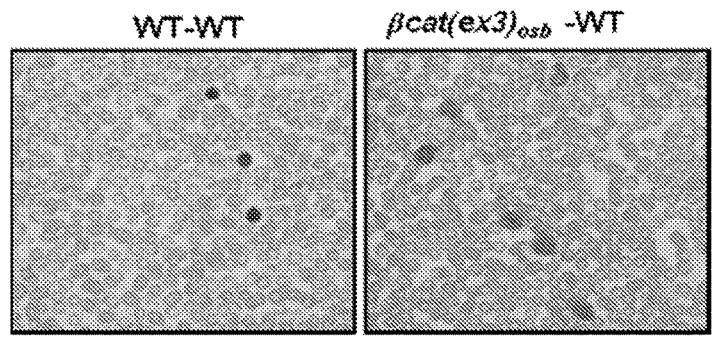
Fig. 31A    Fig. 31B

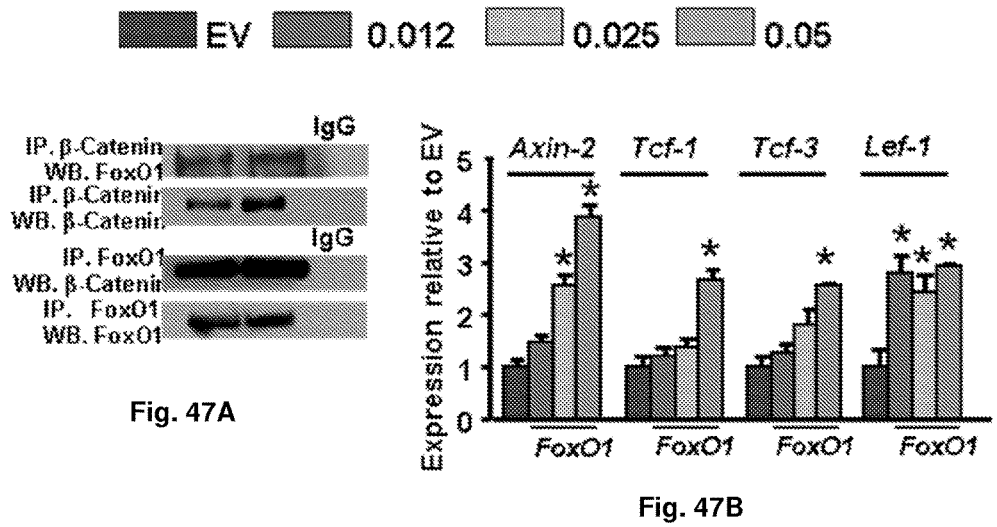
Fig. 47A
Fig. 47B
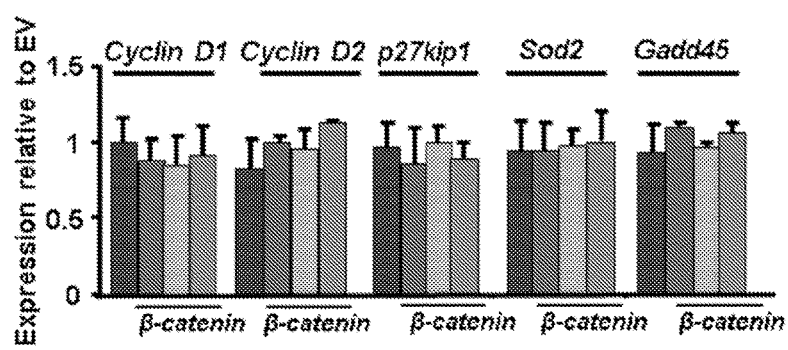
Fig. 47C
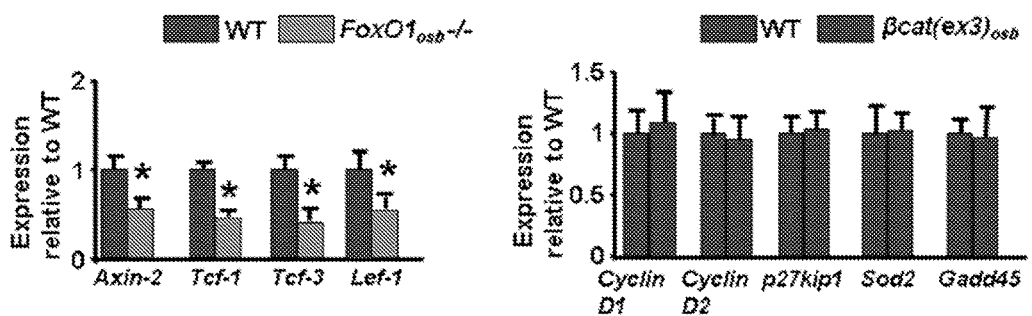
Fig. 47D
Fig. 47E

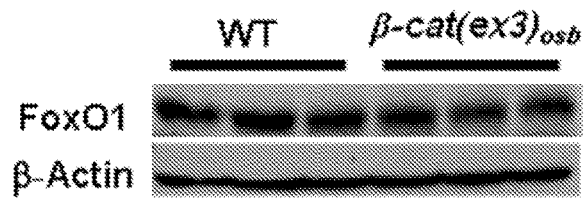
Fig. 47F
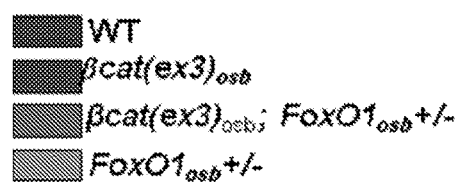
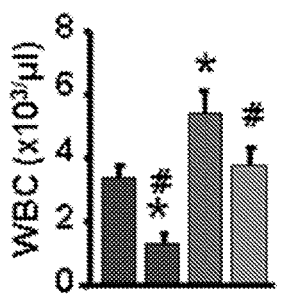
Fig. 48A
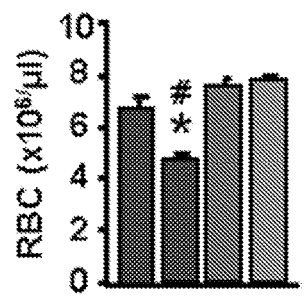
Fig. 48B
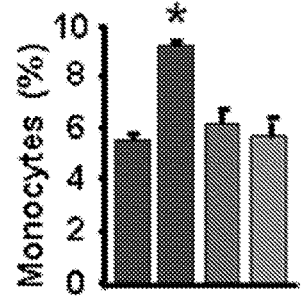
Fig. 48C
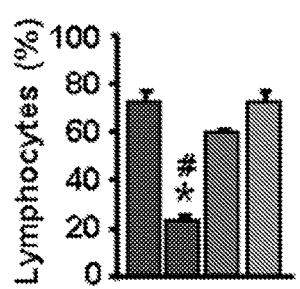
Fig. 48D
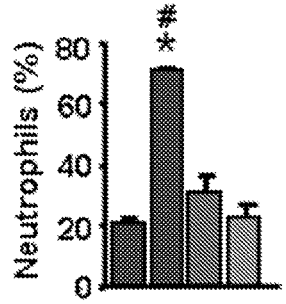
Fig. 48E
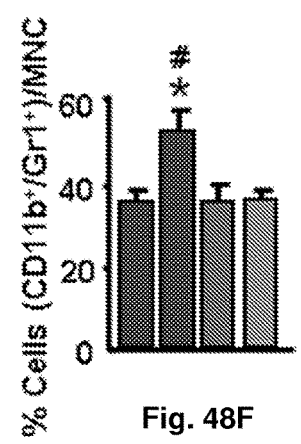
Fig. 48F

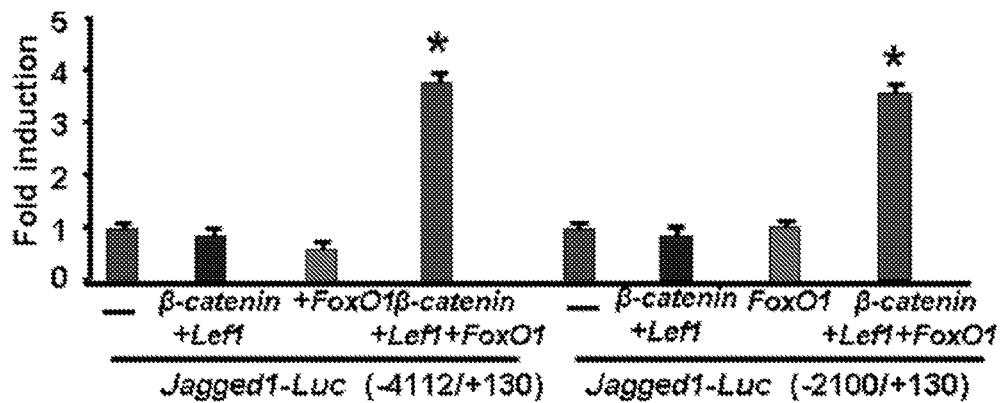
Fig. 57A
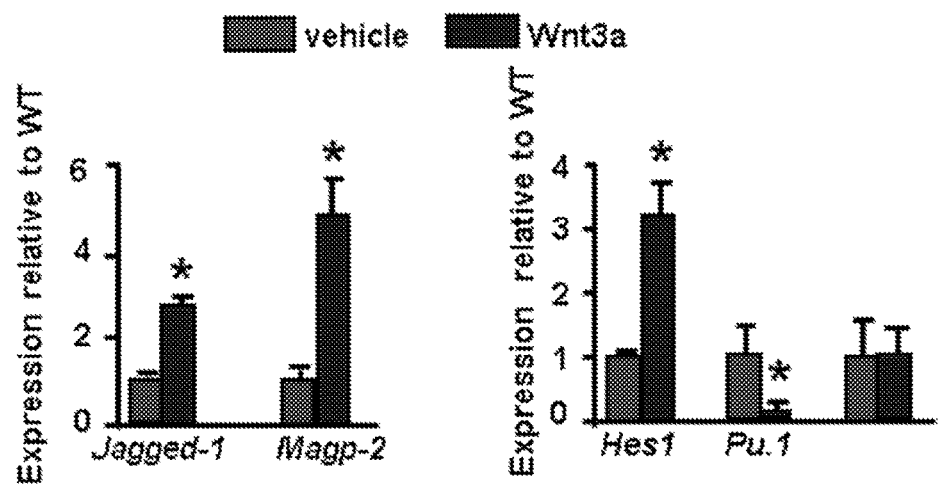
Fig. 57B
Fig. 57C

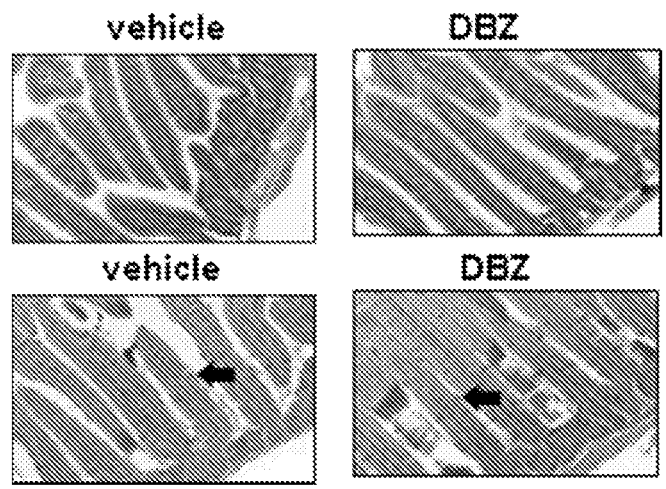
Fig. 58
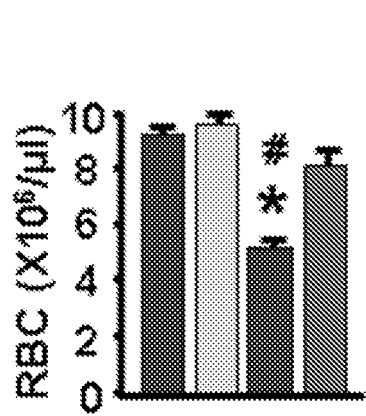 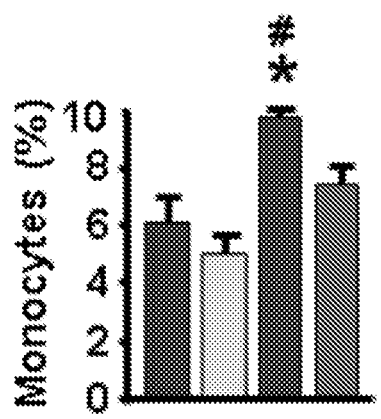
Fig. 59A  Fig. 59B

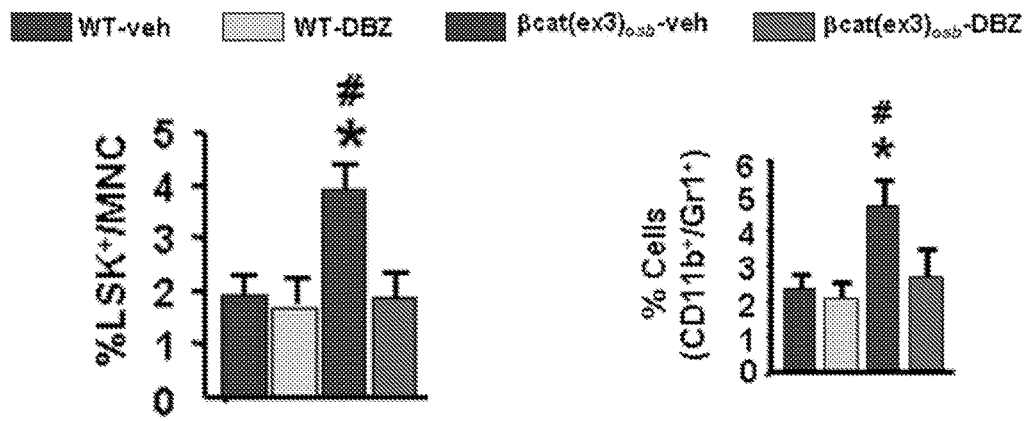
Fig. 60A
Fig. 60D
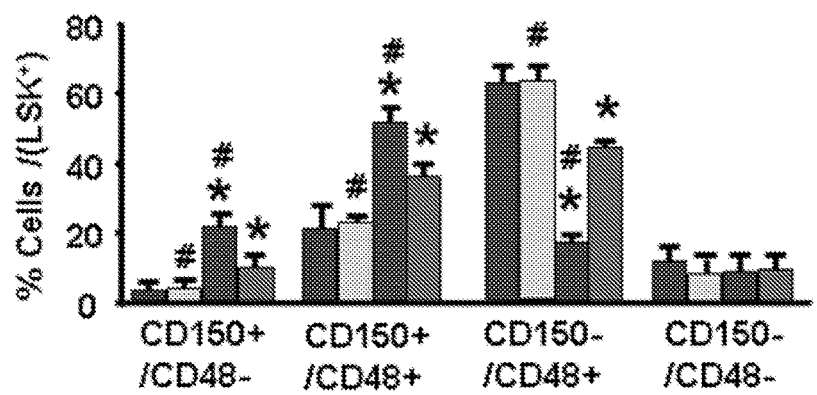
Fig. 60B
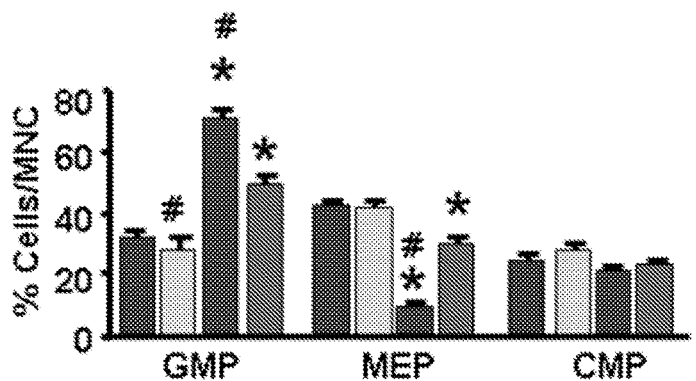
Fig. 60C

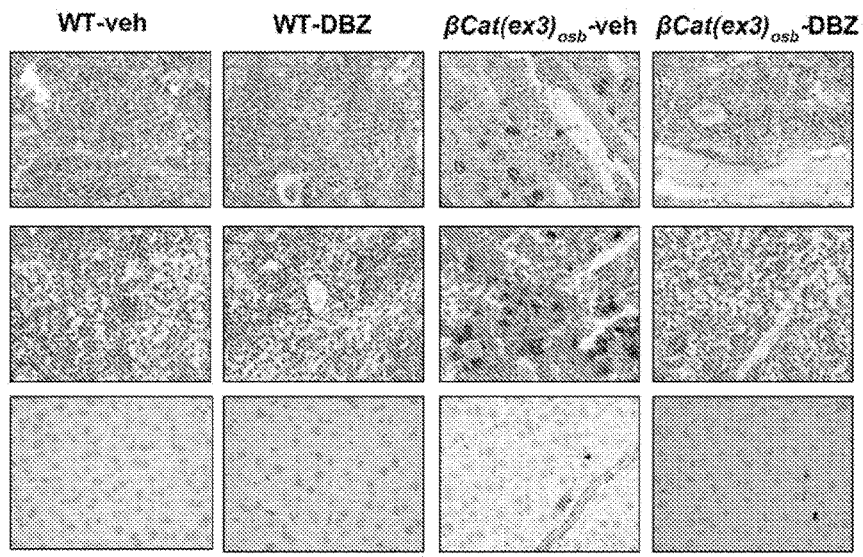
Fig. 63A
Fig. 63B
Fig. 63C
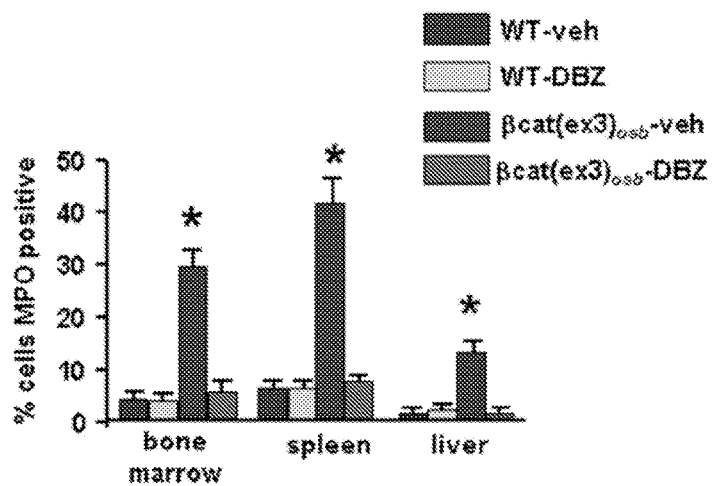
Fig. 64

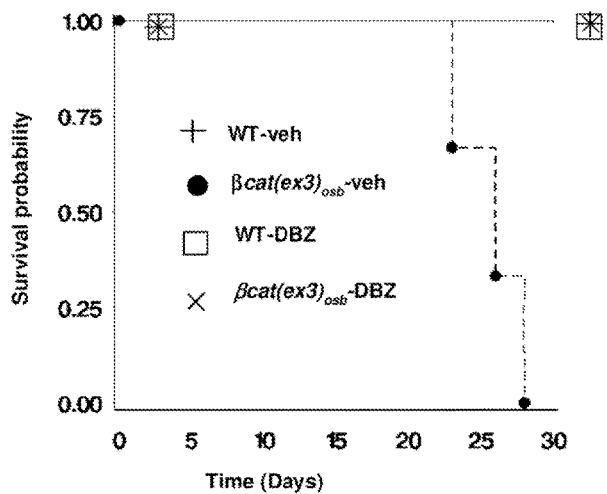
Fig. 65
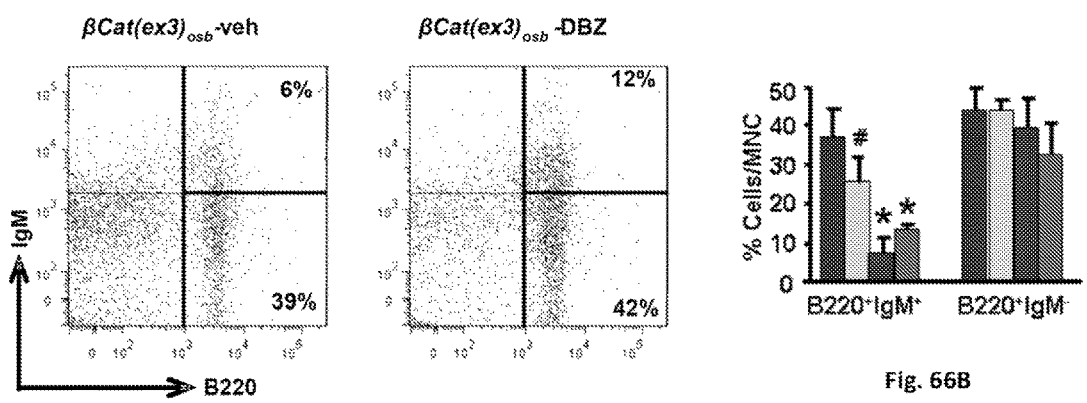
Fig. 66A
Fig. 66B

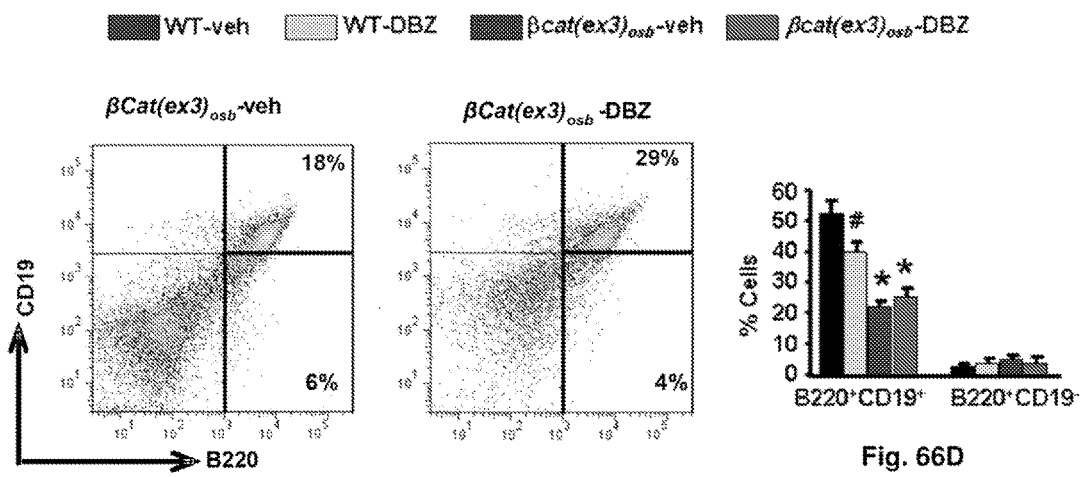
Fig. 66C
Fig. 66D
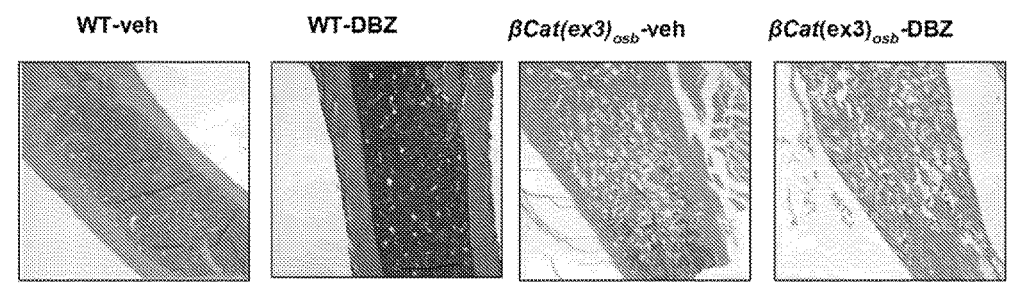
Fig. 67
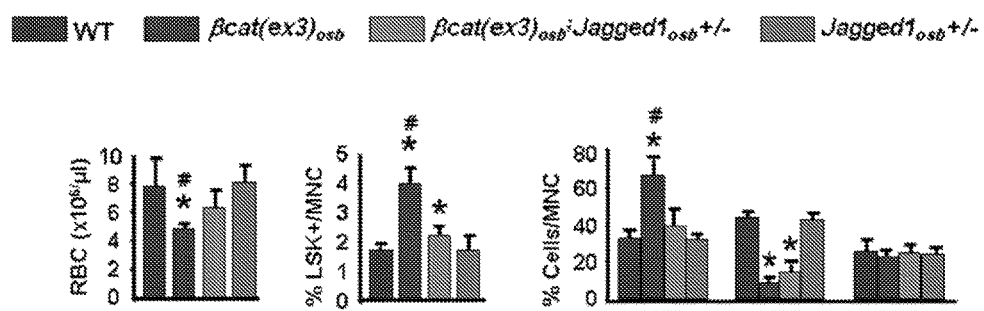
Fig. 68A
Fig. 68B
Fig. 68C

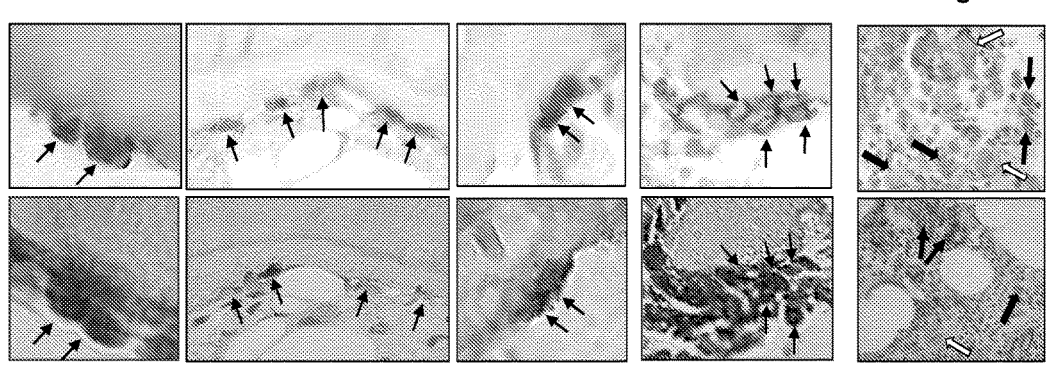
Fig. 71C
Fig. 71A   Fig. 71B   Fig. 71D
AML patient- nuclear β-catenin
β-catenin   Runx2   merged
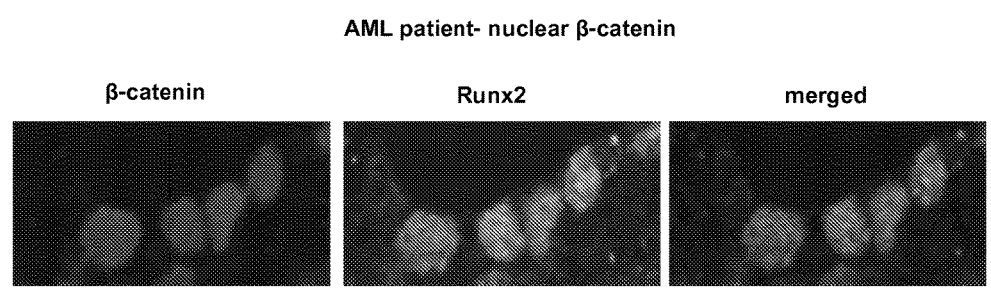
Fig. 72A
MDS/AML patient- membrane β-catenin
Fig. 72B healthy subject- membrane β-catenin AML patient - nuclear β-catenin

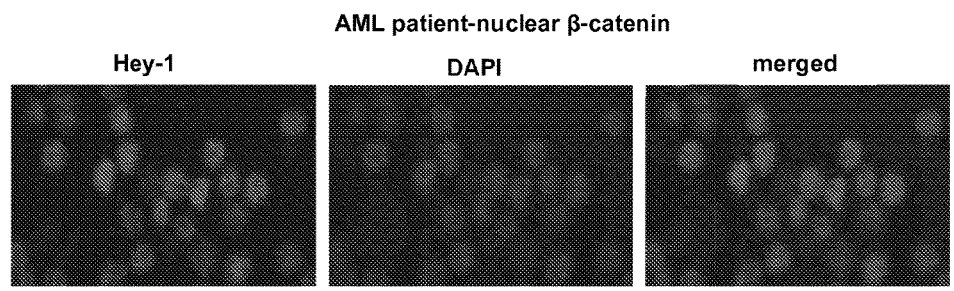
Fig. 74
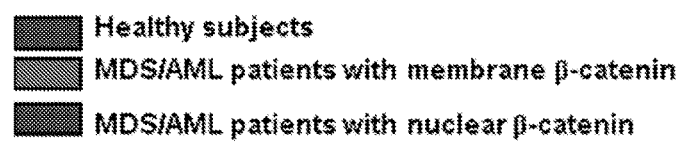
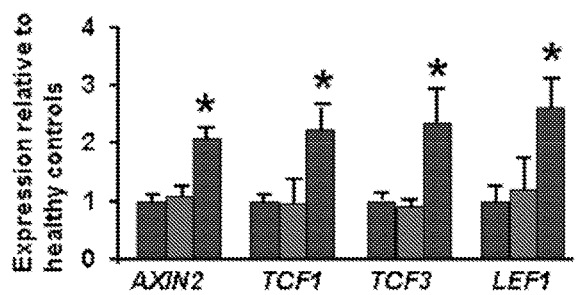
Fig. 75A
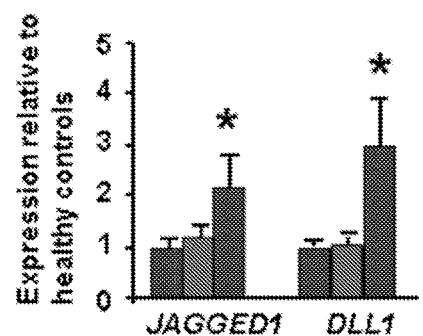
Fig. 75B
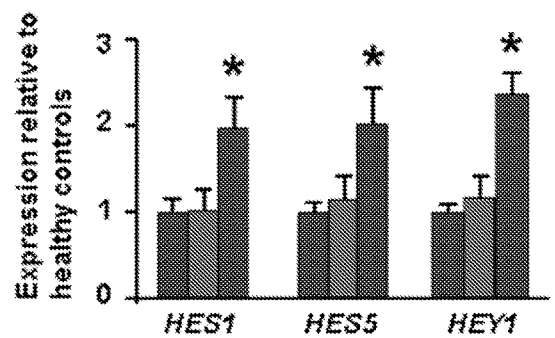
Fig. 75C

METHODS OF TREATING, PREVENTING AND DIAGNOSING LEUKEMIA AND OTHER BLOOD DISEASES AND DISORDERS

CROSS-REFERENCE TO RELATED APPLICATIONS

The present application is a U.S. national phase application under 35 U.S.C. § 371 of International Patent Application No. PCT/US2014/011295 filed Jan. 13, 2014, which claims the benefit of priority to U.S. provisional patent application Ser. No. 61/752,047 filed Jan. 14, 2013, the disclosures of all of which are hereby incorporated by reference in their entireties. The International Application was published in English on Jul. 17, 2014 as WO 2014/110506.

This invention was made with government support under AR054447, AR055931 and AG032959 awarded by the National Institutes of Health. The government has certain rights in the invention.

FIELD OF THE INVENTION

This invention is in the field of preventing and treating leukemia and other disorders of the blood, by inhibition of the Wnt canonical signal pathway, specifically β-catenin induced expression of Notch ligands. It is also in the field of diagnosing leukemia and other disorders of the blood, as well as for methods of drug screening.

BACKGROUND OF THE INVENTION

Hematopoiesis is the normal formation of blood cells in the bone marrow. Blood cells develop from pluripotential hematopoietic stem cells (HSCs). The first step in the hematopoietic differentiation process is the commitment of the stem cell to one of two large pathways: myeloid or lymphoid. A myeloid stem cell then matures into a myeloid blast. This blast can form red blood cells, platelets or several types of white blood cells. A lymphoid stem cell matures into a lymphoid blast, which forms into one of several types of white blood cells, such as B cells or T cells. Most blood cells mature in the bone marrow and then move into the blood vessels. Hematopoiesis takes place in a region termed the bone marrow niche. In addition to hematopoietic stem cells, endothelial cells, stromal cells, adipocytes, fibroblasts, and bone cells are found in this niche.

Over the last few years it has become increasingly apparent that several stromal cell types in the bone marrow microenvironment influence the fate of hematopoietic stem cells. These cells include perivascular cells, Nestin-expressing mesenchymal stem cells (MSCs), leptin receptor and SCF-expressing perivascular cells, and endothelial cells (Mendez-Ferrer et al., 2010; Ding et al., 2012; Arai et al., 2004; Lo et al., 2009; Kiel et al., 2005; Sugiyama et al., 2006; Butler et al., 2010; Winkler et al., 2012). The osteoblast, a bone forming cell, is another important determinant of the function of hematopoiesis and the size of the HSC niche (Calvi et al., 2003; Zhang et al., 2003). HSCs within the bone marrow reside preferentially next to the endosteal bone surface suggesting that osteoblasts regulate homing of HSCs (Heissig et al., 2002; Shiozawa et al., 2011). Alterations in osteoblast numbers correlate with changes in the number of long term repopulating HSCs, defects in bone marrow hematopoiesis, and the development of extramedullar hematopoiesis (Visnjic et al., 2004; Calvi et al, 2003; Zhang et al., 2003). Osteoblast progenitors are implicated in HSC mobilization and lineage determination survival and proliferation, initiate ectopic HSC niche formation, and regulate B lymphopoiesis (Mayack and Wagers, 2008; Wu et al., 2008; Zhu et al., 2007; Taichman and Emerson, 1994; Taichman et al, 1996; Chan et al., 2009). The mechanisms through which osteoblasts affect hematopoiesis are now being elucidated and as they emerge, they suggest a variety of signals that can affect different aspects of hematopoiesis. A functional interaction between osteoblasts and HSCs, involving engagement of Notch1/Jag1, signaling promotes HSC proliferation (Calvi et al., 2003; Zhang et al., 2003), whereas inactivation of Wnt signaling in osteoblasts disrupts stem cell quiescence, leading to a loss of self-renewal potential through a Shh-mediated pathway (Schaniel et al., 2011). Recently, disruption of HIF signaling in osteoprogenitors was shown to directly modulate erythropoiesis (Rankin et al., 2012).

Mesenchymal cells, from which osteoblasts originate, have been implicated in the maintenance of leukemia blasts mainly by promoting their localization to the bone marrow. Mouse models of myeloproliferative disorders (MPD) and myelodysplastic syndromes (MDS), conditions that in humans predispose one to acute myeloid leukemia (AML), are linked to genetic mutations in both hematopoietic and non-hematopoietic cells (Walkley et al., 2007; Kim et al., 2008). Implicating osteoblasts more directly in this process, is the finding that the disruption of the entire machinery of miRNA formation in osteoblasts resulted in MDS and AML development in mice (Raaijmakers et al., 2010). However, it is not known yet whether a single genetic event taking place in osteoblasts can induce leukemogenesis.

The canonical Wnt signaling pathway is equally important for hematopoiesis and skeletal homeostasis. In hematopoietic stem cells, the pathway affects multineage progenitor differentiation and is a major regulator of bone mass, mainly through its action in osteoblasts. Canonical Wnt signaling acts through β-catenin in early osteochondroprogenitors during skeletogenesis, to induce their differentiation into osteoblasts rather than chondrocytes (Hill et al., 2005; Rodda and McMahon, 2006; Day et al, 2005). β-catenin acts in osteoblasts to inhibit osteoclast formation and suppress bone resorption. This function of β-catenin has no effect on proliferation, differentiation or the bone forming properties of osteoblasts (Glass et al., 2005; Holmen et al., 2005). β-catenin is normally found in the cytoplasm of cells, but mutations may cause it to accumulate in the nucleus. Because of its bone protective properties, canonical Wnt signaling in osteoblasts is currently a major pharmacotherapeutic target.

Abnormal hematopoiesis leads to blood disorders including blood cancers. Every ten minutes, someone in the United States dies from a blood cancer. It was estimated that almost 150,000 people would be diagnosed with leukemia, lymphoma, or myeloma this year, and that an estimated 54,630 deaths from these three diseases combined would occur. Additionally, this year over 48,000 people are expected to be diagnosed with leukemia with almost 24,000 people expected to die of the disease this year. Moreover, leukemia causes about one-third of all cancer deaths in children younger than 15 years (The Leukemia and Lymphoma Society, Facts 2013, pages 1 and 2).

While there are several known treatments for blood cancers, including chemotherapy, radiation, immunotherapy, gene therapy, and stem cell transplantation, there is still a poor prognosis. In patients who are 65 years or older (65 is the median age at diagnosis), survival rates following chemotherapy are in the range of 10%. In younger patients, the survival rate is in the range of 30%, except in the very small fraction of patients. Various modifications of drug delivery and dose have had no significant impact. Additionally, all of these therapies have many unwanted side effects. Chemotherapy can cause extreme fatigue, hair loss, nausea, loss of appetite, and greater risks of infection. Radiation can cause extreme fatigue. Immunotherapy can cause headache, muscle aches, fever, weakness, and anemia. There is a risk of graft-versus-host disease with stem cell transplantation (The Leukemia and Lymphoma Society, Facts 2013, page 2-7). While molecular studies have further refined an understanding of the defects in this disease, none have provided a target for therapy.

Thus, there is a need for the development of additional therapies for leukemia, those without the unwanted, potentially dangerous side effects, as well as a need to identify and early diagnose those who have a blood cancer or disorder.

SUMMARY OF THE INVENTION

The present invention is based upon the surprising discovery that the constitutive activation of β-catenin in osteoblasts induces myelodysplasia (MDS) and acute myeloid leukemia (AML). The sequence of signaling events that mediate the malignant transformation of HSCs by osteoblasts is initiated by activation of canonical Wnt signaling in osteoblasts. Stabilized β-catenin upregulates expression of the Notch ligand, Jagged-1, in osteoblasts, subsequently leading to activation of Notch signaling in HSCs. Moreover, the presence of β-catenin in the nucleus is also indicative of MDS and AML.

One embodiment of the present invention is a method of treating and/or preventing leukemia and/or other blood diseases and/or disorders, comprising administering to a subject in need thereof, a therapeutically effective amount of an agent that inhibits canonical Wnt signaling in osteoblast precursors that leads to constitutive β-catenin activation. The inhibition can be accomplished by blocking the receptor that initiates Wnt signaling. The inhibition can also be accomplished by blocking the actual β-catenin activation, expression and/or activity.

A further embodiment of the present invention is a method of treating and/or preventing leukemia and/or other blood diseases and/or disorders, comprising administering to a subject in need thereof, a therapeutically effective amount of an agent that inhibits the activation, expression, and/or activity of Notch ligands in osteoblasts, including but not limited to, the Jagged-1 ligand.

A further embodiment of the present invention is a method of treating and/or preventing leukemia and/or other blood diseases and/or disorders, comprising administering to a subject in need thereof, a therapeutically effective amount of an agent that inhibits Notch signaling in hematopoietic cells. This inhibition can be accomplished by blocking the Notch receptor in hematopoietic cells.

Yet another embodiment of the present invention is a method of treating and/or preventing leukemia or other blood diseases and/or disorders, comprising administering to a subject in need thereof, a therapeutically effective amount of an agent or agents that inhibits a combination of at least two of the following: the receptor that initiates canonical Wnt signaling in osteoblast precursors; the activation, expression and/or activity of β-catenin; the activation, expression and/or activity of Notch ligands in osteoblasts; and Notch signaling in hematopoietic cells An additional embodiment of the present invention is a method of treating and/or preventing leukemia or other blood diseases and/or disorders, comprising administering to a subject in need thereof; a therapeutically effective amount of an agent that targets and kill osteoblasts that have constitutively active β-catenin.

Types of leukemia that can be treated and/or prevented by this method include, but are not limited to, acute lymphocytic leukemia (ALL), chronic lymphocytic leukemia (CLL), acute myeloid leukemia (AML), and chronic myeloid leukemia (CML). In a preferred embodiment, the leukemia is AML. Disorders of the blood would include, but are not limited to, myeloproliferative syndrome (MPS), myelodysplastic syndrome (MDS), MPN/MDS, a pre-AML condition with features of both a myeloproliferative neoplasm (MPN) and MDS, aplastic anemia, and anemia associated with kidney disease. In a preferred embodiment, the disorder is MDS.

Preferably, the subject is a mammal and in the most preferred embodiment, the mammal is a human.

Another embodiment of the present invention is a method of and/or assay for identifying and/or diagnosing the potential or actual development of leukemia or a blood disease or disorder, comprising testing osteoblasts from a subject at risk for developing leukemia or a blood disease or disorder, for the presence of β-catenin in the nucleus. Osteoblasts would be obtained from the bone of subject at risk for leukemia or blood diseases or disorders and the presence of β-catenin in the nucleus tested by methods known in the art, including but not limited to immunohistochemistry, immunofluoresence and flow cytometry.

Such a method of diagnosis would comprise:
1. Obtaining a sample of tissue or fluid from a subject at risk for developing leukemia or a blood disease or disorder:
2. Isolating osteoblasts from the sample of tissue or fluid;
3. Contacting the osteoblasts with a marker that identifies the presence of β-catenin in the nucleus; and
4. Inspecting the cells for the identification of the presence of β-catenin in the nucleus;
   wherein the presence of β-catenin in the nucleus indicates the subject has an increased potential for, or has, leukemia and/or a blood disorder.

A further embodiment of the present invention is a method of and/or assay for identifying and/or diagnosing the potential development of leukemia or a blood disease or disorder, comprising testing osteoblasts from a subject at risk for developing leukemia or a blood disease or disorder, for the expression of Notch ligands, including but not limited to, JAGGED-1 and DLL-1, and β-catenin target genes, including, but not limited to, Axin-2, Tcf-1, Tcf-3, and Lef-1, in their osteoblasts. Expression analysis can be done by any method known in the art including, but not limited to, microarrays; Southern blots; Northern blots; dot blots; primer extension; nuclease protection; subtractive hybridization and isolation of non-duplexed molecules using, for example, hydroxyapatite; solution hybridization; filter hybridization; amplification techniques such as RT-PCR and other PCR-related techniques such as PCR with melting curve analysis, and PCR with mass spectrometry; fingerprinting, such as with restriction endonucleases; and the use of structure specific endonucleases. mRNA expression can also be analyzed using mass spectrometry techniques (e.g., MALDI or SELDI), liquid chromatography, and capillary gel electrophoresis. Any additional method known in the art can be used to detect the presence or absence of the transcripts.

Such a method of diagnosis would comprise:
1. Obtaining a sample of tissue or fluid from a subject at risk for developing leukemia or a blood disease or disorder:
2. Isolating osteoblasts from the sample of tissue or fluid;
3. Isolating the nucleic acids from the osteoblasts;
4. Performing gene expression analysis on the nucleic acids from the osteoblasts;
wherein an increase in the expression of Notch ligands and/or β-catenin target genes as compared to the expression of these genes in healthy subjects would indicate that the subject has an increased potential for developing, or has, leukemia and/or a blood disorder.

The expression of the genes from the subject at risk for developing a blood disease or disorder can be compared to a reference value of the expression of the same genes in a healthy control or subject. The levels of expressed genes may be measured as absolute or relative. Absolute quantitation measure concentrations of specific DNA or RNA and requires a calibration curve. Relative quantification measures fold change differences of specific DNA or RNA in comparison to housekeeping genes. Relative quantification is usually adequate to investigate physiological changes in gene expression levels.

Types of leukemia that can be diagnosed by this method include, but are not limited to, acute lymphocytic leukemia (ALL), chronic lymphocytic leukemia (CLL), acute myeloid leukemia (AML), and chronic myeloid leukemia (CML). In a preferred embodiment, the leukemia is AML. Disorders of the blood would include, but are not limited to, myeloproliferative syndrome (MPS), myelodysplastic syndrome (MDS), MPN/MDS, a pre-AML condition with features of both a myeloproliferative neoplasm (MPN) and MDS, aplastic anemia, and anemia associated with kidney disease. In a preferred embodiment, the disorder is MDS. In a particularly preferred embodiment, subjects who have MDS would benefit from this diagnostic tool because it has been shown that those individuals with AML that arose from MDS in particular have an accumulation of β-catenin in the nucleus of their osteoblasts.

The present invention also provides for methods and tools for drug design, testing of agents, and tools for basic research into the causes and etiology of blood cancers and blood disorders.

One embodiment is a method and/or assay for screening and/or identifying a test agent for the prevention and/or treatment of leukemia and/or blood diseases and/or disorders, comprising contacting or incubating the test agent with β-catenin, and detecting the presence of a complex between the test agent and β-catenin, wherein if a complex between the test agent and the β-catenin is detected, the test agent is identified as a prevention and/or treatment for leukemia and/or blood disorders.

Another embodiment of the present invention is a method and/or assay for screening and/or identifying a test agent for the prevention and/or treatment of leukemia and/or blood diseases and/or disorders, comprising contacting or incubating the test agent with the receptor that initiates Wnt signaling, wherein if the test agent binds to the receptor, the test agent is identified as a prevention and/or treatment for leukemia and/or blood disorders.

Another embodiment of the present invention is a method and/or assay for screening and/or identifying a test agent for the prevention and/or treatment of leukemia and/or blood diseases and/or disorders, comprising contacting or incubating the test agent with β-catenin and a known antibody of β-catenin, and detecting the presence and quantity of unbound antibody, wherein the presence of the unbound antibody indicates that the test agent is binding to the polypeptide, and the test agent is identified as a prevention and/or treatment for leukemia and/or blood disorders.

A further embodiment is a method and/or assay for screening and/or identifying a test agent for the prevention and/or treatment of leukemia and/or blood diseases and/or disorders, comprising contacting or incubating the test agent with a Notch ligand, and detecting the presence of a complex between the test agent and Notch ligand, wherein if a complex between the test agent and the Notch ligand is detected, the test agent is identified as a prevention and/or treatment for leukemia and/or blood disorders.

Another embodiment of the present invention is a method and/or assay for screening and/or identifying a test agent for the prevention and/or treatment of leukemia and/or blood diseases and/or disorders, comprising contacting or incubating the test agent with a Notch receptor, wherein if the test agent binds to the receptor, the test agent is identified as a prevention and/or treatment for leukemia and/or blood disorders.

Another embodiment of the present invention is a method and/or assay for screening and/or identifying a test agent for the prevention and/or treatment of leukemia and/or blood diseases and/or disorders, comprising contacting or incubating the test agent with a Notch ligand, and a known antibody of the Notch ligand, and detecting the presence and quantity of unbound antibody, wherein the presence of the unbound antibody indicates that the test agent is binding to the polypeptide, and the test agent is identified as a prevention and/or treatment for leukemia and/or blood disorders.

The preferred Notch ligands are JAGGED-1 and DLL-1.

These methods and assays can be performed with the polypeptides and test agents, and antibodies, if applicable, free in solution, or affixed to a solid support. The polypeptides and antibodies may be labeled by any method known in the art.

High throughput screening can also be used to screen the test agents. Small peptides or molecules can be synthesized and bound to a surface and contacted with the polypeptides encoded by the gene signature transcripts, and washed. The bound peptide is visualized and detected by methods known in the art.

A further embodiment of the present invention is a method and/or assay for screening and/or identifying a test agent for the prevention and/or treatment of leukemia and/or blood diseases and/or disorders comprising contacting or incubating a test agent with a nucleotide encoding β-catenin or Notch ligands, and determining if the test agent binds to the nucleotide, wherein if the test agent binds to the nucleotide, the test agent is identified as a therapeutic or preventative agent for leukemia and/or blood disorders.

A further embodiment of the present invention is a method and/or assay for screening and/or identifying a test agent for the prevention and/or treatment of leukemia and/or blood disease and/or disorders comprising contacting or incubating a test agent with a nucleotide encoding β-catenin or Notch ligands, which expresses a measurable phenotype, and measuring the phenotype before and after contact or incubation with the test agent, wherein if the expression of the measurable phenotype is decreased after the contact or incubation with the test agent, the test agent is identified as a therapeutic or preventative agent for leukemia and/or blood disorders.

The measurable phenotype can be one that is native to the gene or one that is artificially linked, such as a reporter gene.

A further embodiment of the present invention is a method and/or assay for screening and/or identifying a test agent for the prevention and/or treatment of leukemia and/or blood diseases and/or disorders comprising transforming a host cell with a gene construct comprising a nucleotide encoding β-catenin or Notch ligands, detecting the expression of the nucleotide in the host cell, contacting or incubating the test agent with the host cell, and detecting the expression of the nucleotide from the host cell after contact or incubation with the test agent, wherein if the expression of the nucleotide is reduced or decreased after contact with the test agent, the test agent is identified as a therapeutic or preventative agent for leukemia and/or blood disorders.

A further embodiment of the present invention is a method and/or assay for screening and/or identifying a test agent for the prevention and/or treatment of leukemia and/or blood diseases and/or disorders comprising detecting the phenotype of an animal with constitutive active β-catenin or Notch ligands, contacting or incubating or administering a test agent to the animal, detecting the phenotype after the contact or incubation or administration of the test agent, wherein if the phenotype of the animal changes after the contact or incubation or administration of the test agent, the test agent is identified as a therapeutic or preventative agent for leukemia and/or blood disorders.

Such an animal can be genetically altered to have the phenotype, or the phenotype can be naturally occurring.

The preferred Notch ligands are JAGGED-1 and DLL-1.

A further embodiment of the present invention is a method and/or assay for screening and/or identifying a test agent for the prevention and/or treatment of leukemia and/or blood diseases and/or disorders comprising obtaining osteoblasts or other cells with the constitutive active β-catenin phenotype, detecting or measuring the active β-catenin phenotype in the cell, contacting or incubating the cell with a test agent, and detecting or measuring the phenotype of the activated β-catenin after contact or incubation with the test agent, wherein if the phenotype of the cell changes after the contact or incubation with the test agent, the test agent is identified as a therapeutic or preventative agent for leukemia and/or blood diseases and/or disorders.

Such cells can have the activated β-catenin phenotype naturally and may include osteoblasts from patients with leukemia such as AML or a disorder such as MDS, or the cells can have the phenotype through genetic manipulation.

The present invention also includes kits.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

In many of the figures, wild type mice are designated "WT". and mononuclear cells are designated "MNC".

FIG. 1 is Kaplan-Meier survival curves showing reduced survival of βcat(ex3)$_{osb}$ mice (n=8) compared with wild type littermates (n=10).

FIG. 2 are graphs depicting the percentage of various blood cells in βcat(ex3)$_{osb}$ mice as compared with wild type littermates. In every graph, the wild type group is represented by the left hand bar, and the βcat(ex3)$_{osb}$ mice group the right hand bar. FIG. 2A shows red blood cells (anemia), FIG. 2B show monocytes (monocytosis), FIG. 2C shows lymphocytes (lymphopenia), and FIG. 2D shows neutrophils (neutrophilia). n=6 mice per group. *p<0.05 versus WT. Results are mean±SD.

FIG. 7 depicts histomorphological analysis of the spleen of βCat(ex3)$_{osb}$ mice and wild type mice.

FIGS. 8A and 8B depicts PCR analysis of genomic DNA from osteoblasts, and various indicated hematopoietic cells of wild type and βCat(ex3)$_{osb}$ mice. n=5 mice per group, results from 2 independent experiments.

FIG. 9 shows graphs of the results of quantitative real-time PCR analysis of β-catenin target genes, Axin-2, Tcf1, Tcf-3 and Lef-1 in bone marrow hematopoietic cells (CD45+CD34+CD31+) of wild type and βCat(ex3)$_{osb}$ mice (FIG. 9A), in the spleen (FIG. 9B), and the bone (FIG. 9C). In every graph, the wild type group is represented by the left hand bar, and the βcat(ex3)$_{osb}$ mice group the right hand bar. n=5 mice per group, results from 2 independent experiments.

FIG. 16 are graphs with the percentage of mesenchymal cells (FIG. 16A), Nestin expressing cells (FIG. 16B), immature osteoblastic cells (FIG. 16D), endothelial expressing perivascular cells (FIG. 16E), and leptin receptor expressing perivascular cells (FIG. 16F), and Nestin expression in non-hematopoitic CD45–/CD34–/Lin– cells from βCat (ex3)$_{osb}$ mice (FIG. 16C). In every graph, the wild type group is represented by the left hand bar, and the βcat (ex3)$_{osb}$ mice group the right hand bar, n=6 mice per group. *p<0.05 versus WT. Results are mean±SD.

FIG. 17E shows spleen sections from βCat(ex3)$_{osb}$ mice showing blast infiltration. Arrows indicate dysplastic megakaryocytes. FIG. 17F show representative abnormal cells from the spleen of βCat(ex3)$_{osb}$ mice. Dotted arrow in the first panel indicates large nucleoli. The arrow in the second panel indicates immature cells with open chromatin characteristic of blasts, and arrows in the last two panels indicate abnormal megakaryocytes. Images taken at 400×. FIG. 17G are liver sections from βCat(ex3)$_{osb}$ and wild type mice (H&E). Arrow shows a cluster of immature cells with atypical nuclear appearance in βCat(ex3)$_{osb}$ mice (60×). n=25 mice per group.

FIG. 18 depicts myeloperoxidase (MPO) staining of long bone (FIG. 18A), spleen (FIG. 18B) and liver (FIG. 18C) in wild type (left hand panel of each figure) and βCat(ex3)$_{osb}$ mice (right hand panel of each figure) showing massive invasion of myeloid cells. FIG. 18D shows CD117 (C-kit) staining of bone sections in wild type mice (left hand panel) and βCat(ex3)$_{osb}$ mice (right hand panel) showing CD117+ blasts in βCat(ex3)$_{osb}$ mice. FIG. 18E shows immunostaining of bone sections in wild type mice (left hand panel) and βCat(ex3)$_{osb}$ mice (right hand panel) with CD13 showing myeloid/monocytic infiltration in βCat(ex3)$_{osb}$ mice. Pictures were taken at 60× magnification.

FIG. 19A is flow cytometry analysis of B-cell populations in the bone marrow of wild type (left panel) and βCat(ex3)$_{osb}$ mice (right panel).

FIG. 21 is a graph depicting the percentage of B cell progenitors in the lymph nodes. In the graph, the wild type group is represented by the left hand bar, and the βcat (ex3)$_{osb}$ mice group the right hand bar.

FIG. 22A depicts flow cytometry analysis of CD4 and CD8 expression in the thymus of wild type (left hand panel) and βCat(ex3)$_{osb}$ mice (right hand panel) and FIG. 22B shows the percentage of T-cells in the thymus of wild type and βCat(ex3)$_{osb}$ mice. In the graph, the wild type group is represented by the left hand bar, and the βcat(ex3)$_{osb}$ mice group the right hand bar. n=6 mice per group. *p<0.05 versus WT. All flow cytometry data are representative of five independent experiments. Results are mean±SD.

FIG. 24 depicts the results of clonogenic assays in the bone marrow of wild type and βCat(ex3)$_{osb}$ mice with M-CSF.

FIG. 25 depicts the results of clonogenic assays in the bone marrow of wild type and βCat(ex3)$_{osb}$ mice with GM-CSF and G-CSF. The figure is bone marrow sections stained with Giemsa of wild type (left hand panel) and βCat(ex3)$_{osb}$ mice (right hand panel) showing the lack of myeloid differentiation in βCat(ex3)$_{osb}$ mice bone marrow cells. FIG. 25A shows mice treated with GM-CSF and FIG. 25B shows mice treated with G-CSF. n=6 mice per group. Results of representative of three independent experiments. *p,0.05 versus WT. Results of mean±SD.

FIG. 26 are graphs depicting the results of clonogenic assays in the bone marrow of wild type and βCat(ex3)$_{osb}$ mice with M-CSF, GM-CSF and G-CSF and show the percentage of immature myeloid cells in the bone marrow of wild type and βCat(ex3)$_{osb}$ mice after treatment with M-CSF (FIG. 26A); GM-CSF (FIG. 26B); and G-CSF (FIG. 26C). In every graph, the wild type group is represented by the left hand bar, and the βcat(ex3)$_{osb}$ mice group the right hand bar. n=6 mice per group. Results of representative of three independent experiments. *p,0.05 versus WT. Results of mean±SD.

FIG. 27A is G-banding karyotype analysis of spleen cells from βCat(ex3)$_{osb}$ mice showing Robertsonian translocation between chromosomes 1 and 19. FIG. 27B is an inset showing the same abnormality in another cell.

FIG. 28 is a mouse chromosomal ideogram showing the areas of genetic gain and loss identified by aCGH in βCat (ex3)$_{osb}$ mice. Red bars indicate areas of gain whereas green bars represent areas of copy number loss.

FIG. 29 are sequence traces of whole-exome sequencing of certain βCat(ex3)$_{osb}$ versus wild type mice. FIG. 29A depicts mouse 1 for Tnfrsf21; FIG. 29B depicts mouse 2 for Tnfrsf21; FIG. 29C depicts mouse 3 for 4930596D0Rik; and FIG. 29D depicts mouse 1 for Crb1.

FIG. 30 are graphs of the percentages of cell and cell progenitors in WT and βCat(ex3)$_{osb}$ WT mice. FIG. 30A is LSK cells; FIG. 30B is myeloid progenitors; FIG. 30C is CD11b+/Mac+ cells; FIG. 30D is erythroid cells; and FIG. 30E is B-lymphopoiesis in the bone marrow. In every graph, the wild type group is represented by the left hand bar, and the βcat(ex3)$_{osb}$ mice group the right hand bar.

FIG. 31 are blood smears of WT-WT mice (FIG. 31A) and βCat(ex3)$_{osb}$_WT (FIG. 31B).

FIG. 34 shows the percentage of various cell types in the bone marrow of WT-WT and WT-βCat(ex3)$_{osb}$ mice.

FIG. 38 are peripheral blood smears from WT-WT (LTHSC) (FIG. 38A) and βCat(ex3)$_{osb}$_WT (LTHSC) mice (FIG. 38B) at 100×.

FIG. 40 are peripheral blood smears from wild type mice (left panels) and wild type mice transplanted with indicated hematopoietic cells from βCat(ex3)$_{osb}$ mice (right panels).

FIG. 41 show photographs of relative spleen size as well as graphic results of WT-WT mice and βCat(ex3)$_{osb}$-WT mice as well as WT mice transplanted with other hematopoietic cells from βCat(ex3)$_{osb}$.

FIG. 42 shows the percentage of cells in the liver and bone marrow of newborn (P1) βCat(ex3)$_{osb}$ mice.

FIG. 47A is immunoblots of coimmunoprecipitation (IP) of β-Catenin and FoxO1 in cell lysates from osteoblast cells. Blots were representatives of n=3. FIGS. 47B-E are graphs showing the results of real-time PCR analysis. FIG. 47B shows the results of PCR analysis of Axin-2, Tcf-1, Tcf-3 and Lef-1 expression in osteoblasts transfected with increasing concentrations of FoxO1 construct. EV denotes Empty vector. Data are representative of 3 independent experiments. *p<0.05 versus EV-transfected cells. FIG. 47C shows the results of real-time PCR analysis of Cyclin D1, Cyclin D2, p27kip1, Sod2 and Gadd45 expression in osteoblasts transfected with increasing concentrations of of β-Catenin. EV denotes Empty vector. Data are representative of 3 independent experiments. *p<0.05 versus EV-transfected cells. FIG. 47D shows quantitative real-time PCR analysis of Axin-2, Tcf1, Tcf-3 and Lef-1 in the bones of wild type and FoxO1$_{osb}$−/− mice. Total RNA was isolated from flushed long bones. n=4. *p<0.05 versus wild type. FIG. 47E depicts quantitative real-time PCR analysis of Cyclin D1, Cyclin D2, p27kip1, Sod2 and Gadd45 gene expression in bones of wild type and βCat(ex3)$_{osb}$ mice. Total RNA was isolated from flushed long bones. In FIG. 47E, the wild type group is represented by the left hand bar, and the βcat (ex3)$_{osb}$ mice group the right hand bar. n=4. *p<0.05 versus WT. FIG. 47F is immunoblot analysis showing FoxO1 protein levels in bones lysates of wild type and βCat(ex3)$_{osb}$ mice. Blot is representative of n=3. Results are mean±SD.

FIG. 49 shows various peripheral blood smears and histological analysis from WT, βcat(ex3)$_{osb}$,βcat(ex3)$_{osb}$; FoxO1$_{osb}$+/−, and FoxO1$_{osb}$−/− mice. In FIG. 49A images were taken at 100× magnification. In FIGS. 49B-F, images were taken at 60× magnification.

FIG. 53 depict results of flow cytometry analysis of Jagged-I expression in osteoblasts in WT (FIG. 53B) and βcat(ex3)$_{osb}$ mice (FIG. 53C).

FIG. 57A shows luciferase activity in HEK293T cells co-transfected with β-Catenin, Lef1, FoxO1 and Jagged1-Luc reporter constructs (−4112/+130) and (−2100/+130). Results show fold induction over respective Jagged1-Luc reporter constructs. * p<0.05 versus respective Jagged1-Luc. FIG. 57B depicts the results of real-time PCR analysis of Jagged-1 and Magp-2 in primary, calvaria-derived osteoblasts treated with vehicle or Wnt3a (50 ng/ml) for 24 hours, and FIG. 57C shows real-time PCR analysis of Hes1, Pu.1 and CEBPα in LSK+ population co-cultured with primary osteoblasts and treated with vehicle or Wnt3a (50 ng/ml) for 24 hours. In FIGS. 57B and C, the vehicle treated is represented by the left hand bar and the Wnt3a treated is represented by the right hand bar. n=4 replicates, *p<0.05 versus vehicle. Results are mean±SD.

FIG. 58 shows PAS staining of the intestines of vehicle and DBZ treated mice. Images are 60×.

FIG. 59 depicts graphs of numbers and percentages of cells in WT mice treated with a vehicle, WT mice treated with DBZ, βcat(ex3)$_{osb}$ treated with a vehicle, and βcat(ex3)$_{osb}$ treated with DBZ, respectively. FIG. 59A shows red blood cells, and FIG. 59B shows the percentage of monocytes in peripheral blood.

FIG. 60 depicts graphs of numbers and percentages of cells in the bone marrow of WT mice treated with a vehicle, WT mice treated with DBZ, βcat(ex3)$_{osb}$ treated with a vehicle, and βcat(ex3)$_{osb}$ treated with DBZ, respectively. FIG. 60A shows percent LSK cells; FIG. 60B shows percentages of LSK subpopulations; FIG. 60C shows percentages of myeloid progenitors; FIG. 60D shows percentage of CD11b+/Gr1+ population.

FIG. 62 are peripheral blood smears and histological sections of the bone marrow, spleen and liver of WT mice treated with vehicle, WT mice treated with DBZ, βCat(ex3)$_{osb}$ mice treated with vehicle, and βCat(ex3)$_{osb}$ mice treated with DBZ. In FIGS. 62D and 62E, solid arrows indicate abnormal cells with large nucleoli and dotted arrows indicate abnormal megakaryocytes in βCat(ex3)$_{osb}$ mice; white arrows indicate normal megakaryocytes in DBZ-treated βCat(ex3)$_{osb}$ mice. In FIG. 62F, the arrow indicates cluster of mononuclear cells. n=6 mice per group.

FIG. 63 is myeloperoxidase (MPO) staining of (A) bone marrow, (B) spleen, and (C) liver of WT mice treated with vehicle, WT mice treated with DBZ, βCat(ex3)$_{osb}$ mice treated with vehicle, and βCat(ex3)$_{osb}$ mice treated with DBZ. Images were taken at 60× magnification.

FIG. 64 is a graphical representation of the percent of cells that stained positive with MPO for WT mice treated with vehicle, WT mice treated with DBZ, βCat(ex3)$_{osb}$ mice treated with vehicle, and βCat(ex3)$_{osb}$ mice treated with DBZ, respectively, in the bone marrow, spleen, and liver.

FIG. 65 is a Kaplan-Meier survival curves for WT mice treated with vehicle, WT mice treated with DBZ, βCat(ex3)$_{osb}$ mice treated with vehicle, and βCat(ex3)$_{osb}$ mice treated with DBZ showing increased survival of DBZ treated mice. n=6 mice per group. *p<0.05 versus WT and #p<0.05 versus DBZ-treated βCat(ex3)$_{osb}$ group. Results are mean±SD.

FIG. 66A shows a representative image of flow cytometry analysis, and FIG. 66B a graph of the proportion of B-cell populations in the bone marrow of WT treated with vehicle, WT mice treated with DBZ, βCat(ex3)$_{osb}$ mice treated with vehicle, and βCat(ex3)$_{osb}$ mice treated with DBZ, respectively. FIG. 66C is a representative image of flow cytometry analysis and FIG. 66D a graph of proportion of B-cell populations in the spleen WT treated with vehicle, WT mice treated with DBZ, βCat(ex3)$_{osb}$ mice treated with vehicle, and βCat(ex3)$_{osb}$ mice treated with DBZ, respectively. n=6 mice per group. *p<0.05 versus WT and #p<0.05 versus DBZ-treated βCat(ex3)$_{osb}$ group. Results are mean±SD.

FIG. 67 are long bone sections imaged at 60× of WT mice treated with DBZ, βCat(ex3)$_{osb}$ mice treated with vehicle, and βCat(ex3)$_{osb}$ mice treated with DBZ.

FIG. 68 are graphs of numbers and percentages of cells in WT, βcat(ex3)$_{osb}$, βcat(ex3)$_{osb}$;Jagged1$_{osb}$+/− and Jagged1$_{osb}$+/− mice, respectively. FIG. 68A shows red blood cells; FIG. 68B shows LSK cells; FIG. 68C shows myeloid progenitors.

FIGS. 71A-D are images of bone marrow biopies. FIG. 71A (upper panels) show bone marrow biopsies from MDS and AML patients showing nuclear localization of β-catenin in osteoblasts by IHC, shown by arrows and identified as cuboid cells on the trabecular surface of the bone. FIG. 71A (lower panels) show serial sections stained with the osteoblast-specific, nuclear localized transcription factor Runx2. FIG. 71(B) show bone marrow biopsy from a representative healthy control showing cytoplasmic β-catenin staining in osteoblasts. The upper panel shows β-catenin staining and lower panel shows Runx2 staining in a serial section. FIG. 71C shows a bone marrow biopsy from the AML patient with nuclear β-catenin staining in osteoblasts, showing cytoplasmic β-catenin staining in myeloid (yellow arrows), megakaryocytes (white arrows) and erythroid (solid black arrows). FIG. 71D depicts a bone marrow biopsy from a healthy control showing cytoplasmic β-catenin staining in myeloid (yellow arrows), megakaryocytes (white arrows) and erythroid (solid black arrows). Images taken at 60×.

FIG. 72 are double immunofluorescence staining of osteoblasts with β-catenin (left panels) and Runx2 (middle panels) merged images on Runx2 and β-catenin (right panels) in bone marrow biopsies from MDS and AML patients and healthy controls. Images were taken at 60×. FIG. 72A shows nuclear β-catenin staining in a patient with AML; FIG. 72B shows membrane β-catenin staining in a patient with MDS/AML.

FIG. 73 are representative flow cytometry plots showing nuclear versus non-nuclear localization of β-catenin in osteoblasts isolated from bone biopsies of MDS/AML patients as CD34−/Lin−OCN+ cells, where OCN (osteocalcin) is an osteoblast-specific, non-nuclear protein commonly used for isolation of live osteoblastic cells.

FIG. 74 double immunofluorescence staining with Hey-1 of bone marrow from a patient with AML with nuclear β-catenin staining (same patient as shown in FIG. 72A). Images were taken at 60×.

FIGS. 75A-B are graphs of gene expression analysis of MDS/AML patients (n=8 patients per group) and healthy subjects. FIG. 75A shows β-catenin target genes CD34−/Lin−OCN+ osteoblasts; FIG. 75B shows JAGGED-1 and DLL-1 in CD34−/Lin−OCN+ osteoblasts; and FIG. 75C shows Notch target genes in CD34+/Lin+OCN− hematopoietic cells from MDS/AML patients or healthy subjects. In each graph, the left bar is the healthy control, the middle bar are MDS/AML patients with membrane β-catenin, and the right hand bar are MDS/AML patients with nuclear β-catenin. p<0.05 versus patients with non-nuclear β-catenin in osteoblasts and healthy subjects. Results are mean±SD. Results show a representative of two independent experiments with a total of N=3 for healthy subjects, 12 for MDS/AML patients with membrane localization of β-catenin and 11 for MDS/AML patients with nuclear β-catenin.

DETAILED DESCRIPTION OF THE INVENTION

Figure 3A:
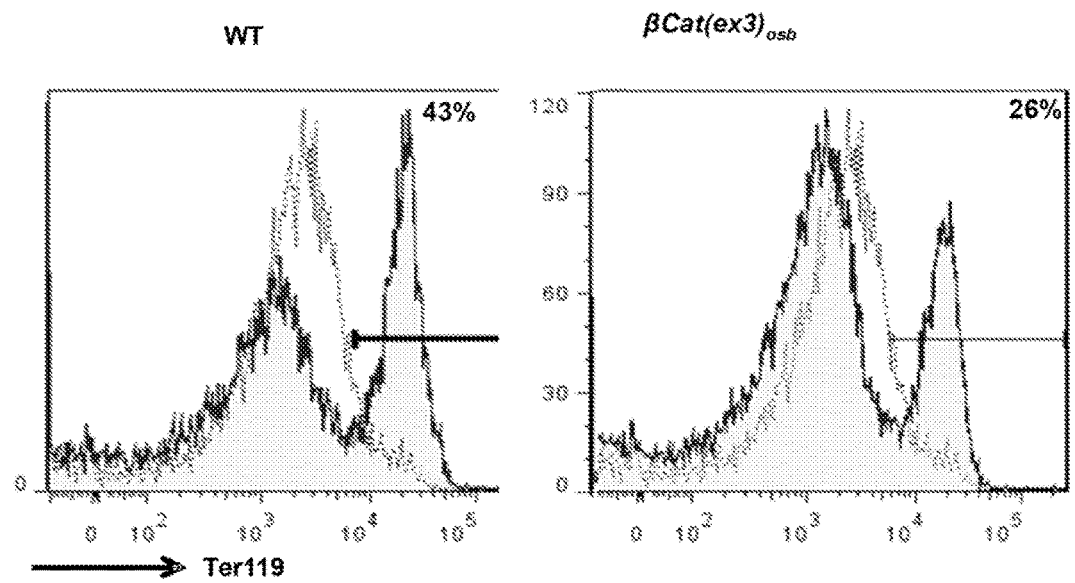
FIG. 3 depicts a representative flow cytometry analysis image (FIG. 3A), numbers (FIG. 3B), and percentage (FIG. 3C) of Ter119+ erythroid precursors in the bone marrow of βCat(ex3)$_{osb}$ mice as compared to wild type. In every graph, the wild type group is represented by the left hand bar, and the βcat(ex3)$_{osb}$ mice group the right hand bar. n=6 mice per group. *p<0.05 versus WT. Results are mean±SD.

The present invention relates to methods of treating and/or preventing leukemia or other blood disorders by inhibiting one or more of the signaling events that mediate the malignant transformation of HSCs by osteoblasts, including the activation of canonical Wnt signaling in osteoblasts, the expression of β-catenin, the expression of the Notch ligand, Jagged-1, in osteoblasts, and the subsequent activation of Notch signaling in HSCs.

The present invention also relates to methods of diagnosing leukemia and disorders of the blood by the presence of β-catenin in the nucleus.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications The term "patient" as used in this application means a human subject. In some embodiments of the present invention, the "patient" is known or suspected of having or being at risk of developing leukemia, another blood cancer, a blood disorder, or other disease related to abnormal hematopoiesis.

The phrase "therapeutically effective amount" is used herein to mean an amount sufficient to cause an improvement in a clinically significant condition in the subject, or delays or minimizes or mitigates one or more symptoms associated with the disease or disorder, or results in a desired beneficial change of physiology in the subject.

The terms "treat", "treatment", and the like refer to a means to slow down, relieve, ameliorate or alleviate at least one of the symptoms of the disease or disorder, or reverse the disease or disorder after its onset.

The terms "prevent", "prevention", and the like refer to acting prior to overt disease or disorder onset, to prevent the disease or disorder from developing or minimize the extent of the disease or disorder, or slow its course of development.

The term "in need thereof" would be a subject known or suspected of having or being at risk of developing leukemia, another blood cancer, a blood disease, a blood disorder or other disease related to abnormal hematopoiesis.

A subject in need of treatment would be one that has already developed the disease or disorder. A subject in need of prevention would be one with risk factors of leukemia, or another blood cancer, disease or disorder, and/or symptoms of abnormal hematopoiesis.

The term "agent" as used herein means a substance that produces or is capable of producing an effect and would include, but is not limited to, chemicals, pharmaceuticals, biologics, small organic molecules, antibodies, nucleic acids, peptides, and proteins.

The terms "screen" and "screening" and the like as used herein means to test a subject or patient to determine if they have a particular illness or disease, or a particular manifestation of an illness or disease. The term also means to test an agent to determine if it has a particular action or efficacy.

The terms "identification", "identify", "identifying" and the like as used herein means to recognize a disease state or a clinical manifestation or severity of a disease state in a subject or patient. The term also is used in relation to test agents and their ability to have a particular action or efficacy.

The terms "prediction", "predict", "predicting" and the like as used herein means to tell in advance based upon special knowledge.

The terms "diagnosis", "diagnose", diagnosing" and the like as used herein means to determine what physical disease or illness a subject or patient has.

The term "reference value" as used herein means an amount or a quantity of a particular protein or nucleic acid in a sample from a healthy control or healthy subject.

The terms "healthy control", "healthy subject" and the like are used interchangeably in this application and are a human subject who is not suffering from a blood disease, a blood cancer, or a blood disorder.

As used herein, the term "isolated" and the like means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, an isolated genomic DNA, or a restriction fragment. In another embodiment, an isolated nucleic acid is preferably excised from the chromosome in which it may be found. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated material may be, but need not be, purified.

The term "purified" and the like as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The term "nucleic acid hybridization" refers to antiparallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an antiparallel hybrid).

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include, but are not limited to, plasmids, phages, and viruses.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA which codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct" or "gene construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "host cell" means any cell of any organism that is selected, modified, transformed, grown, used or manipulated in any way, for the production of a substance by the cell, for example, the expression by the cell of a gene, a DNA or RNA sequence, a protein or an enzyme. Host cells can further be used for screening or other assays, as described herein.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

"Nucleic acid" refers to deoxyribonucleotides or ribonucleotides and polymers thereof in either single- or double-stranded form. The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g, methyl phosphonates, phosphotriesters, phosphoroamidates, and carbamates) and with charged linkages (e.g., phosphorothioates, and phosphorodithioates). Polynucleotides may contain one or more additional covalently linked moieties, such as, for example, proteins (e.g., nucleases, toxins, antibodies, signal peptides, and poly-L-lysine), intercalators (e.g., acridine, and psoralen), chelators (e.g., metals, radioactive metals, iron, and oxidative metals), and alkylators. The polynucleotides may be derivatized by formation of a methyl or ethyl phosphotriester or an alkyl phosphoramidate linkage. Modifications of the ribose-phosphate backbone may be done to facilitate the addition of labels, or to increase the stability and half-life of such molecules in physiological environments. Nucleic acid analogs can find use in the methods of the invention as well as mixtures of naturally occurring nucleic acids and analogs. Furthermore, the polynucleotides herein may also be modified with a label capable of providing a detectable signal, either directly or indirectly. Exemplary labels include radioisotopes, fluorescent molecules, and biotin.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

As discussed above, non-hematopoietic cells are found in the bone marrow niche and have also been implicated in the pathogenesis of hematological malignancies. For example, mesenchymal cells have been shown to protect leukemia cells from chemotherapy (Iwamoto et al., 2007). Also, defective Rb, RARγ, and Notch signaling in hematopoietic and non-hematopoietic cells leads to myeloproliferative syndrome (MPS) in mice, which is a condition that predisposes one to acute leukemia development. MPS requires the presence of the mutation in both hematopoietic and non-hematopoietic cells (Kim et al., 2008; Walkley at al., 2007). A more recent study has shown that osteoblasts are also involved in the hematopoietic process, showing that the deletion of Dicer1 in osteoblast progenitors induces myelodysplasia, another condition that in humans can progress to AML (Raaijmakers et al., 2010). Also as discussed above, the canonical Wnt signaling pathway and β-catenin may play a role in the osteoblast involvement in hematopoiesis. While a link has been shown between osteoblasts and hematopoiesis, a specific signal or pathway in the osteoblasts that might affect hematopoiesis has not been identified.

Suggesting another level of complex interactions between mesenchymal stem cells and leukemia cells, karyotypic abmormalities are found in a pure population of MSCs in a significant proportion of patients with AML (Flores-Figueroa et al., 2005). In some of those cases with chromosomal alterations, the karyotype abnormalities are the same as those observed in their hematopoietic counterparts, but in the majority, they are totally different. Stromal cells from AML patients show trisomy 8 and monosomy 7 in a setting where leukemia blasts present the same abnormalities (Zhang et al., 1999). Disruption of the microRNA biogenesis and processing in osteoblasts resulted in the emergence of clonal neoplasms in a cell type of lineage clearly distinct from the osteoblastic one.

Based upon these findings, it was hypothesized that an activating mutation in the canonical Wnt signaling in osteoblast precursors alters hematopoietic stem cell fate and leads to the development of abnormal hematopoiesis, MDS and AML. The experiments set forth herein show that osteoblasts not only determine lineage specification of HSCs but have the ability to transform normal cells to malignant cells, and initiate leukemogenesis. The property is independent of changes in osteoblast numbers and bone forming properties of the osteoblast and only originates from de-regulation of a single specific pathway, canonical Wnt signaling.

Leukemogenic Transformation of Hematopoietic Cells by Osteoblasts Induces Cell-Autonomous Acute Myeloid Leukemia In Mice Using mice that express active β-catenin allele constitutively in their osteoblasts, it has been surprisingly shown that this constant β-catenin activation causes hematopoietic abnormalities and disfuntion. Specifically, these mice, designated βcat(ex3)$_{osb}$, were found to not only be anemic as compared to wild type littermates, but also suffered from peripheral blood monocytosis, neutrophilia, and lymphoctopenia (Example 2). Additionally, the hematopoietic stem cells of these mice tended to shift to a differentiation to the myeloid lineage, and myeloid cells were increased in their spleens and livers (Example 2). It was also found that these mice had abnormalities in other hematopoietic stem cell lines (Example 3).

Even more surprising, is the finding that these mice have myelodysplasia syndrome (MDS), a pre-leukemia disease, which is characterized by trilineage dyspoiesis, bone marrow dyplasia with variable percentage of blasts and a high rate of progression to AML. Indeed these mice spontaneously develop AML. The βcat(ex3)$_{osb}$ mice have all of the criteria for AML in mice (Kogan et al., 2002): blasts in the blood, an increase of immature and monocytic cells with atypical features as well as a decrease in B-lymphopoiesis (Example 5).

Genetic analysis of the βcat(ex3)$_{osb}$ mice show that the mice have clonal abnormalities as well, supporting the hypothesis that the constitutive activation of β-catenin in osteoblasts increases clonal progression in myeloid progenitors leading to AML (Example 6). Moreover, the AML phenotype is transferable when osteoblasts that express the constitutive active β-catenin allele are transplanted showing that the osteoblasts are responsible for the AML (Example 7).

It was also found that the molecule FOX01 transmits the β-catenin dependent signal from osteoblasts to HSCs (Example 9), and when the FOX01 allele is removed from the osteoblasts of the βcat(ex3)$_{osb}$ mice, the mice do not develop AML and live for at least a year (Example 10). Further investigation showed that the Notch ligand, Jagged-1, is the target molecule of the β-catenin activation in osteoblasts in synergy with FOX01 induces expression of the Notch ligand, Jagged-1, which in turn triggers downstream activation of Notch signaling in adjacent HSCs (Examples 11 and 12). Blocking this Notch signaling either pharmacologically (Example 13), genetically (Example 14), or with an antibody (Example 17) improved the hematopoietic disfunction, and reversed the progression to AML.

In summary, the substantial data in mice point to a model where the constitutive activation of canonical Wnt signaling in osteoblast precursors disrupts hematopoiesis by shifting the differentiation potential of hematopoietic stem cell progenitors to the myeloid lineage which results in the accumulation of granulocyte/monocyte progenitors and concomitant development of acute myeloid leukemia (AML). Moreover, the AML phenotype is associated with the clonal evolution at the cytogenetic level since clonal abnormalities are detected in leukemic blasts from mice with the constitutive activation of β-catenin a canonical Wnt target. At the molecular level, the β-catenin interacts with FOX01 in osteoblasts and together they induce expression of the Notch ligand Jagged-1 to induce HSC progenitors to AML.

Human Patients with MDS and AML have β-Catenin in the Nucleus of Osteoblasts

Consistent with the studies in mice, data from human patients with MDS and AML show involvement of β-catenin and osteoblasts. Thirty-five percent (35%) of patients with MDS, almost thirty-six percent (36%) of patients with AML, and over forty-five percent (45%) of patients with AML that arose from MDS had β-catenin in the nucleus of their osteoblasts, as compared to localization in the membrane found in all of the healthy controls (Example 15). Additionally, 36% of the patients with the nuclear localization had abnormalities of chromosome 5 and/or 7, the most common cytogenetic abnormalities in patients with MDS and AML. The β-catenin nuclear staining was notably present in 42% of these patients (Example 15).

Expression of Jagged-1 and DLL-1 was upregulated in the osteoblasts of MDS/AML patients with the β-catenin nuclear localization in osteoblasts. Expression of Notch transcriptional targets was also increased in the hematopoietic cells from the same patients (Example 15).

Even more remarkable was the fact that two "healthy controls" who showed nuclear β-catenin were re-evaluated and shown to have MDS and MPN/MDS (Example 15).

Taken together this data shows an in vivo pathway that originates in the osteoblast, and through a specific signal between the osteoblast and the HSC, disrupts HSC lineage determination and function, and leads to AML. The presence of AML is supported by the combination of characteristic leukemia hallmarks common chromosomal aberrations and progression toward cell autonomous AML in bone marrow transplant experiments. The sequence of signaling events that mediate the malignant transformation of HSCs by osteoblasts is initiated by activation of canonical Wnt signaling in osteoblasts, leading to the constitutive activation of β-catenin. Stabilized β-catenin upregulates expression of Jagged-1 in osteoblasts, subsequently leading to activation of Notch signaling in HSCs. Indicating a relevance of these observations to human AML, nuclear accumulation and activation of β-catenin in osteoblasts and parallel activation of Notch signaling in hematopoietic cells was identified in over a third of patients with MDS, AML and AML arising from prior MDS, demonstrating reproduction in humans of the entire signaling pathway, as well as in two individual "healthy" control subjects who were found, upon reassessment, to be suffering from MDS.

These findings are the basis for new and important diagnostic and therapeutic tools for leukemia, in particular acute myeloid leukemia, and other disorders related to abnormal hematopoiesis.

Treatment and Prevention of Abnormal Hematopoiesis and Leukemia

As shown herein, there is a specific in vivo pathway that originates in the osteoblast, and signals to the HSC, and subsequently disrupts normal HSC lineage differentiation and function and leads to AML. Specifically, activation of canonical Wnt signaling in osteoblasts activates β-catenin, which in turn upregulates expression of Notch ligands, specifically, but not limited to, Jagged-1, in osteoblasts, subsequently leading to activation of Notch signaling in HSCs. Thus, there are several potential targets for inhibition in the signalling pathway that would treat and/or prevent the abnormal hematopoiesis and eventual disease and leukemia.

Any agent that would block the activation, expression and/or action of a molecule or the receptor of the molecule in the pathway could be used as a treatment and/or prevention of abnormal hematopoiesis and/or blood disorders and/or leukemia. Such agents include but are not limited to chemicals, phytochemicals, pharmaceuticals, biologics, small organic molecules, antibodies, nucleic acids, peptides, and proteins. Antibodies are a preferred agent.

Inhibiting the pathway can also be effected using "decoy" molecules which mimic the region of a target molecule in the pathway, that another molecule, such as β-catenin or Notch ligands, binds and activates. The activating molecule, such as β-catenin or Notch ligand, would bind to the decoy instead of the target, and activation could not occur.

Inhibition can also be effected by the use of a "dominantly interfering" molecule, or one in which the binding portion of activating molecule, such as β-catenin, is retained but the molecule is truncated so that the activating domain is lacking. These molecules would bind to receptors in the pathway but be unproductive and block the receptors from binding to the activating molecule. Such decoy molecules and dominantly interfering molecule can be manufactured by methods known in the art.

One potential target for inhibition is at any level of the canonical Wnt signaling, either at the receptor binding level or at the level of activation, expression and/or activity of β-catenin in the osteoblasts. Agents that block receptor binding in the canonical Wnt signal pathway include, but are not limited to, Dicckopf 1 (DKK-1) and secreted frizzled related proteins (SFRPs). Agents that block the activation, expression and/or activity of β-catenin in the osteoblasts, especially in the nucleus, include, but are not limited to, curcumin, EGCG, quercetin, fisetin, resveratrol, lycopene, naphthalene derivatives, any agents that stabilizes the formation of β-catenin complex with APC, Axin2, GSK, or CKI, or increase the phosphorylation of β-catenin by these molecules, protesome inhibitors, and inhibitors of FoxO activation, expression and/or activity because FoxO1 is required for activation of Notch ligands upregulation by β-catenin.

Another potential target for inhibition as treatment and/or prevention of abnormal hematopoiesis and leukemia is inhibition of the activation, expression and/or activity of Notch ligands in osteoblasts, more specifically Jagged-1 and DLL-1. Agents that block Notch ligands include, but are not limited to, blocking antibodies against the Notch ligands (anti-Notch ligands antibodies), DNA vaccination, soluble Notch ligands-Fc and Notch-Fc decoys, and Notch antibodies (Kuhnert et al., 2011).

A further potential target for inhibition as a treatment and/or prevention of abnormal hematopoiesis and leukemia is inhibition of Notch signaling in hematopoietic cells. Agents that block the receptor of Notch signaling in hematopoietic cells could be used for this inhibition. Agents that inhibit Notch signaling in hematopoietic cells include, but are not limited to, γ-secretase inhibitors, such as DBZ ((2S)-2-[2-(3,5-difluorophenyl)-acetylamino]-N-(5-methyl-6-oxo-6,7-dihydro-5H-dibenzo[b,-d]azepin-7-yl)-propionamide) or DAPT (N—[N-(3,5-difluorophenacetyl)-L-alanyl]-S-phenylglycine t-butyl ester), and SEL-10, an inhibitor of Notch signaling that targets Notch for ubiquitin-mediated protein degradation (Guangyu Wu et al., 2001).

Inhibition of a combination of any of these targets in the pathway can be used to treat and/or prevent abnormal hematopoiesis and leukemia. For example, inhibition of activation of β-catenin and inhibition of Notch signaling in hematopoietic cells can be combined. This can be accomplished by administering one or more agents that inhibit these targets of the pathway.

Because it has been shown that osteoblasts that have constitutively activated β-catenin or β-catenin accumulated in the nucleus may have a particular mutation, targeting and selectively killing these mutated osteoblasts would serve to treat and/or prevent the abnormal hematopoiesis and disease caused by the constitutive activation of β-catenin. One such method would include the administration of an antibody specific for nuclear or activated β-catenin coupled to an agent that can kill or harm the osteoblast cell.

Moreover, as shown, genetic alterations also treat and prevent AML from developing. Thus, the use of gene therapy can be used to treat and/or prevent the abnormal hematopoiesis and/or leukemia that would result from this pathway and the constitutive activation of β-catenin. As an example, identifying the protein or miRNA that induces β-catenin nuclear localization in osteoblast would allow it to be to genetically modified, and/or allow correction of the mutation that causes these effects. Once identified, an miRNA, or a DNA encoding a protein or miRNA, can be made by recombinant methods known in the art, and delivered to the subject.

Classical gene therapies normally require efficient transfer of cloned genes into disease cells so that the introduced genes are expressed at suitably high levels. Following gene transfer, the inserted genes may integrate into the chromosomes of the cell, or remain as extrachromosomal genetic elements (episomes).

For the former situation, the DNA recombines with the endogenous gene that produces the protein or microRNA present in the cell. Such recombination requires a double recombination event which results in the correction of the mutation in the gene producing the protein or microRNA.

The more preferred situation is that the gene will be expressed by the cell from an extrachromosomal location.

Vectors for introduction of the DNA in either recombination or extrachromosomal reproduction are known in the art and have been discussed herein. Methods for introduction of genes into cells including electroporation, calcium phosphate co-precipitation, and viral transduction are known in the art.

One such method for delivering the nucleic acid is receptor mediated endocytosis where the nucleic acid is coupled to a targeting molecule that can bind to a specific cell surface receptor, inducing endocytosis and transfer of the nucleic acid into cells. Coupling is normally achieved by covalently linking poly-lysine to the receptor molecule and then arranging for (reversible) binding of the negatively charged nucleic acid to the positively charged poly-lysine component. Another approach utilizes the transferrin receptor or folate receptor which is expressed in many cell types. When producing the nucleic acid for this method of administration, the nucleic acid is linked to a molecule for increasing cellular uptake. Examples of conjugates/ligands that can be linked to the nucleic acid molecule include, but are not limited to, transferrin, folate, cholesterol moieties, duplex intercalators such as acridine, poly-L-lysine, and phosphoromonothioate.

Another method to administer the nucleic acid to the proper tissue is direct injection/particle bombardment, where the nucleic acid is be injected directly with a syringe and needle into a specific tissue, such as muscle.

An alternative direct injection approach uses particle bombardment ('gene gun') techniques: Nucleic acid is coated on to metal pellets and fired from a special gun into cells. Successful gene transfer into a number of different tissues has been obtained using this approach. Such direct injection techniques are simple and comparatively safe.

Another method for delivery of nucleic acid to the proper tissue or cell is by using adeno-associated viruses (AAV). Nucleic acid delivered in these viral vectors is continually expressed, replacing the expression of the nucleic acid that is not expressed in the subject. Also, AAV have different serotypes allowing for tissue-specific delivery due to the natural tropism toward different organs of each individual AAV serotype as well as the different cellular receptors with which each AAV serotype interacts. The use of tissue-specific promoters for expression allows for further specificity in addition to the AAV serotype.

Other mammalian virus vectors that can be used to deliver the DNA or RNA include oncoretroviral vectors, adenovirus vectors, Herpes simplex virus vectors, and lentiviruses.

Liposomes are spherical vesicles composed of synthetic lipid bilayers which mimic the structure of biological membranes. The nucleic acid to be transferred is packaged in vitro with the liposomes and used directly for transferring the nucleic acid to a suitable target tissue in vivo. The lipid coating allows the DNA or RNA to survive in vivo, bind to cells and be endocytosed into the cells. Cationic liposomes (where the positive charge on liposomes stabilize binding of negatively charged DNA), have are one type of liposome.

The nucleic acids can also be administered with a lipid to increase cellular uptake. The nucleic acids may be administered in combination with a cationic lipid, including but not limited to, lipofectin, DOTMA, DOPE, and DOTAP (such as described in Application No. WO0071096).

Other lipid or liposomal formulations including nanoparticles and methods of administration have been described as for example in U.S. Patent Publication 2003/0203865, 2002/0150626, 2003/0032615, and 2004/0048787. Methods used for forming particles are also disclosed in U.S. Pat. Nos. 5,844,107, 5,877,302, 6,008,336, 6,077,835, 5,972,901, 6,200,801, and 5,972,900.

Pharmaceutical Compositions and Methods of Administration

The present invention encompasses the administration of agents that inhibit receptors and molecules in a specific in vivo pathway that causes abnormal hematopoiesis and leukemia. Preferred methods of administration of the agents include oral; mucosal, such as nasal, sublingual, vaginal, buccal, or rectal; parenteral, such as subcutaneous, intravenous, bolus injection, intramuscular, or intraarterial; or transdermal administration to a subject. Thus, the agent must be in the appropriate form for administration of choice.

Such compositions for administration may comprise a therapeutically effective amount of the serotonin inhibitor and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

These compositions can take the form of solutions, suspensions, emulsions, tablets, pills, capsules, powders, sustained-release formulations, cachets, troches, lozenges, dispersions, suppositories, ointments, cataplasms (poultices), pastes, powders, dressings, creams, plasters, patches, aerosols, gels, liquid dosage forms suitable for parenteral administration to a patient, and sterile solids (e.g., crystalline or amorphous solids) that can be reconstituted to provide liquid dosage forms suitable for parenteral administration to a patient. Such compositions will contain a therapeutically effective amount of the compound, preferably in purified form, together with a suitable form of carrier so as to provide the form for proper administration to the patient. The formulation should suit the mode of administration.

Pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient over a prolonged period of time.

Pharmaceutical compositions adapted for nasal and pulmonary administration may comprise solid carriers such as powders which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain anti-oxidants, buffers, baceriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Selection of a therapeutically effective dose will be determined by the skilled artisan considering several factors which will be known to one of ordinary skill in the art. Such factors include the particular form of the inhibitor, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

The Use of Nuclear or Activated β-Catenin in Osteoblasts as a Diagnostic Method

As shown, the constitutive activation or nuclear accumulation of β-catenin in osteoblasts is indicative of disfunctional or abnormal hematopoiesis, which in turn leads to leukemia, in particular acute myeloid leukemia, and other disorders, such as myeloproliferative syndrome, myelodysplastic syndrome, aplastic anemia, and anemia associated with kidney disease.

Thus, the presence of β-catenin in the nucleus of osteoblasts can be a powerful tool in diagnosing leukemia, in particular AML, and other blood disorders, in particular, myelodysplastic syndrome or MDS. Because early detection is often critical in any cancer, this method of early diagnosis can potentially save and prolong lives, and allow patients at great risk for development of disease to obtain treatment early or before leukemia fully develops.

The validity of such a diagnostic test is demonstrated in Example 15 where two healthy controls were found to have nuclear β-catenin and were re-evaluated. Upon re-evaluation it was determined these two subjects had MDS and MPN/MDS.

The first step of the method or assay is to obtain osteoblasts from any biological fluid or tissue, including but not limited to, the bone, of subjects who are known to be at risk for leukemia, especially acute myeloid leukemia, or other blood disorders, especially MDS. Subjects who would be considered at risk for leukemia may have one or more risk factors associated with leukemia, such as smoking, or radiation exposure. Those subjects especially at risk who would benefit most from this diagnostic tool are those who already have MDS as it has been shown herein that patients with AML that arose from MDS are almost 50% likely to have an accumulation of β-catenin in the nucleus of osteoblasts.

Bone tissue is obtained from subjects using any technique known in the art including but not limited to biopsy.

Osteoblasts are isolated from the bone tissue by any method known in the art. One known method is to prepare bone cultures from the biopsied bone by creating a slurry from the bone and digesting with collagenase. Osteoblasts can be identified by flow cytometry, as, for example, a population of $CD34^-Lin^-Ocn^+$ cells, where OCN (osteocalcin) is an osteoblast-specific, non-nuclear protein commonly used for isolation of live osteoblastic cells (Eghbali-Fatourechi et al., 2005; Rubin et al., 2011; Manavalan et al., 2012).

The accumulation of β-catenin in the nucleus can be determined by any method known in the art including but not limited to, immunohistochemistry, immunofluoresence, and flow cytometry, using markers that are specific for nucleic (β-catenin as well as quantitative Western blot, immunoblot, quantitative mass spectrometry, enzyme-linked immunosorbent assays (ELISAs), radioimmunoassays (RIA), immunoradiometric assays (IRMA), and immunoenzymatic assays (IEMA) and sandwich assays using monoclonal and polyclonal antibodies.

Antibodies are a preferred method of detecting and measuring nuclear β-catenin. Such antibodies are available commercially or can be made by conventional methods known in the art. Such antibodies can be monoclonal or polyclonal and fragments thereof, and immunologic binding equivalents thereof. The term "antibody" means both a homologous molecular entity as well as a mixture, such as a serum product made up of several homologous molecular entities. Antibodies for use in these assays can be labeled covalently or non-covalently with an agent that provides a detectable signal. Any label and conjugation method known in the art can be used. Labels, include but are not limited to, enzymes, fluorescent agents, radiolabels, substrates, inhibitors, cofactors, magnetic particles, and chemiluminescent agents.

One particular marker to be used for the determination of osteoblast-specific, nuclear localized β-catenin is an antibody specific for transcription factor Runx2. Another marker for activated or nuclear β-catenin is a β-catenin antibody specific for activated/nuclear β-catenin, such as the Non-phospho (Active) β-Catenin (Ser33/37/Thr41) (D13A1) Rabbit mAb #8814 (Cell Signaling).

As β-catenin is found in the nuclear membrane/cytoplasm of healthy subjects, any accumulation of β-catenin in the nucleus is considered a positive result indicative of the strong potential development of leukemia and/or other blood disorders. A qualitatative or visual confirmation of β-catenin in the nucleus alone would denote the development of or risk of the development of disease. Although, a quantitative comparison of the amount of β-catenin found in a subject at risk to a known reference value of the amount of β-catenin in a healthy control can also be done as a diagnostic.

The Use of Differential Gene Expression as a Diagnostic Method

Either as a confirmation diagnosis method or assay, or a separate diagnosis method or assay, the isolated osteoblasts can be examined for the increased expression of Notch ligands, more specifically JAGGED-1 and DLL-1, and/or β-catenin target genes, including but not limited to, Axin-2, Tcf1, Tcf-3, and Lef-1.

An increase in expression of either the Notch ligands and/or the β-catenin target genes as compared to the expression of these molecules in healthy individuals or controls would be a positive result and indicative of the development of leukemia and/or a blood disorder, especially AML.

The nucleic acid can be obtained from any biological tissue or fluid, preferably osteoblasts from bone.

The nucleic acid is extracted, isolated and purified from the cells of the tissue or fluid by methods known in the art.

If required, a nucleic acid samples are prepared using known techniques. For is example, the sample can be treated to lyse the cells, using known lysis buffers, sonication, electroporation, with purification and amplification occurring as needed, as will be understood by those in the skilled in the art. In addition, the reactions can be accomplished in a variety of ways. Components of the reaction may be added simultaneously, or sequentially, in any order. In addition, the reaction can include a variety of other reagents which can be useful in the methods and assays and would include but is not limited to salts, buffers, neutral proteins, such albumin, and detergents, which may be used to facilitate optimal hybridization and detection, and/or reduce non-specific or background interactions. Also reagents that otherwise improve the efficiency of the assay, such as protease inhibitors, nuclease inhibitors, and anti-microbial agents, can be used, depending on the sample preparation methods and purity.

Once prepared, the nucleic acids are analyzed by methods known to those of skill in the art. The nucleic acid sequence corresponding to a gene can be any length, with the understanding that longer sequences are more specific. Preferably a nucleic acid corresponding to a signature gene is at least 20 nucleotides in length. Preferred ranges are from 20 to 100 nucleotides in length, with from 30 to 60 nucleotides being more preferred, and from 40 to 50 being most preferred.

In addition, when nucleic acids are to be detected preferred methods utilize cutting or shearing techniques to cut the nucleic acid sample containing the target sequence into a size that will facilitate handling and hybridization to the target. This can be accomplished by shearing the nucleic acid through mechanical forces, such as sonication, or by cleaving the nucleic acid using restriction endonucleases, or any other methods known in the art. However, in most cases, the natural degradation that occurs during archiving results in "short" oligonucleotides. In general, the methods and assays of the invention can be done on oligonucleotides as short as 20-100 base pairs, with from 20 to 50 being preferred, and between 40 and 50, including 44, 45, 46, 47, 48 and 49 being the most preferred.

One method of the invention is performing gene expression profiling of the sample. Gene expression profiling refers to examining expression of one or more RNAs in a cell, preferably mRNA. Often at least or up to 10, 100, 100, 10,000 or more different mRNAs are examined in a single experiment.

Methods for examining gene expression, are often hybridization based, and include, Southern blots; Northern blots; dot blots; primer extension; nuclease protection; subtractive hybridization and isolation of non-duplexed molecules using, for example, hydroxyapatite; solution hybridization; filter hybridization; amplification techniques such as polymerase chain reaction or RT-PCR and other PCR-related techniques such as PCR with melting curve analysis, and PCR with mass spectrometry; fingerprinting, such as with restriction endonucleases; and the use of structure specific endonucleases. mRNA expression can also be analyzed using mass spectrometry techniques (e.g., MALDI or SELDI), liquid chromatography, and capillary gel electrophoresis. Any additional method known in the art can be used to detect the presence or absence of the transcripts.

Alternatively, the level of protein product of the genes can be measured from a protein sample from the biological tissue or fluid using methods described herein.

For a general description of these techniques, see also Sambrook et al. 1989; Kriegler 1990; and Ausebel et al. 1990.

A preferred method for the detection of the genes and transcripts is the use of arrays or microarrays. These terms are used interchangeably and refer to any ordered arrangement on a surface or substrate of different molecules, referred to herein as "probes." Each different probe of any array is capable of specifically recognizing and/or binding to a particular molecule, which is referred to herein as its "target" in the context of arrays. Examples of typical target molecules that can be detected using microarrays include mRNA transcripts, cRNA molecules, cDNA, PCR products, and proteins.

Microarrays are useful for simultaneously detecting the presence, absence and quantity of a plurality of different target molecules in a sample. The presence and quantity, or absence, of the probe's target molecule in a sample may be readily determined by analyzing whether and how much of a target has bound to a probe at a particular location on the surface or substrate.

In a preferred embodiment, arrays used in the present invention are "addressable arrays" where each different probe is associated with a particular "address."

The arrays used in the present invention are preferable nucleic acid arrays that comprise a plurality of nucleic acid probes immobilized on a surface or substrate. The different nucleic acid probes are complementary to, and therefore can hybridize to, different target nucleic acid molecules in a sample. Thus, each probe can be used to simultaneously detect the presence and quantity of a plurality of different genes, e.g., the presence and abundance of different mRNA molecules, or of nucleic acid molecules derived therefrom (for example, cDNA or cRNA).

The arrays are preferably reproducible, allowing multiple copies of a given array to be produced and the results from each easily compared to one another. Preferably microarrays are small, and made from materials that are stable under binding conditions. A given binding site or unique set of binding sites in the microarray will specifically bind to the target. It will be appreciated that when cDNA complementary to the RNA of a cell is made and hybridized to a microarray under suitable conditions, the level or degree of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding a nucleic acid product of the gene) that is not transcribed in the cell will have little or no signal, while a gene for which mRNA is highly prevalent will have a relatively strong signal.

By way of example, GeneChip® (Affymetrix, Santa Clara, Calif.), generates data for the assessment of gene expression profiles and other biological assays. Oligonucleotide expression arrays simultaneously and quantitatively "interrogate" thousands of mRNA transcripts. Each transcript can be represented on a probe array by multiple probe pairs to differentiate among closely related members of gene families. Each probe contains millions of copies of a specific oligonucleotide probe, permitting the accurate and sensitive detection of even low-intensity mRNA hybridization patterns. After hybridization data is captured, using a scanner or optical detection systems, software can be used to automatically calculate the intensity values for each probe cell. Probe cell intensities can be used to calculate an average intensity for each gene, which correlates with mRNA abundance levels. Expression data can be quickly sorted based on any analysis parameter and displayed in a variety of graphical formats for any selected subset of genes.

Screening and diagnostic method of the current invention may involve the amplification of the target loci. A preferred method for target amplification of nucleic acid sequences is using polymerases, in particular polymerase chain reaction (PCR). PCR or other polymerase-driven amplification methods obtain millions of copies of the relevant nucleic acid sequences which then can be used as substrates for probes or sequenced or used in other assays.

Amplification using polymerase chain reaction is particularly useful in the embodiments of the current invention. PCR is a rapid and versatile in vitro method for amplifying defined target DNA sequences present within a source of DNA. Usually, the method is designed to permit selective amplification of a specific target DNA sequence(s) within a heterogeneous collection of DNA sequences (e.g. total genomic DNA or a complex cDNA population). To permit such selective amplification, some prior DNA sequence information from the target sequences is required. This information is used to design two oligonucleotide primers (amplimers) which are specific for the target sequence and which are often about 15-25 nucleotides long.

Mutation detection using the $5'\rightarrow3'$ exonuclease activity of Taq DNA polymerase (TaqMan™ assay) can also be used as a screening and diagnostic method of the current invention. Such an assay involves hybridization of three primers, the third primer being intended to bind just downstream of one of the conventional primers which should be allele-specific. The additional primer carries a blocking group at the 3' terminal nucleotide so that it cannot prime new DNA synthesis and at its 5' end carries a labeled group. In modern versions of the assay, the label is a fluorogenic group and the third primer also carries a quencher group. If the upstream primer which is bound to the same strand is able to prime successfully, Taq DNA polymerase will extend a new DNA strand until it encounters the third primer in which case its $5'\rightarrow3'$ exonuclease will degrade the primer causing release of separate nucleotides containing the dye and the quencher, and an observable increase in fluorescence.

PCR with melting curve analysis can also be used. PCR with melting curve analysis is an extension of PCR where the fluorescence is monitored over time as the temperature changes. Duplexes melt as the temperature increases and the hybridization of both PCR products and probes can be monitored. The temperature-dependent dissociation between two DNA-strands can be measured using a DNA-intercalating fluorophore such as SYBR green, EvaGreen or fluorophore-labelled DNA probes. In the case of SYBR green (which fluoresces 1000-fold more intensely while intercalated in the minor groove of two strands of DNA), the dissociation of the DNA during heating is measurable by the large reduction in fluorescence that results. Alternatively, juxtapositioned probes (one featuring a fluorophore and the other, a suitable quencher) can be used to determine the complementarity of the probe to the target sequence. This technique is sensitive enough to detect single-nucleotide polymorphisms (SNP) and can distinguish between various alleles by virtue of the dissociation patterns produced.

PCR with mass spectrometry uses mass spectrometry to detect the end product. Primer pairs are used and tagged with molecules of known masses, known as MassCodes. If DNA from any of the agent of primer panel is present, it will be amplified. Each amplified product will carry its specific Masscodes. The PCR product is then purified to remove unbound primers, dNTPs, enzyme and other impurities. Finally, the purified PCR products are subject of ultraviolet as the chemical bond with nucleic acid and primers are photolabile. As the Masscodes are liberated from PCR products they are detected with a mass spectrometer.

When a probe is to be used to detect the presence of nucleic acids, the biological sample that is to be analyzed must be treated to extract the nucleic acids. The nucleic acids to be targeted usually need to be at least partially single-stranded in order to form a hybrid with the probe sequence.

It the nucleic acid is single stranded, no denaturation is required. However, if the nucleic acid to be probed is double stranded, denaturation must be performed by any method known in the art.

The nucleic acid to be analyzed and the probe are incubated under conditions which promote stable hybrid formation of the target sequence in the probe and the target sequence in the nucleic acid. The desired stringency of the hybridization will depend on factors such as the uniqueness of the probe in the part of the genome being targeted, and can be altered by washing procedure, temperature, probe length and other conditions known in the art, as set forth in Sambrook et al. 1989.

Labeled probes are used to detect the hybrid, or alternatively, the probe is bound to a ligand which labeled either directly or indirectly. Suitable labels and methods for labeling are known in the art, and include biotin, fluorescence, chemiluminescence, enzymes, and radioactivity.

Assays using such probes include Southern blot analysis. In such an assay, a patient sample is obtained, the DNA processed, denatured, separated on an agarose gel, and transferred to a membrane for hybridization with a probe. Following procedures known in the art (e.g., Sambrook et al. 1989), the blots are hybridized with a labeled probe and a positive band indicates the presence of the target sequence. In this method, the target DNA is digested with one or more restriction endonucleases, size-fractionated by agarose gel electrophoresis, denatured and transferred to a nitrocellulose or nylon membrane for hybridization. Following electrophoresis, the test DNA fragments are denatured in strong alkali. As agarose gels are fragile, and the DNA in them can diffuse within the gel, it is usual to transfer the denatured DNA fragments by blotting on to a durable nitrocellulose or nylon membrane, to which single-stranded DNA binds readily. The individual DNA fragments become immobilized on the membrane at positions which are a faithful record of the size separation achieved by agarose gel electrophoresis. Subsequently, the immobilized single-stranded target DNA sequences are allowed to associate with labeled single-stranded probe DNA. The probe will bind only to related DNA sequences in the target DNA, and their position on the membrane can be related back to the original gel in order to estimate their size.

Northern blots, done in the same fashion, but utilizing RNA, can also be used.

Dot-blot hybridization can also be used to screen for the nucleic acids. Nucleic acid including genomic DNA, cDNA and RNA is obtained from the subject with SLE, denatured and spotted onto a nitrocellulose or nylon membrane and lowed to dry. The membrane is exposed to a solution of labeled single stranded probe sequences and after allowing sufficient time for probe-target heteroduplexes to form, the probe solution is removed and the membrane washed, dried and exposed to an autoradiographic film. A positive spot is an indication of the target sequence in the DNA of the subject and a no spot an indication of the lack of the target sequence in the DNA of the subject.

It would be recognized by a person of skill in the art that a subject who was diagnosed or identified as having either nuclear β-catenin and/or differential expression of the Notch ligands and/or β-catenin target genes, should receive treatment for leukemia or another blood disorder. Such treatment can be those set forth above or more traditional therapies. Additionally, such a patient should be closely monitored.

Kits

It is contemplated that all of the diagnostic and screening assays disclosed herein can be in kit form for use by a health care provider and/or a diagnostic laboratory.

An example of one such kit would contain a marker for nuclear or activated β-catenin, e.g., a labeled antibody, reagents for isolating osteoblasts and performing assays on the isolated osteoblasts, and instructions for use.

Assays for the detection and quantitation of one or more of the Notch ligands and/or β-catenin target genes can be also incorporated into kits. Such kits would include probes for one or more of the genes, reagents for isolating and purifying nucleic acids from biological tissue or bodily fluid, reagents for performing assays on the isolated and purified nucleic acid, instructions for use, and reference values or the means for obtaining reference values in a control sample for the included genes.

A preferred kit for diagnosis and identification of leukemia or a blood disorder would include reagents for both detecting nuclear β-catenin and at least the Notch ligand, Jagged-1.

Drug Screening Assays and Research Tools

The present invention also provides for methods and tools for drug design, testing of agents, and tools for basic research into the causes and etiology of blood cancers and blood disorders.

In one embodiment, proteins and polypeptides in the Wnt signaling pathway, in particular, β-catenin and Notch ligands, can be used in drug screening assays, free in solution, or affixed to a solid support. All of these forms can be used in binding assays to determine if agents being tested form complexes with the peptides, proteins or fragments, or if the agent being tested interferes with the formation of a complex between the peptide or protein and a known ligand.

Thus, the present invention provides for methods and assays for screening agents for prevention and/or treatment of leukemia and/or blood diseases and/or disorders, comprising contacting or incubating the test agent with a β-catenin or Notch ligand polypeptide or protein and detecting the presence of a complex between the polypeptide and the agent or the presence of a complex between the polypeptide and a ligand, by methods known in the art. In such competitive binding assays, the polypeptide or fragment is typically labeled. Free polypeptide is separated form that in the complex, and the amount of free or uncomplexed polypeptide is measured. This measurement indicates the amount of binding of the test agent to the polypeptide or its interference with the binding of the polypeptide to a ligand.

The preferred Notch ligands are JAGGED-1 and DLL-1.

In another embodiment of the present invention, receptors in the Wnt signaling pathway, in particular the receptor that initiates Wnt signaling and the Notch receptor, can be used in drug screening assays, free in solution, or affixed to a solid support. These assays can be used to determine if agents being tested bind to the receptor or interfere with a ligand binding to a receptor.

High throughput screening can also be used to screen for therapeutic agents. Small peptides or molecules can be synthesized and bound to a surface and contacted with the polypeptides encoded by the gene signature transcripts, and washed. The bound peptide is visualized and detected by methods known in the art.

Antibodies to the polypeptides can also be used in competitive drug screening assays. The antibodies compete with the agent being tested for binding to the polypeptides. The antibodies can be used to find agents that have antigenic determinants on the polypeptides, which in turn can be used to develop monoclonal antibodies that target the active sites of the polypeptides.

The invention also provides for polypeptides to be used for rational drug design where structural analogs of biologically active polypeptides can be designed. Such analogs would interfere with the polypeptide in vivo, such as by non-productive binding to target. In this approach the three-dimensional structure of the protein is determined by any method known in the art including but not limited to x-ray crystallography, and computer modeling. Information can also be obtained using the structure of homologous proteins or target-specific antibodies.

Using these techniques, agents can be designed which act as inhibitors or antagonists of the polypeptides, or act as decoys, binding to target molecules non-productively and blocking binding of the active polypeptide.

A further embodiment of the present invention is a method and/or assay for screening and/or identifying a test agent for the prevention and/or treatment of leukemia and/or blood disease and/or disorders comprising is contacting or incubating a test agent with a nucleotide encoding β-catenin or Notch ligands or the Wnt signaling receptor or the Notch receptor, and determining if the test agent binds to the nucleotide, wherein if the test agent binds to the nucleotide, the test agent is identified as a therapeutic or preventative agent for leukemia and/or blood disorders.

A further embodiment of the present invention is gene constructs comprising a nucleic acid encoding β-catenin or the Notch ligands, and a vector. These gene construct can be used for testing of therapeutic agents as well as basic research regarding blood cancers and disorders. These gene constructs can also be used to transform host cells can be transformed by methods known in the art.

The resulting transformed cells can be used for testing for therapeutic agents as well as basic research regarding blood cancers and disorders. Specifically, cells can be transformed with any one of the differentially expressed transcripts, and contacted with a test agent. The resulting expression of the transcript can be detected and compared to the expression of the transcript in the cell before contact with the agent.

The expression of the transcripts in host cells can be detected and measured by any method known in the art, including but not limited to, reporter gene assays.

These gene constructs as well as the host cells transformed with these gene constructs can also be the basis for transgenic animals for testing both as research tools and for therapeutic agents. Such animals would include but are not limited to, nude mice. Phenotypes can be correlated to the genes and looked at in order to determine the genes effect on the animals as well as the change in phenotype after administration or contact with a potential therapeutic agent.

Additionally, animals that have a phenotype of constitutive active β-catenin or increased expression of Notch ligands, can also be used for drug testing and basic research regarding leukemia and other blood disorders. Such an animal can be genetically altered to have the phenotype, or the phenotype can be naturally occurring.

Cells with a constitutive active β-catenin phenotype or increased expression of Notch ligands can also be used for testing both as research tools and for therapeutic agents. These cells would include cells, most preferably osteoblasts, isolated from mice with the MDS or AML phenotype, or humans with MDS or AML.

EXAMPLES

The present invention may be better understood by reference to the following non-limiting examples, which are presented in order to more fully illustrate the preferred embodiments of the invention. They should in no way be construed to limit the broad scope of the invention.

Example 1—General Materials and Methods

Animals

Generation of FoxO1$^{fl/fl}$, a1(I)Collagen-Cre [a$_1$(I)Col-Cre], and Catnb$^{+/lox(ex3)}$ mice has previously been reported (Paik et al., 2007; Dacquin et al., 2002; Harada et al., 1999; Rached et al., 2010a). Catnb$^{+/lox(ex3)}$ mice, express a β-catenin mutant allele in which exon 3, encoding all serine and threonine residues phosphorylated by glycogen synthase kinase 3β (GSK-3β) (Logan and Nusse, 2004), is flanked by loxP sites.

Mice with osteoblast-specific constitute activation of β-catenin were generated by crossing Catnb$^{+/lox(ex3)}$ mice with a$_1$(I)Col-Cre mice expressing Cre under the control of 2.3 kb of the proximal promoter of the mouse pro-a1(I) Collagen gene. The transgene was expressed at high levels in osteoblasts specifically (Rossert et al., 1995). There was in no expression in chondrocytes, condensed mesenchymal cells, perichondrial or periosteal fibroblasts, or any other type I collagen-producing cells, or other fibroblast-rich tissues such as muscle, heart or tendons. The resulting offspring, termed βcat(ex3)$_{osb}$, expressed a constitutive active β-catenin allele in osteoblasts.

Mice with osteoblast-specific deletion of FoxO1 (FoxO1$_{osb}$−/−) were generated by crossing FoxO1$^{fl/fl}$ mice with a$_1$(I)Col-Cre mice. Mice with osteoblast-specific deletion of Jagged-1 were generated by crossing previously described Jagged1$^{fl/fl}$ mice (Kiernan et al., 2006) with a$_1$(I)Col-Cre mice. Genotyping was performed at the weaning stage by PCR analysis of genomic DNA. In each experiment the mice used were of the same genetic background as all of their littermates. Female mice at 1 month of age were used for the bone histomorphometric analysis.

βcat(ex3)osb mice lack teeth due to osteopetrosis and therefore were fed a normal powdered diet that contained all the required nutrients (20% protein, 3.0 ppm Folic Acid, 51 mcg/kg B12 from PicoLab Rodent Diet 20, Cat. Nu. 5053). Folate and B12 levels in their blood were normal (folate greater than 24 ng/ml and B12 greater than 1,000 pg/ml) confirming adequate intake of critical nutrients. Folate and B 12 levels were measured by Antech Diagnostics using a chemiluminescence-based kit (Siemens).

All the protocols and experiments were conducted according to the guidelines of the Institute of Comparative Medicine, Columbia University.

Patient Samples

Bone marrow biopsies from patients with AML and MDS were consecutively obtained from 2000-2008 and reviewed under a research exempt waiver approved by the institutional review board (IRB) of Memorial Sloan Kettering Hospital and Human Biospecimen Utilization Committee. Bone marrow biopsies and aspirates obtained from Columbia University from patients with MDS and AML were stored in IRB-approved Tissue Repository at Columbia University Medical Center after informed consent. This study was conducted under protocol approval from the IRB for use of samples from the Tissue Repository.

Karyotype Analysis

Metaphase chromosome preparations were prepared from cells obtained from spleen specimens from βcat(ex3)$_{osb}$ mice after overnight culture in complete RPMI medium using standard methods. Giemsa banding was performed and the images were captured using Cytovision Imaging system (Applied Imaging, Santa Clara, Calif.) attached to a Nikon Eclipses 600 microscope. Twenty to thirty karyotypes were prepared from each sample and described using the standard chromosome nomenclature for mice.

Array Comparative Genomic Hybridization (aCGH)

aCGH analysis was performed in the spleen of βcat (ex3)$_{osb}$ mice using the Mouse genome CGH 244A Platform (Agilent Technologies) according to the manufacturer's instructions. In brief, spleen DNA from wild type littermates was used as reference DNA. Genomic DNA was subjected to restriction digestion prior to labeling and purification (SureTag DNA labeling kit, Agilent Technologies). For each 244 K array, 2 µg of labeled DNA and 2 µg of germline reference DNA were labelled with Cy5 and Cy3, respectively. Differentially labeled test (tumor) DNA and normal reference DNA were hybridized simultaneously to normal chromosome spreads. Data extraction was conducted using the Agilent feature extraction software. Data files were analyzed using the Agilent DNA analytics software. Data were deposited in Gene Expression Omnibus (Accession Number GSE51690).

Whole-Exome Capture and Massively Parallel Sequencing, Sequence Mapping and Identification of Tumor-Specific Variants For three tumor and three unpaired normal samples, purified genomic DNA (3 µg) was enriched in protein-coding sequences using the SureSelect Mouse All Exon kit (Agilent Technologies) following standard protocols. The resulting target-enriched pool was amplified and subjected to paired-end sequencing (2×100 bp) by using HiSeq2000 sequencing instruments. Exome capture and sequencing procedures were performed at Agilent Technologies. Sequencing reads were mapped to the reference genome mm10 using the Burrows-Wheeler Aligner (BWA) alignment tool version 0.5.9 (Li and Durbin, 2010). Sites that differed from the reference genome (called "variants") were identified and empirical priors constructed for the distribution of variant frequencies in each sample independently. High-credibility intervals (posterior probability ≥1-10-5) for the observed frequency of the variants using the SAVI (Statistical Algorithm for Variant Identification) algorithm (Tiacci et al., 2011) were obtained.

Variants were considered absent if found with a frequency between 0 and 2%, and were considered present if detected with a frequency above 15%, A 15% cut-off was chosen given its correspondence with the sensitivity threshold of direct Sanger sequencing. Variant total depth was required to be greater than 10× and less than 300×. Segmenting variants that exist in one case only and absent in the other five cases identified regions of possible copy number aberrations. The variants found in these regions were removed and all silent variants and those present in dbSNP database were excluded, and only substitution mutations were focused on. Finally, in the tumor samples, all variants found present in any of the normal samples were removed.

The mutations were subjected to validation (present in tumor, absent in normal) by conventional Sanger-based re-sequencing analysis of PCR products obtained from tumor DNA using primers specific for the exon encompassing the variant. Data were deposited in Short Read Archive (Accession Number SRP031981).

Microarray

Total RNA was extracted from primary osteoblasts isolated from mouse calvaria using Trizol reagent (Invitrogen). Microarray analysis was performed using the GeneChip 3' IVT Express kit and mouse genome 430 2.0 array gene chips (Affymetrix) according to the manufacturer's instructions. In brief aRNA was synthesized from 500 ng of RNA and was biotinylated followed by purification and fragmentation using the GeneChip 3' IVT Express kit. Fragmented aRNA was hybridized to Affymetrix mouse genome 430 2.0 array gene chips. Following hybridization chips were scanned with a Genechip Scanner 3000 7G (Affymetrix). Data were normalized using the Mas5 method (Hubbell et al., 2002), and then log$_2$ transformed. Data were deposited in Gene Expression Omnibus (Accession Number GSE43242) (Barrett et al. 2005). Differential expression was analyzed using the LIMMA (Smyth 2004). Twenty genes which were selected in advance of the analysis were focused upon. Genes considered were either active in AML, amplified according to the CGH results, activate Notch, or whose transcription is induced by Notch. A significance cutoff of a raw p<0.05 was used, as is appropriate for small previously-determined gene sets (Simon et al., 2003). Representative probesets of genes whose expression changed greater than ±20% in at least one of the 2 mutants relative to wild type appear in Table 1.

TABLE 1

Representative Probesets of Genes

| Patient ID | Diagnosis | Cytogenetics | β-catenin nuclear localization (% Nuclear) | Age (years) |
|---|---|---|---|---|
| 1 | AML | 45, XX, add(2)(p13), add(3)(q26.2), [g]/45, idem, add(7)(46, XX [20] | Y (25%) | 82 |
| 2 | AML | 47, XY, +8[10]/46, XY[10] | Y (38%) | 70 |
| 3 | AML | 46, XY[20] | Y (27%) | 72 |
| 4 | AML | 42-43, XY, del(1)(q11), −3, del(5)(p13), −6, −7, −8, add(9)(p22), −12, −17, −18, | Y (14%) | 48 |
| 5 | AML | 46, XY, t(2; 8)(q37; q22) two copies of chromosome 16q22 | Y (26%) | 66 |
| 6 | AML | 47, XY, add(5)(p13), +13 [2] 46, XY, add(5)(p13) [14] | Y (33%) | 57 |
| 7 | AML | Add (5p), trisomy 13 | Y (25%) | 44 |
| 8 | AML | NL | Y (30%) | 49 |
| 9 | AML | 46, XX{20} | Y (80%) | 68 |
| 10 | AML | NL | Y (37%) | 64 |
| 11 | AML | NL | Y (46%) | 62 |
| 12 | AML | NL | Y (35% | 69 |
| 13 | AML | NL | Y (25%) | 62 |
| 14 | AML from MDS | 47, XY, del(7)(q22), +21 [11] | Y (17%) | 73 |

TABLE 1-continued

Representative Probesets of Genes

| Patient ID | Diagnosis | Cytogenetics | β-catenin nuclear localization (% Nuclear) | Age (years) |
|---|---|---|---|---|
| 15 | AML from MDS | 47, XY, +8 [12] | Y (32%) | 73 |
| 16 | AML from MDS | 46, XY, del(5)(q13q31), del(20)(q11.2q12) | Y (30%) | 74 |
| 17 | AML from MDS | 46-49, XY, +1, del(5)(q15q31), del(7)(q22q32), +6, +8 | Y (24%) | 60 |
| 18 | AML from MDS | 44-45, XX, −1, −2, t(3; 4)(p21; q35), del(5)(q15q31), hsr(6)(p25), −7, del(13)(q21), −15, −16, +1 | Y (34%) | 64 |
| 19 | AML from MDS | 45, XX, del(5)(q13q33), −20; Monosomy 5, 7, 17 FISH | Y (28%) | 57 |
| 20 | AML from MDS | 46, XY[20] | Y (27%) | 70 |
| 21 | AML from MDS | monosomy 7 FISH Only; Karyotype NL | Y (34%) | 63 |
| 22 | AML from MDS | 46, XX, ?t(2; 17)(q31; q25), del(7)(q32), inc.[cp3] | Y (100%) | 66 |
| 23 | AML from MDS | 46, XY[20] | Y (25%) | 69 |
| 24 | AML from MDS | 47, XX, +8[3]/46, XX[17] | Y (75%) | 79 |
| 25 | AML from MDS | 46, XY[20] | Y (33%) | 78 |
| 26 | RAEB-2 | 46, XX, del(5)(q13q35) [16] | Y (26%) | 67 |
| 27 | RAEB-2 | 46, X, add(X)(q28), −5, del(6)(q13), −7, +8, add(19)(p13) | Y (16%) | 64 |
| 28 | RAEB-2 | 47, XY, +mar?c[20] | Y (20%) | 65 |
| 29 | RAEB-2 | 46, XY[20] | Y (255) | 67 |
| 30 | RAEB-2 | 46, XY, del(20)(q11.2q13.3)[4] | Y (50%) | 73 |
| 31 | RAEB-1 | 46, XY[20] | Y (23%) | 77 |
| 32 | RAEB-1 | 46, X, idic(X)(q13)[12]/47, IDEM, +idic(X)(q13)[3]/45] | Y (33%) | 77 |
| 33 | RAEB-1 | — | Y (20%) | 76 |
| 34 | RCMD | 46, XX, t(3: 3)(q21; q26.3){19}/46, XX{1} | Y (23%) | 64 |
| 35 | RARS | 46, XY[20] | Y (11%) | 76 |
| 36 | RARS | NL | Y (25% | 57 |
| 37 | RCMD | Not available | Y (18%) | 75 |
| 38 | RCMD | 46, XY, t(7; 17)(q22; p13)[18]/48, idem, +1, −2, −4, −8, −10, −1 | Y (23%) | 70 |
| 39 | RCMD | 46, XY, del(11)(q14q23)[16]/46, idem, del(20)(q11.2q1) | Y (25%) | 74 |
| 40 | RCMD | NL | Y (20%) | 67 |
| 41 | RCMD | FISH: 1p36; del(7q); loss of p53; Karyotype NE | Y (16%) | 76 |
| 42 | AML | NL | N | 49 |
| 43 | AML | NL | N | 71 |
| 44 | AML | NL | N | 49 |
| 45 | AML | complex54-57, X, add(X)(q28), +X, +1, −4, add(4)(p15), del(4)(q21), add(5)(p15), del(5)(q13q33), del(6)(q21q25), del(7)(q22), inv(7)(q22), +8, add(9)(p22), +11x2, del(12)(q12), add(12)(p13), −13, +14x2, −18, +19, +20, +21, +22 | N | 64 |
| 46 | AML | 47, XX, t(2; 7)(q13; q22), t(9; 11)(p22; q23), +19 | N | 60 |
| 47 | AML | 46, XX, del(7)(q11.2), ?del(10)(p11.2) | N | 61 |
| 48 | AML | 46, XX, del(7)(q22q32) | N | 75 |
| 49 | AML | 46, XX, ?t(11; 19)(q23; p13.1) | N | 61 |
| 50 | AML | 46, XX, del(13q)(q12q14), del(20)(q11.2) | N | 60 |
| 51 | AML | 50, XX, +2, ins(3; ?)(q21; ?)x2, del(5)(q23q31), +6, +8, +10, amp(11)(q23), +del(13)(q12q14), −18 | N | 71 |
| 52 | AML | 40-42, XY, dup(1)(p13p22), −3, −4, −5, del(6)(q21q25), −7, t(9; 11)(q13; p13), +11, −13, −16, Add(17)(p13), −22 | N | 64 |
| 53 | AML | Normal Karyotype; FISH del(7q) 4.6% | N | 59 |
| 54 | AML | trisomy c-13 71% | N | 71 |
| 55 | AML | 48, XY, +9, +13; FISH: extra copy of 9 - 40% | N | 79 |
| 56 | AML | 46, XY, del(9)(q13q22) | N | 50 |
| 57 | AML | NL | N | 31 |
| 58 | AML | NL | N | 72 |
| 59 | AML | NE | N | 24 |
| 60 | AML | t(1q32; 4q21) | N | 34 |
| 61 | AML | trisomy (8, 14, 16, 18) | N | 37 |
| 62 | AML | NL | N | 68 |
| 63 | AML | NL | N | 41 |
| 64 | AML | NL | N | 62 |
| 65 | AML from MDS | 47, XY, +8 | N | 73 |
| 66 | AML from MDS | NL | N | 51 |
| 67 | AML from MDS | Karyotype NE; FISH; 5q deletion in 65% | N | 47 |

TABLE 1-continued

Representative Probesets of Genes

| Patient ID | Diagnosis | Cytogenetics | β-catenin nuclear localization (% Nuclear) | Age (years) |
|---|---|---|---|---|
| 68 | AML from MDS | 51-60, XY, +Y, +1, +2, +2, −2, −4, +5, del(5)(q13q31), +6, +7, del(7)(q22), +8, −9, −10, i(11)(q10), −12, +13, +14, −15, −17, −21, +22 | N | 42 |
| 69 | AML from MDS | NL | N | 74 |
| 70 | AML from MDS | Karyotype NE; FISH: del(7q) in 3% | N | 67 |
| 71 | AML from MDS | Karyotype NE; FISH del(7q) in 7.6% and trisomy 11 in 40% of cells | N | 64 |
| 72 | AML from MDS | NE | N | 65 |
| 73 | AML from MDS | 46, XX, del(11)(q23), der(17)t(3; 17)(p21; p11); FISH: del 7q in 69% and deletion of 11q23 in 7% of interphase cells | N | 67 |
| 74 | AML from MDS | 46, XY[20] | N | 74 |
| 75 | AML from MDS | 46, XY[20] | N | 69 |
| 76 | AML from MDS | 46, XY, del(4)(q21q27), add(5)(q15), −7, −11, +r1, +r2[18] | N | 90 |
| 77 | AML from MDS | 46, XY{20} | N | 70 |
| 78 | AML from MDS | — | N | 76 |
| 79 | RAEB-2 | Karyotype NE; FISH, monosomy of chromosome 7 in 13.33% | N | 36 |
| 80 | RAEB-2 | NL | N | 71 |
| 81 | RAEB-2 | NL | N | 86 |
| 82 | RAEB-2 | 46, XY, add(17)q11.2), add(21)q11.2), add(21)(q22) | N | 77 |
| 83 | RAEB-2 | 45, XY, del(5)(q13q35), der(10)inv(10)(p11.2q22)t (10) | N | 80 |
| 84 | RAEB-2 | 46, XY[20] | N | 63 |
| 85 | RAEB-2 | 46, XY, del(14)(q32){15]/46, XY{5} | N | 62 |
| 86 | RAEB-2 | 45, XX, −7{2}/46, XX, −7, t(12; 18)(p13; q21), +mar{2}/46 | N | 61 |
| 87 | RAEB-2 | 46, Y, del(X)(q24), −7, +8, dup(11)(q13q24.2), add(18) (p | N | 72 |
| 88 | RAEB-2 | 47, XX, +8[6]/46, XX[14] | N | 67 |
| 89 | RAEB-2 | NL | N | 67 |
| 90 | RAEB-2 | Karyotype NE; FISH: 5q deletion in 54% | N | 71 |
| 91 | RAEB-1 | 45, XY, −7[4]/46, IDEM, +MAR[16] | N | 76 |
| 92 | RAEB-1 | 46, XX, del(5)(q13q33)[7]/46, XX[13] | N | 81 |
| 93 | RAEB-1 | 46, XY{20} | N | 73 |
| 94 | RAEB-1 | 47, XY, +8 | N | 68 |
| 95 | RAEB-1 | 45, XY, −7 | N | 60 |
| 96 | RAEB-1 | Del (5q), del(7q), +8, and i(11q) | N | 42 |
| 97 | RAEB-1 | NE | N | 78 |
| 98 | RARS | 47, XY, +8 [4]/47, idem, del(13)(q12q14)[12]/46, XY[4] | N | 75 |
| 99 | RCMD | 46, XY[20] | N | 73 |
| 100 | RCMD | 46, XY[20] | N | 68 |
| 101 | RCMD | 45, X, −Y[15]/46, XY[5] | N | 81 |
| 102 | RCMD | 47, XX, +8[6]/46, XX[14] | N | 77 |
| 103 | RCMD | NL | N | 40 |
| 104 | RCMD | NL | N | 70 |
| 105 | RCMD | ND | N | 46 |
| 106 | RCMD | NL | N | 75 |
| 107 | RCUD | 47, XY, der(7)t(1; 7)(q10; p10), +8 | N | 77 |

Bone Marrow Transplantation

For bone marrow transplantations, adult, wild type B5.SJL (CD45.1) recipient mice (8 weeks of age) were lethally irradiated (10 Gy, split dose) and were then transplanted with $1 \times 10^5$ of total bone marrow cells from βcat (ex3)$_{osb}$ (CD45.2) mice (4 weeks of age) by retro-orbital venous plexus injection. Engraftment efficiency in recipients was monitored by donor contribution of CD45.2+ cells using FACS analysis. For reverse experiment, because of the early lethality of βcat(ex3)$_{osb}$ mice, $1 \times 10^5$ of total bone marrow cells from wild type B6.SJL (CD45.1) mice were transplanted into lethally irradiated (600 rads, split dose) new born (P1) β cat(ex3)$_{osb}$ mice or wild type littermates by fetal liver injections. Engraftment efficiency in recipients was monitored by donor contribution of CD45.1+ cells using FACS analysis. For HSC and progenitor transplantation studies, sublethally (5.5 Gy) irradiated wild type B5.SJL (CD45.1) recipient mice (8 weeks of age) were injected with fractionated donor bone marrow subsets isolated from βcat (ex3)$_{osb}$ (CD45.2) or wild type B5.SJL (CD45.2) mice (4 weeks of age). Engraftment efficiency in recipients was monitored by donor contribution of CD45.2+ cells using FACS analysis.

Treatment of Animals with γ-Secretase Inhibitor

Mice were treated with vehicle, the γ-secretase inhibitor DBZ ((2S)-2-[2-(3,5-difluorophenyl)-acetylamino]-N-(5-methyl-6-oxo-6,7-dihydro-5H-dibenzo[b,-d]azepin-7-yl)-propionamide, 5 µmol/kg) daily by intraperitoneal injection for 10 days. DBZ is cell-permeable, selective, nontransition sate and noncompetitive inhibitor of the γ-secretase complex. DBZ was synthesized to greater than 99.9% purity as assessed by LC/MS (Syncom) and suspended in a 0.5%

Methocel E4M (wt/vol, Colorcon) and 0.1% (vol/vol) Tween-80 (Sigma) solution (van Es et al., 2005). Immediately before intraperitoneal injection, DBZ was sonicated for 2 minutes to achieve a homogenous suspension.

Hematological Measurements and Peripheral Blood Morphology

For hematological measurements, blood was collected by cardiac puncture. Peripheral blood cell counts were performed on a FORCYTE Hematology Analyzer (Oxford Science Inc.). For morphological assessment, peripheral blood smears were stained with Wright-Giemsa stain (Sigma-Aldrich) for 10 minutes followed by rinsing in $dH_2O$ for 3 minutes. Images were taken using a 60× objective on a Leica microscope outfitted with camera.

Real-Time PCR

Total RNA was isolated from LSK or hematopoietic cells using RNAeasy micro Plus kit (Quiagen). Total RNA from long bones was isolated using TRIzol reagent. Quantitative real-time PCR was performed using the SYBR Green Master Mix (Bio-Rad) as previously described (Rached et al., 2010a). β-Actin was used as endogenous control. Gene expression in LT-HSCs, ST-HSCs and MPPs was performed using the Power Syber Green Cells-to-CT kit (Ambion Life Technologies)

Reporter Constructs and Luciferase Assays

Mouse FoxO1 and β-catenin expression constructs were transfected in OB-6 osteoblastic cells. The Jagged-1 promoter region carries multiple potential TCF/LEF binding sites (C/TCTTTG) located up to nucleotide −4075 (4075, −3072, −2626, −2578, −2343, −1992, 1957, −1566, −1221, −782). The mouse reporter constructs −4112/+130 and −2100/+130 for Jagged-1-luc were generated by PCR amplification of the corresponding fragments using mouse genomic DNA as template and subsequent subcloning into the BglII and KpnI-BglII sites of the pGL3Basic vector (Promega), respectively. Transient transfection assays were performed in HEK293T using Lipofectamine 2000 (Invitrogen) according to the manufacturer's instructions. Cells were seeded in 24 well plates at a density of $0.3 \times 10^5$ cells/well. 24 hours later, cells were transfected with a total amount of 350 ng of DNA containing 150 ng reporter plasmid and 50 ng Foxo1 and/or β-catenin and TCF-1 expression vectors. 5 ng of pRL-CMV Renilla (Promega) was used as an internal control to normalize for transfection efficiency and equivalent amounts of DNA were achieved with pcDNA3 vector. Forty hours after transfection luciferase activity was determined using the Dual Luciferase Reporter Assay System (Promega) and quantified using Fluostar Omega (BMG Labtech Inc). Luciferase activity is presented as fold induction over basal conditions normalized to empty luciferase vector for identical experimental conditions.

Chromatin Immunoprecipitation (ChIP) Assay

Primary osteoblasts were seeded in 10 cm dishes at a density of $5 \times 10^6$. Cells were cross-linked with 1% formaldehyde for 10 minutes. Following Dounce homogenization, nuclei were collected and sonicated on ice to an average length of 0.5 kb. The samples were centrifuged and pre-cleared with protein G in the presence of sonicated λDNA and bovine serum albumin for 2 hours at 4° C. One-tenth of the volume of supernatant was used as input, and the remaining volume was immunoprecipitated with β-catenin antibody and the immune complexes were collected by absorption to protein G-sepharose, washed, eluted from the beads and incubated for 5 hours at 65° C. to reverse cross-links. After treatment with proteinase K, DNA was extracted with phenol-chloroform and precipitated with ethanol. Immunoprecipitated chromatin was analyzed by PCR using primers corresponding to TCF/LEF binding sites on the Jagged-1 promoter (−4075, −3072, −2626, −2578, −2343, −1992, −1957, −1566, −1221, −782). Putative binding elements were identified by using the TRANSFAC database. The products of the PCR amplifications were analyzed by agarose gel electrophoresis.

Antibodies and Flow Cytometry Analysis

Freshly isolated bone marrow cells and spleen cells were resuspended in flow-staining buffer (PBS plus 2% FBS) and the primary conjugated antibodies were added. After 30 minutes incubation at 4° C., the cells were then washed twice before flow cytometry analysis. The following monoclonal antibodies conjugated with fluorescein isothiocyanate (FITC), Allophycocyanin (APC) phycoerythrin (PE), PE-Cy7, APC-CY7, Pacific Blue, and Alexa 700 were used: CD117 (c-kit; 2B8), Sca-1 (D7), Mac-1α (M1/70), Gr-1 (RB6-8C5), TER-119, (Ly-76) B220 (CD45R), CD19 (ID3), IgM (R6-60.2), CD3 (17A2), CD4 (RM4-5), CD8a (53-6.7), CD34 (RAM34), CD45 (30-F11), CD31 (MEC 13.3), CD16/CD32 (FcγRII/III; 2.4G2), CD135 (A2F10.1), CD150 (9D1), CD71 (C2), CD45.2 (104), CD45.1 (A20), F4/80, non-phospho (Active) β-Catenin (S33/S37/T41) antibody, IL-7Rα (SB199), Jagged-1 (C-20) and (Cell Signaling; D13A1). Seven-color flow cytometry acquisition was performed using a LSR II flow cytometer (Becton Dickinson) and analysis using FLO-JO software (Treestar, Inc). Cells were gated for size, shape and granularity using forward and side scatter parameters. The positive populations were identified as cells that expressed specific levels of fluorescence activity above the nonspecific auto fluorescence of the isotype control. Nonspecific binding was reduced by preincubation with unconjugated (2.4G2). Osteoblasts from MDS/AML patients or healthy subjects were identified as CD34−/Lin−OCN+ cells, (OCN: osteocalcin an osteoblast-specific protein used for isolation of live osteoblastic cells). For Flow sorting bone marrow, spleen and thymus cells were resuspended in flow staining buffer at $1 \times 10^6$/ml and labeled with the appropriate conjugated antibodies. After 30 minutes incubation, cells were washed twice using flow buffer. Flow sorting was performed using FACSAria (Becton Dickinson). Sorted populations were subsequently cultured or stored in RLT buffer at −80° C. for later extraction of RNA. Fluorescence intensity plots were presented in log scale. All flow cytometry data were representative of five independent experiments.

Clonogenic Assay

Bone marrow cells from 4-week old βcat(ex3)osb or wild type mice were cultured in DMEMα with 10% FBS in the presence of 10 ng/ml of GM-CSF or M-CSF or G-CSF for 7 days. An aliquot of the cells was used to prepare Cytospins and stained with Giemsa to identify blasts. A second aliquot was analyzed by flow cytometry for expression of F4/80, CD11b and Gr1.

Isolation and Counting of Osteoblasts from Murine and Human Bone

The periosteal layer was removed from murine tibia and femurs, the remaining bone was crushed and washed to remove the bone marrow and bone pieces were digested with Collagenase III. Osteopetrosis in βcat(ex3)$_{osb}$ mice does not allow the use of only endosteal bone from due to dispersion in the marrow space of irregular trabecular units.

Human bone biopsies were dissected into pieces and fat and clot was removed from bone chips and a 3 mm section was transferred into 500 ul alpha-MEM+ 1% Pen/Strep. Scissors were used to cut the bone chip into a slurry and then the slurry was digested in 500 uL FBS-free AMEM (+PS) +4 mg/mL collagenase type III (Worthington) for final concentration of 2 mg/mL. After incubation for 1 hour with intermittent vortexing, slurry was frozen live for later use in 90% FBS+10% DMSO, or cultured in a 6-well plate containing 4 mL AMEM+20% FBS+PS (5 mL final volume) for human bone cultures.

For flow cytometry analysis, osteoblasts were identified from the digested bone samples as a population of CD34⁻Lin⁻Ocn⁺ cells, where OCN (osteocalcin) is an osteoblast-specific, non-nuclear protein commonly used for isolation of live osteoblastic cells (Eghbali-Fatourechi et al., 2005; Rubin et al., 2011; Manavalan et al., 2012). For experiments in mice, all gene expression studies were repeated using calvaria-derived cells a population rich in committed osteoblast progenitors and routinely used as osteoblast-representative. Primary murine osteoblasts were prepared from calvaria of 2 day-old pups as previously described (Ghosh-Choudhury et al., 1994; Rached et al., 2010b). Mice calvaria were sequentially digested for 20, 40, and 90 minutes at 37° C. in a modified minimal essential medium (GIBCO)–10% FBS containing 0.1 mg of collagenase P (Worthington) per ml and 0.25% trypsin (Gibco). Cells of the first two digests were discarded, whereas cells released from the third digestion were plated in a minimal essential medium–10% FBS.

Osteoblasts were counted in each human bone biopsy as defined by standard histomorphometry guidelines (Parfitt et al., 1987; Parfitt, 1983; Recker et al., 2011). The number of osteoblasts per mm of bone surface was calculated. The number of osteoblasts counted depends on the size of the sample and the bio-/pathophysiological characteristics of the individual, and for this study, the size of the biopsy (1 cm) allowed for counting of 30 osteoblasts per biopsy.

Histological Analysis of Human Biopsies and Murine Bone, Spleen and Liver

Bone marrow biopsies were fixed overnight in 10% neutral formalin solution, decalcified embedded in paraffin and sectioned at 5 μm per standard laboratory protocol. Sections were stained for β-catenin using a monoclonal antibody (1:1000, BD Transduction Lab) or for Runx2 using a polyclonal antibody (1:100 dilution, Santa Cruz) on an automated Ventana Discovery XT (Tuscon, Ariz.) platform according to manufacturer's instructions. Immune complexes formed were developed using a DAB Map Kit (Ventana, Tuscon, Ariz.). Murine long bones, spleen and liver were collected from one month old mice, fixed overnight in 10% neutral formalin solution, embedded in paraffin, sectioned at 5 μm, and stained with haematoxylin and eosin (H&E). For immunohistochemistry, specimens were incubated with CD-117 (C-kit; Abcam), CD13 (Santa Cruz) or Myeloperoxidase (MPO) antibodies after an antigen retrieval step and blocking of endogenous peroxidase with 3% $H_2O_2$. Sections were then incubated with biotinylated secondary antibody and immune complexes formed were detected using standard Avidin Biotin complex method.

Western Blotting and Immunoprecipitation

Bone extracts (60 μg) were analyzed on a SDS-polyacrylamide gel, transferred to a PVDF membrane, and immunoblotted with FoxO1 antibody (Cell Signaling). For immunoprecipitation, 100 μg of cell lysates from primary osteoblasts were incubated with 2 μg of specific antibodies and 20 μl of protein A/G agarose beads (Santa Cruz) overnight at 4° C. on a rotating device followed by immunoblotting.

Bone Histomorphometric Analysis

Histomorphometric analyses were performed as previously described (Rached et al., 2010b). In brief, vertebral column specimens collected from one month old mice were fixed in 10% formalin for 24 hours, dehydrated in graded ethanol series and embedded in methyl methacrylate resin according to standard protocols. Von Kossa/Von Giesson staining was performed using 7-μm sections for bone volume over tissue volume (BV/TV) measurement. For analysis of the parameters of osteoblasts and osteoclasts, 5-μm sections were stained with toluidine blue and tartrate-resistant acid phosphatase, respectively. Histomorphometric analyses were performed using the OsteoMeasure analysis system (OsteoMetrics). Bone formation Rate (BFR) was analyzed by the calcein double labeling method. Calcein (Sigma-Aldrich) was dissolved in calcein buffer (0.15 M NaCl and 2% $NaHCO_3$) and injected twice at 0.125 mg/g body weight on days 1 and 5, and then mice were killed on day 7. 5-μm sections were used for BFR measurements. Images were taken using a 10× objective on a Leica microscope outfitted with camera. Ten animals were analyzed for each group.

Statistical Analysis

All data are represented as mean±standard deviation. Statistical analyses were performed using a one-way ANOVA followed by Student-Newman-Keuls test and a p value less than 0.05 was considered significant. Time-to-event analysis was used to assess medium survival time to death. Kaplan-Meier curves were generated to illustrate time to death, stratified by group status. Statistical significance of the between-group difference in the median time-to-endpoint was assessed by the log-rank test. Statistical analyses were performed using XLSTAT (2012.6.02, Addinsoft) and SAS (version 9.2; SAS institute, Inc, Cary N.C.). A p value less than 0.05 was considered statistically significant.

Example 2—Activation of β-Catenin in Osteoblasts Causes Hematopoietic Dysfuntion Using mice that express a constitutive active β-catenin allele in their osteoblasts, it was shown that this β-catenin activation causes hematopoietic dysfunction.

Materials and Methods

Mice that express a constitutive active β-catenin allele in their osteoblasts termed βcat(ex3)$_{osb}$ have been described previously by Glass et al. (2005) and are described in Example 1. These mice have an osteopetrotic phenotype because of a decrease in osteoclast numbers and die before 6 weeks of age (FIG. 1).

Hematological measurements, peripheral blood morphology, flow cytometry, PCR, and histological analysis were performed as described in Example 1.

Results

Figures 3B, 3C:
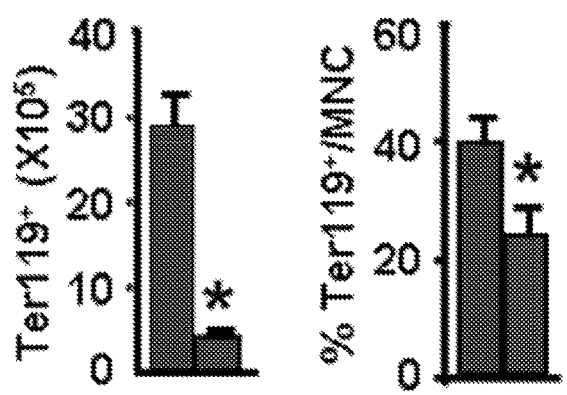
Figure 4A:
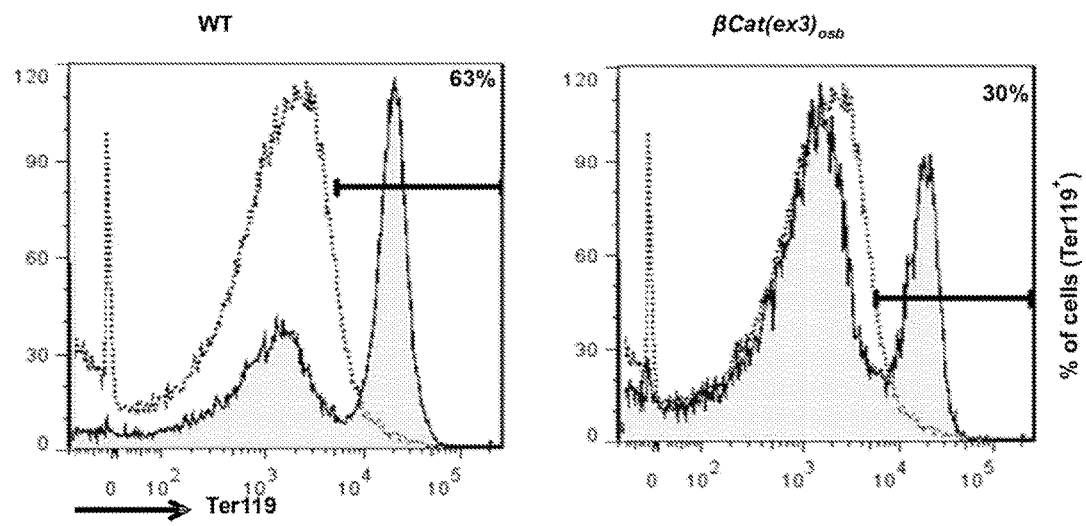
FIG. 4 depicts a representative flow cytometry analysis image (FIG. 4A) and numbers (FIG. 4B) of Ter119+ cells in the spleen of βCat(ex3)$_{osb}$ mice as compared to wild type. In the graph, the wild type group is represented by the left hand bar, and the βcat(ex3)$_{osb}$ mice group the right hand bar, n=6 mice per group. *p<0.05 versus WT. Results are mean±SD.
Figure 4B:
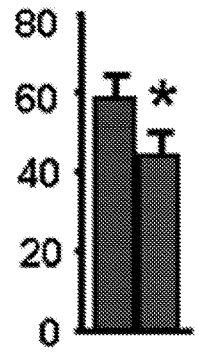
Figures 5A, 5B, 5C, 5D:
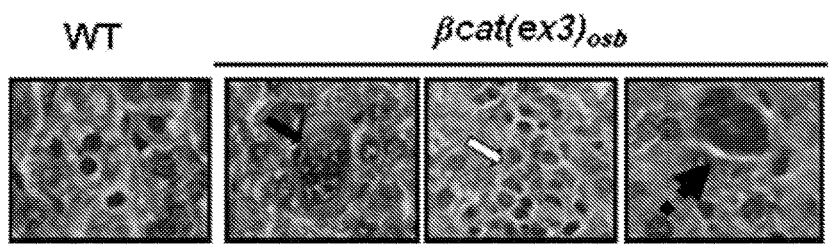
FIG. 5 shows liver sections of wild type (FIG. 5A) and βCat(ex3)$_{osb}$ mice (FIGS. 5B-D). Images taken at 60× show megakaryocytes (FIG. 5B with solid black arrow), myeloid (FIG. 5C with solid white arrow), and rare erythroid precursors (FIG. 5D with dotted arrow).
Figure 6A:
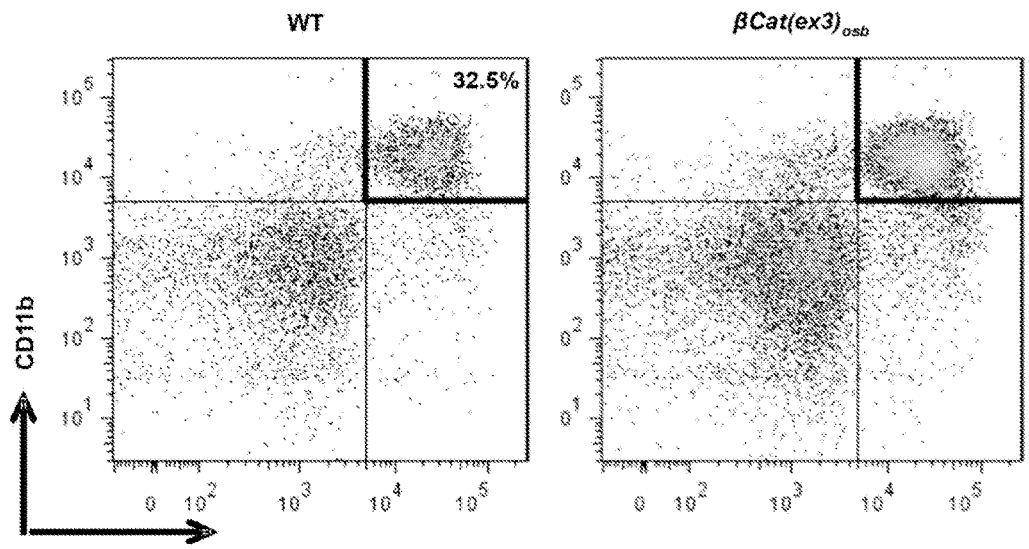
FIG. 6 shows a representative flow cytometry analysis image (FIG. 6A), numbers (FIG. 6B), and percentages (FIG. 6C) of CD11b+/Gr1+ cells in the bone marrow of βCat(ex3)$_{osb}$ mice.
FIG. 6D shows a representative flow cytometry analysis image and FIG. 6E the percentage of CD11b+/Gr1+ cells in the spleen of βCat(ex3)$_{osb}$ mice. In every graph, the wild type group is represented by the left hand bar, and the βcat(ex3)$_{osb}$ mice group the right hand bar. n=6 mice per group. *p<0.05 versus WT. Results are mean±SD.
Figures 6B, 6C:
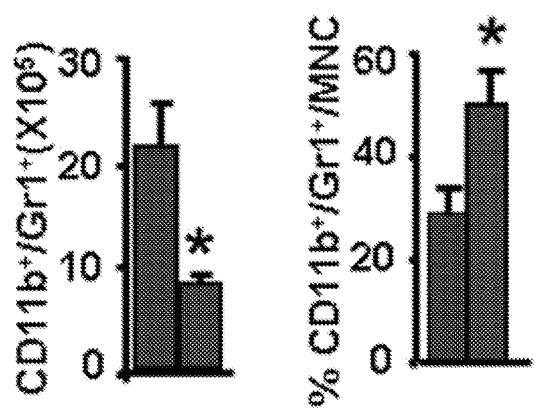
Figure 6D:
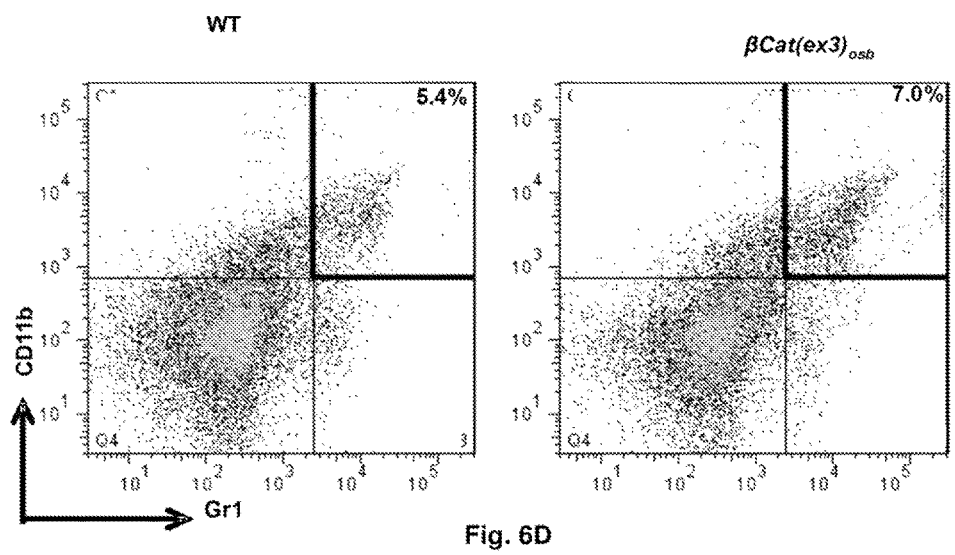
Figure 6E:
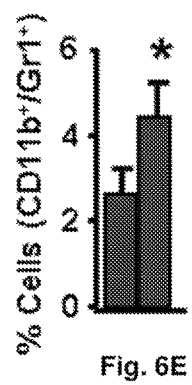

At 2 weeks of age, βcat(ex3)$_{osb}$ mice were anemic with a red blood cell count of 4.63±0.3×10⁶/μl as compared to a red blood cell count of 7.41±0.9×10⁶/μl in wild type mice (Table 2 and FIG. 2A). βcat(ex3)$_{osb}$ mice also had peripheral blood monocytosis, neutrophilia and lymphocytopenia as seen in Table 2 and FIGS. 2B, 2C, and 2D, and a decrease in erythroid cells in the bone marrow and spleen (FIGS. 3 and 4). Extramedullary hematopoiesis was observed in the liver of these mice as well indicated by megakaryocytes, myeloid, and rare erythroid precursors (FIG. 5).

Figures 7A, 7B, 7C, 7D:
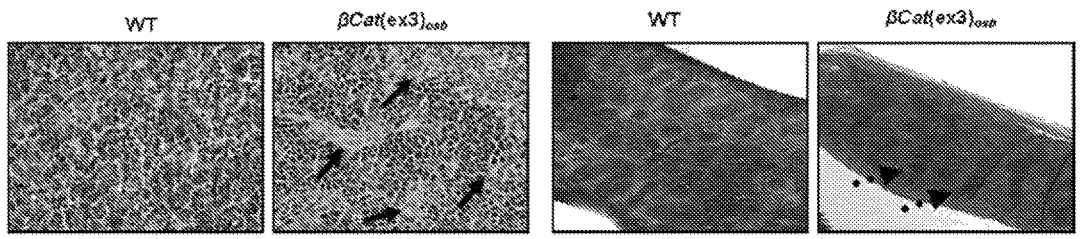
FIGS. 7A and B are 60×, with solid arrows in FIG. 7B indicating red pulp expansion.
FIGS. 7C and D are 10×, with dotted arrows in FIG. 7D indicating coalescence of white pulp, n=6 mice per group. *p<0.05 versus WT. Results are mean±SD.

Partly because of the narrowing of their marrow cavity, total bone marrow cellularity was decreased in βcat(ex3)$_{osb}$ mice (Table 2). Although the number of myeloid (CD11b+/Gr1+) cells decreased in the bone marrow due to compromised marrow cavity, their relative percentage was increased suggesting a shift in the differentiation of HSCs to the myeloid lineage (FIG. 6). Likewise, the percentage of myeloid cells increased in the spleen (FIG. 6). Spleens were also characterized by loss of typical splenic architecture with expansion of red pulp and coalescence of white pulp indicating an increase in extramedullary hematopoiesis in βcat (ex3)$_{osb}$ mice (FIG. 7).

In view of this phenotype, PCR analysis of genomic DNA from osteoblasts, bone marrow hematopoietic cells (CD45+ CD34+CD31+) and spleen of wild type and βCat(ex3)$_{osb}$ mice were used to verify that the mutation was introduced in osteoblasts, but not in any cells of the hematopoietic compartment (FIG. 8). Moreover, quantitative real-time PCR analysis of the expression of the β-catenin target genes Axin2, Tcf1, Tcf3 and Lef1 was not affected in bone marrow hematopoietic cells or in the spleen (FIGS. 9A and 9B) although they were upregulated in the bone of βcat(ex3)$_{osb}$ mice (FIG. 9C).

TABLE 2

Hematopoietic parameters in WT and βCat(ex3)$_{osb}$ mice

| Parameter | Wild type | βcat(ex3)$_{osb}$ mice |
|---|---|---|
| WBC (×10$^3$/µl) | 3.66 ± 0.3 | 1.81 ± 0.2 |
| RBC (×10$^6$/µl) | 7.41 ± 0.9 | 4.63 ± 0.3 |
| HB g/dl | 11.02 ± 1.5 | 6.10 ± 0.8 |
| HCT (%) | 37.94 ± 2.3 | 27.8 ± 2.8 |
| Platelet (10$^3$/µl) | 1217.4 ± 207.7 | 570 ± 54.2 |
| LY (%) | 70.93 ± 4.3 | 21.66 ± 1.5 |
| NE (%) | 21.90 ± 1.9 | 69.07 ± 1.7 |
| MO (%) | 5.50 ± 0.1 | 91.7 ± 0.5 |
| EO (%) | 1.36 ± 1.1 | 0.26 ± 0.2 |
| BA (%) | 0.3 ± 0.25 | 0.12 ± 0.1 |
| BM cell per femur (10$^5$) | 71.7 ± 0.45 | 16.6 ± 0.27 |

White blood cells (WBC), Red blood cells (RBC), Hemoglobin (HB), Hematocrit (HCT), platelets lymphocytes (LY), Monocytes (MO), Eosinophils (EO), Basophils (BA), Bone Marrow (BM) Cells in 2 week old βCat(ex3)$_{osb}$ mice and wild type control littermates Example 3—Further Evidence that Activation of β-Catenin in Osteoblasts Causes Hematopoietic Dysfuntion The extensive hematopoietic abnormalities found in mice expressing the constitutive active β-catenin allele in their osteoblasts suggest the mutation affects multiple HSC lineages.

Materials and Methods

The same materials and methods were used as in Example 2.

Results

Figure 10A:
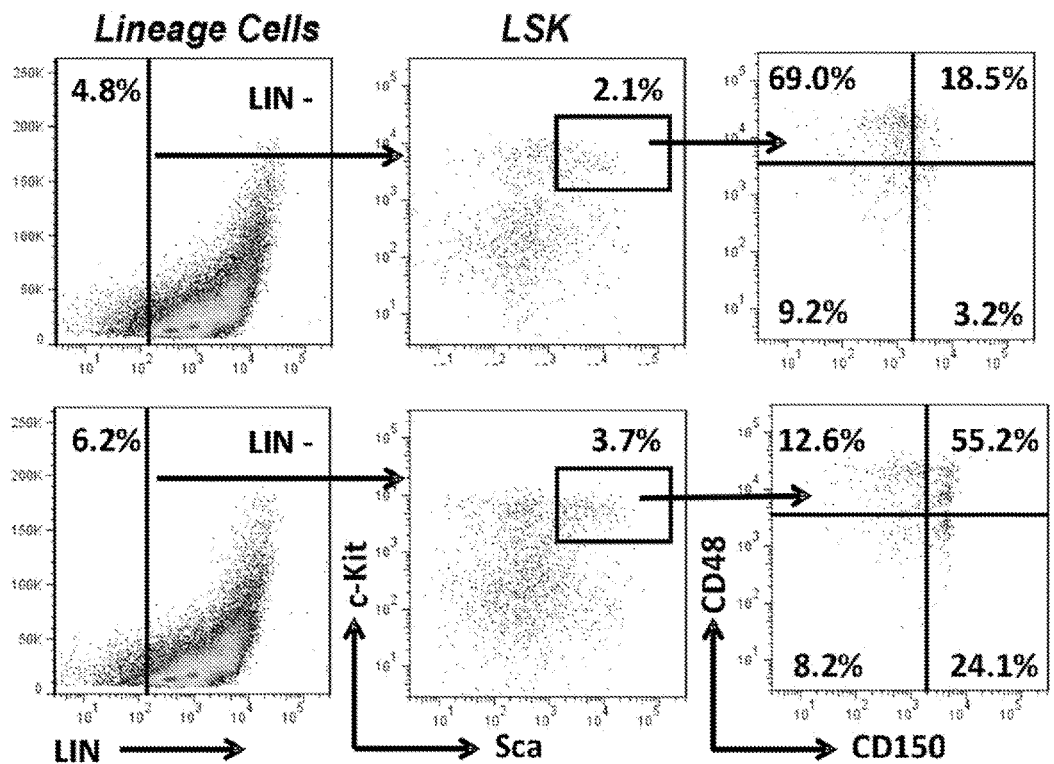
FIG. 10 shows a representative flow cytometry analysis image (FIG. 10A) showing distribution of LSK (Lineage-Sca+C-kit+) population in the bone marrow of WT (top panels) and βCat(ex3)$_{osb}$ mice (bottom panels). Left panel: Lin subsets after lineage-positive cells were electronically gated out; Middle panel: Profiles of LSK population; Right Panel: Distribution of cells in immunophenotypically defined stem cells LSK+/CD150+/CD48− in the bone marrow.
FIG. 10B depicts a graph of numbers of LSK cells.
FIG. 10C shows a graph of percentage of LSK in the bone marrow.
FIG. 10D show frequency, and FIG. 10E percentage of LT-HSCs and ST-HSCs numbers in the bone marrow. In every graph, the wild type group is represented by the left hand bar, and the βcat(ex3)$_{osb}$ mice group the right hand bar. n=6 mice per group. *p<0.05 versus WT. Results are mean±SD.
Figure 10B:
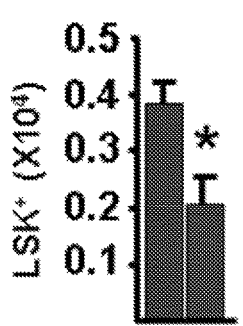
Figure 10C:
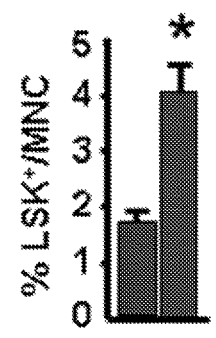
Figure 10D:
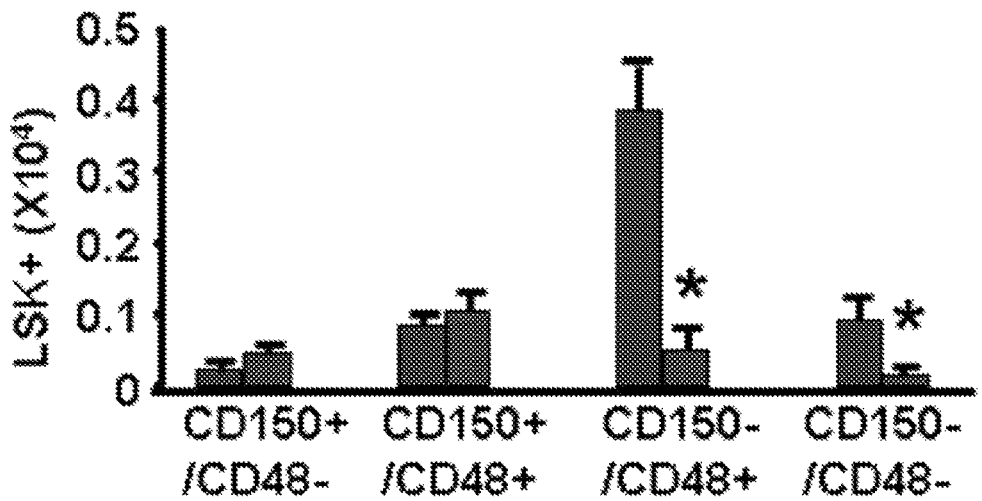
Figure 10E:
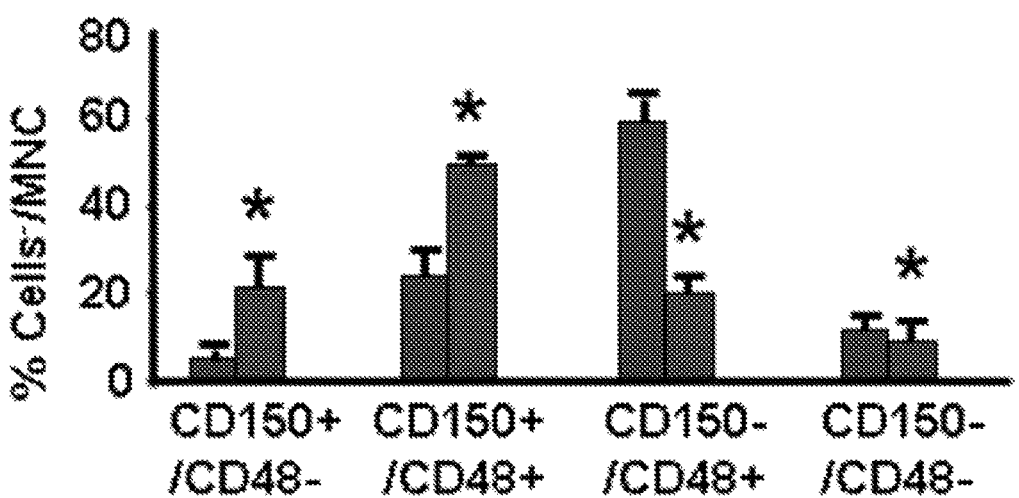
Figure 11:
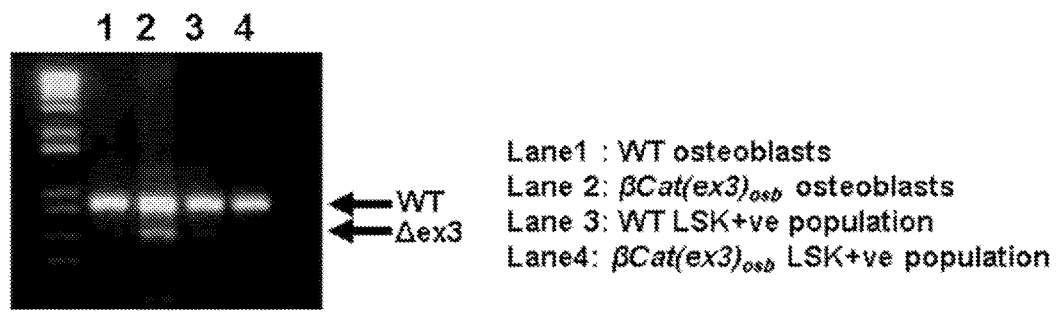
FIG. 11 shows PCR analysis of genomic DNA from osteoblasts and sorted LSK+ population of WT and βCat (ex3)$_{osb}$ mice.
Figure 12A:
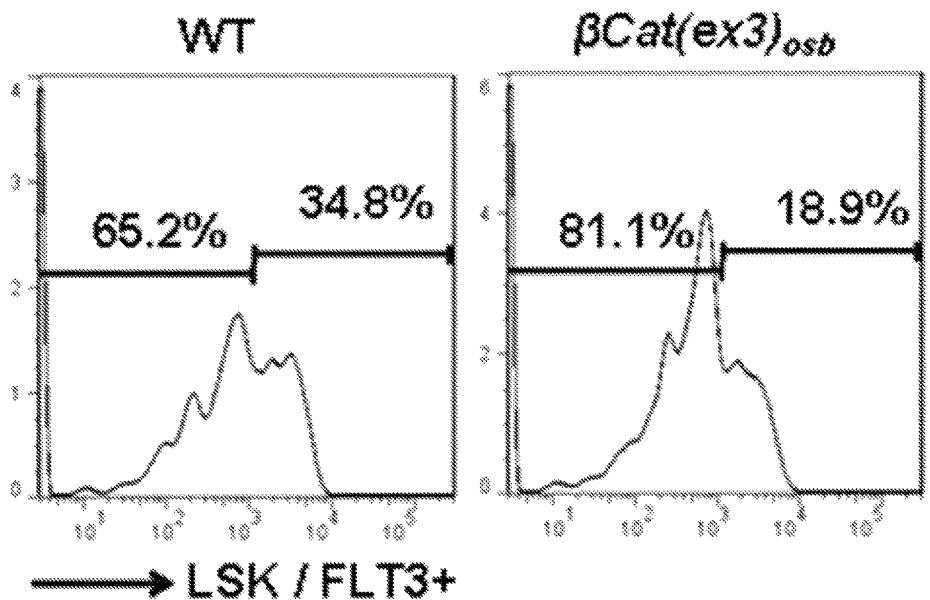
FIG. 12 shows representative flow cytometry analysis (FIG. 12A), numbers of (FIG. 12B), and percentage of (FIG. 12C) LSK+/FLT3+ cells in the bone marrow. In every graph, the wild type group is represented by the left hand bar, and the βcat(ex3)$_{osb}$ mice group the right hand bar. n=6 mice per group. *p<0.05 versus WT. Results are mean±SD.
Figure 12B:
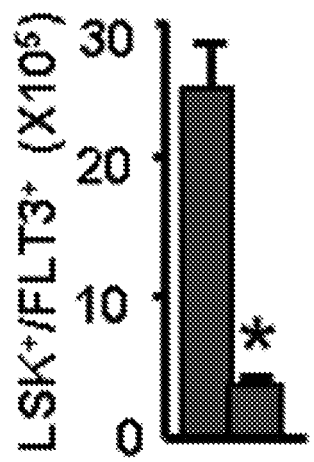
Figure 12C:
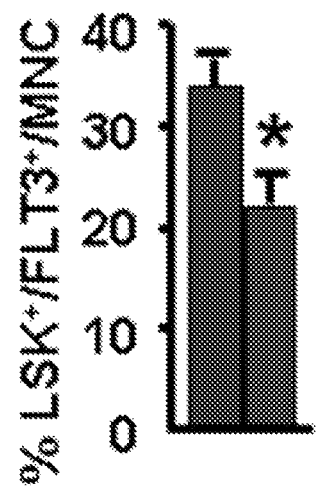
Figure 13:
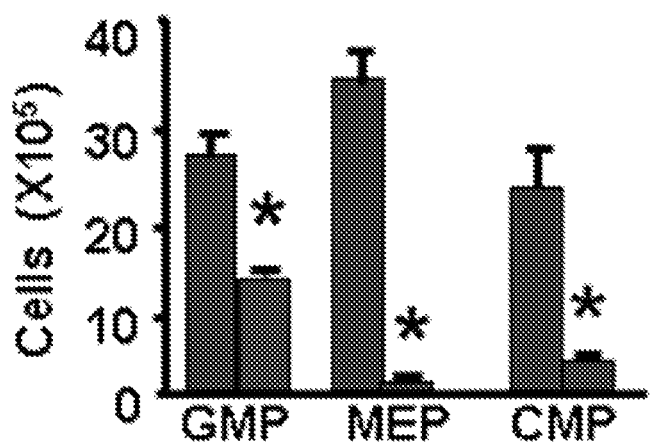
FIG. 13 is a graph depicting absolute numbers of each myeloid progenitor population (GMPs, MEPs and CMPs) in the bone marrow of wild type and βCat(ex3)$_{osb}$ mice. In the graph, the wild type group is represented by the left hand bar, and the βcat(ex3)$_{osb}$ mice group the right hand bar.
Figure 14A:
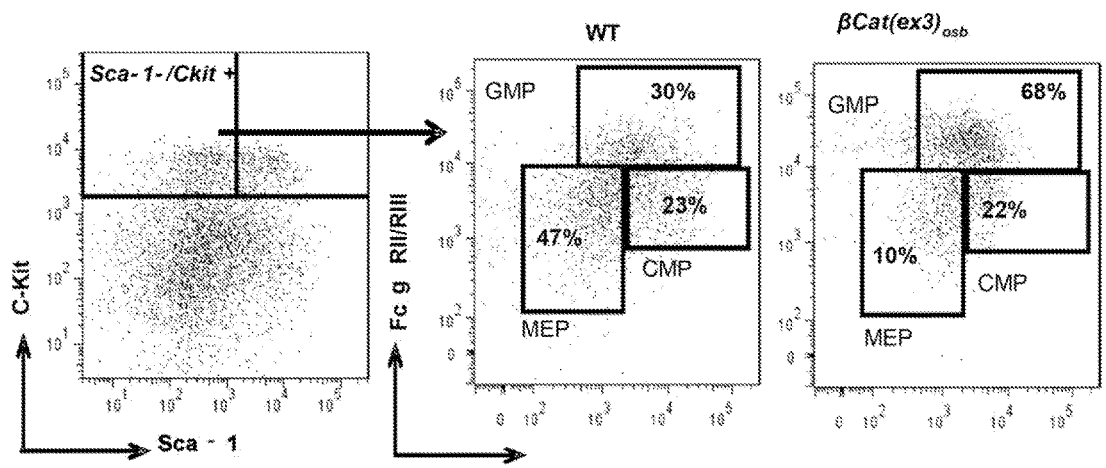
FIG. 14A shows the flow cytometry of the myeloid progenitor profile in the bone marrow of wild type (middle panel) and βCat(ex3)$_{osb}$ mice (right panel) by CD34-versus-FcgRII/III analysis of electronically gated Lin–Sca-1-c-Kit+ bone marrow cells: Granulocyte/monocyte progenitors (GMPs: LIN$^-$c-Kit$^+$Sca-1$^-$CD34$^+$FcγRII/III$^+$), megakaryocyte/erythroid progenitors (MEPs: LIN$^-$c-Kit$^+$Sca-1$^-$CD34$^-$FcγRII/III$^-$), and common myeloid progenitors (CMPs: (LIN$^-$c-Kit$^+$Sca-1$^-$CD34$^+$FcγRII/III$^-$).
Figure 14B:
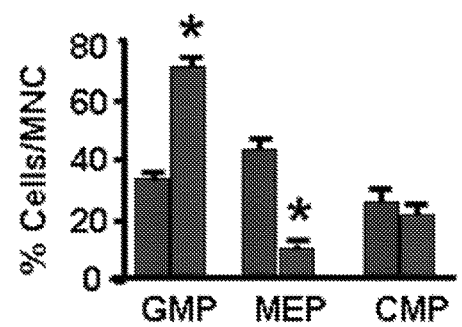
FIG. 14B is a graph of the percentage of myeloid progenitor populations in the bone marrow. In the graph, the wild type group is represented by the left hand bar, and the βcat(ex3)$_{osb}$ mice group the right hand bar. n=6 mice per group. *p<0.05 versus WT. Results are mean±SD.
Figure 15A:
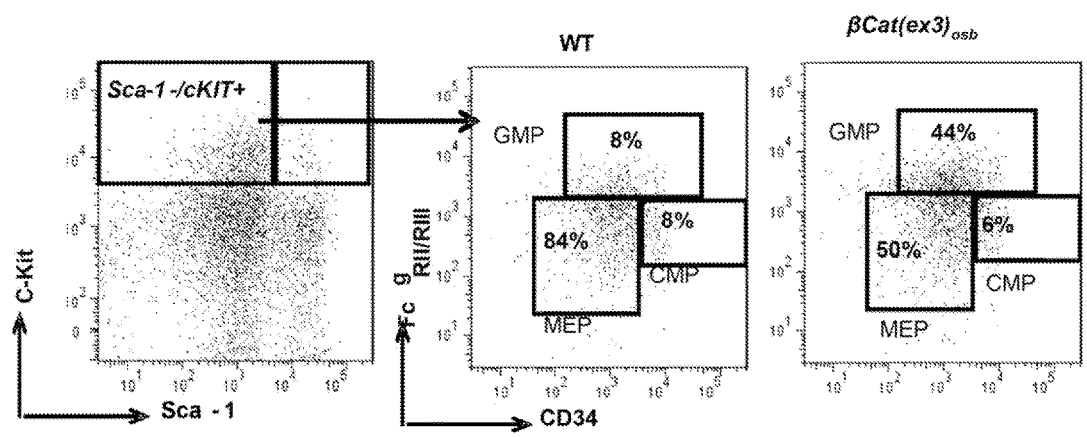
FIG. 15 is a representative flow cytometry analysis image (FIG. 15A) (WT-middle panel and βcat(ex3)$_{osb}$ mice-right hand panel) and quantification of myeloid progenitor populations in the spleen (FIG. 15B) of wild type and βCat (ex3)$_{osb}$ mice. In the graph, the wild type group is represented by the left hand bar and the βcat(ex3)$_{osb}$ mice group, the right hand bar. n=6 mice per group. *p<0.05 versus WT. Results are mean±SD.
Figure 15B:
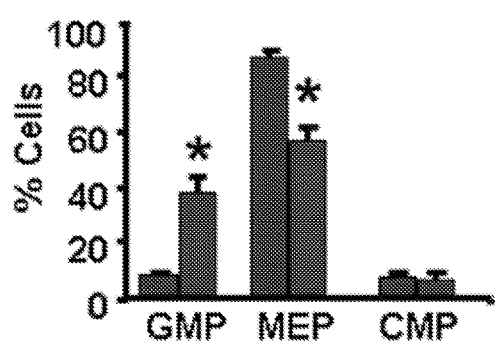

Because monocytes and granulocytes originate from the same progenitors, the hematopoietic stem and progenitor cell (HSPC) populations in the bone marrow were examined. The HSPC pool size, defined by Lin−Sca+c-Kit+ (LSK) cells, decreased 2-fold in βcat(ex3)$_{osb}$ mice, but their percentage was 2-fold greater than in wild type littermates (FIGS. 10A, 10B and 10C). The LSK+/CD150+/CD48− subset of long term repopulating HSC progenitors (LT-HSCs), increased both in numbers and percentage (FIGS. 10A, 10D and 10E). Activation of β-catenin was restricted to osteoblasts and was not affected in the LSK population of βcat(ex3)$_{osb}$ mice (FIG. 11). Increased myeloid activity was coupled with a reduction of the lymphoid-biased multipotential progenitor population, LSK+/FLT3+, in the bone marrow (FIG. 12). In the bone marrow, within the myeloid progenitor population (Lin−Kit+Sca1−), the granulocyte/monocyte progenitor subset (CD34+/FcgRII/III) also decreased (GMP population, FIG. 13) whereas the GMP percentage increased (FIG. 14). The GMP population percentage was also increased in the spleen of βcat(ex3)$_{osb}$ mice (FIG. 15).

Taken together, these findings were indicative of these mice having MDS, a pre-leukemia disorder characterized by trilineage dyspoiesis, bone marrow dysplasia with a variable percentage of blasts (<20%) and a high rate of progression to AML (>20% blasts) and/or AML (Kogan et al., 2002).

Example 4—Activation of β-Catenin in Osteoblasts Does Not Changes in the Non-Hematopoietic Compartment Because various stromal populations regulate HSCs and myelopoiesis, changes in the non-hematopoietic compartment of the βcat(ex3)$_{osb}$ mice were examined.

Materials and Methods

The same materials and method were used as in Example 2.

Results

MSC numbers as well as the expression of the MSC marker Nestin in the non-hematopoietic compartment and immature osteoblastic cells numbers remained similar between βcat(ex3)$_{osb}$ and wild type littermates (FIGS. 16A, B, C and D). Endothelial and leptin receptor expressing perivascular cells were also not affected. (FIGS. 16E and F).

The stromal compartment did not appear to be affected in βcat(ex3)$_{osb}$ mice.

Example 5—βcat(ex3)$_{osb}$ Mice Spontaneously Develop AML

To better define the nature of the hematopoietic disorder of βcat(ex3)$_{osb}$ mice, morphological assessments were performed that show these mice develop AML.

Materials and Methods

Mice as described in Example 2 were used.

Peripheral blood smears, histological analysis, karyotyping, immunostaining, clonogenic assays, and flow cytometry were performed as described in Example 1.

Results

Figure 17A:
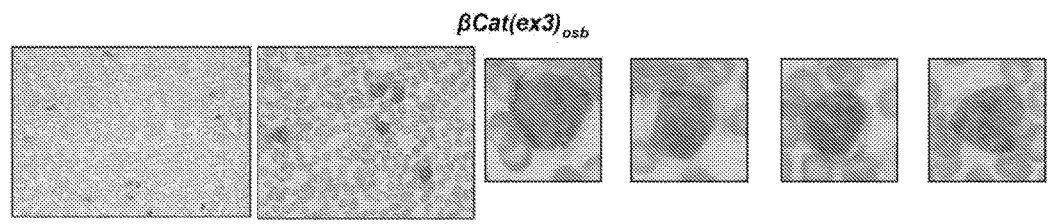
FIG. 17A shows peripheral blood smears showing immature monocytic blasts in βCat(ex3)$_{osb}$ mice (Wright-Giemsa staining, 40× and 100×). The three right panels show representative blasts from the two left images.
Figure 17B:
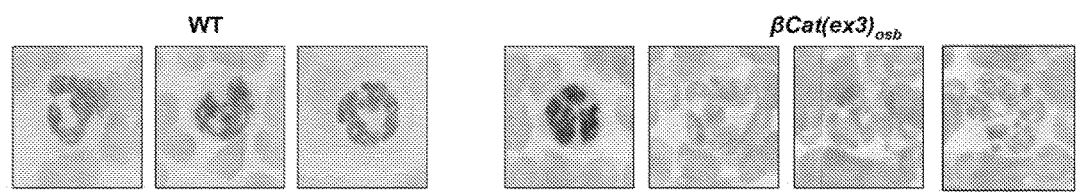
FIG. 17B depicts dysplastic neutrophils with hypersegmentation in βCat (ex3)$_{osb}$ mice (Wright-Giemsa staining) as compared to wild type mice. The wild type mice are shown in the left hand panels and the βCat(ex3)$_{osb}$ mice in the right hand panels. n=12 mice, ≥20 cells counted per sample; average±sem, range 13-81% and 12%-90% for neutrophils and blasts, respectively.

There was an increase in the myeloid and monocytic cells in blood, long bones, spleen and liver of βcat(ex3)$_{osb}$ mice (FIG. 17). Blasts (12-90%) and dysplastic neutrophils (3-81%), were also found in the blood of βcat(ex3)$_{osb}$ mice (FIGS. 17A and B).

Figures 17C, 17D:
FIG. 17C is bone marrow sections of βCat (ex3)$_{osb}$ mice showing blasts (60×).
FIG. 17D is bone marrow sections of wild type and βCat(ex3)$_{osb}$ mice. Arrows in the left hand panels of the βCat(ex3)$_{osb}$ mice indicate micro-megakaryocytes with hyperchromatic nuclei, and the arrows in the right hand panelshow erythroids. Images taken at 60×.

The bone marrow of the βcat(ex3)$_{osb}$ mice was characterized by dense and diffuse infiltration with myeloid and monocytic cells, the presence of blasts (30%-53% for n=12 mice) and abnormal megakaryoctytes indicative of dysplasia and increased erythroid activity (FIGS. 17C and 17D).

There was also a dense infiltration of mononuclear cells and marked increase in atypical micro-megakaryocytes with hypolobulated, hyperchromatic nuclei and immature cells with open chromatin, characteristic of blasts, in the spleen of the βcat(ex3)$_{osb}$ mice (FIGS. 17E and 17F). In the liver, clusters of immature cells with atypical nuclear appearance were seen in βcat(ex3)$_{osb}$ mice (FIG. 17G).

Figure 19B:
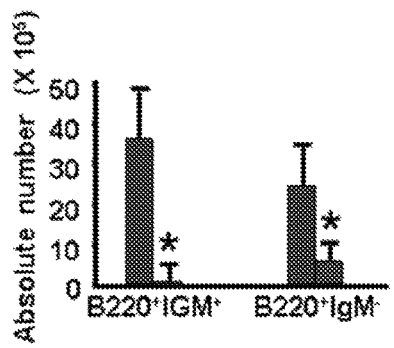
FIG. 19B shows the B-cell progenitor numbers in the bone marrow of βCat(ex3)$_{osb}$ mice and wild type mice.
Figure 19C:
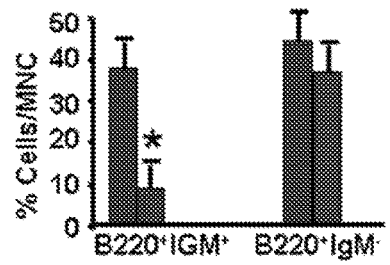
FIG. 19C shows the percentage of cells in the bone marrow of βCat(ex3)$_{osb}$ mice and wild type mice, showing a decreased B-lymphopoiesis in the bone marrow of βCat(ex3)$_{osb}$ mice. In every graph, the wild type group is represented by the left hand bar, and the βcat(ex3)$_{osb}$ mice group the right hand bar. n=6 mice per group. *p<0.05 versus WT. All flow cytometry data are representative of five independent experiments. Results are mean±SD.
Figure 20A:
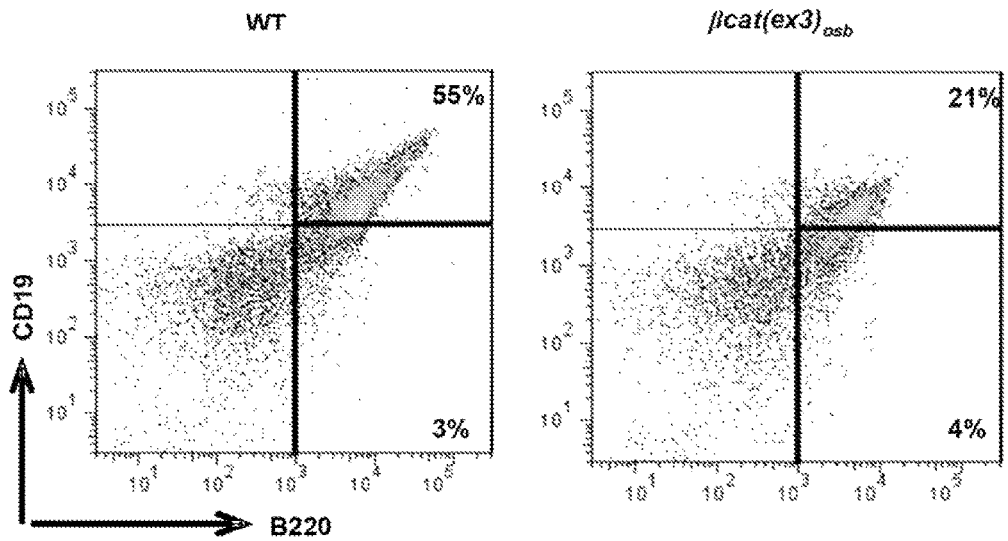
FIG. 20A is flow cytometry analysis of B-cell populations in the spleen of of wild type (left panel) and βCat(ex3)$_{osb}$ mice (right panel).
Figure 20B:
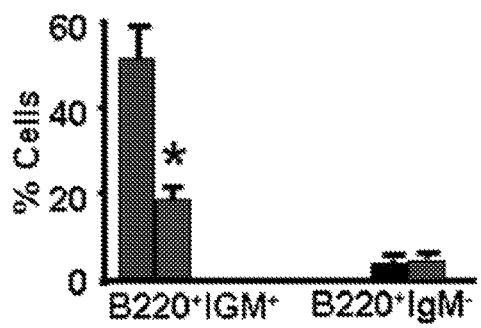
FIG. 20B shows the percentage of cells in the spleen of βCat(ex3)$_{osb}$ mice and wild type mice, showing a decreased B-lymphopoiesis in the spleen of βCat(ex3)$_{osb}$ mice. In the graph, the wild type group is represented by the left hand bar, and the βcat(ex3)$_{osb}$ mice group the right hand bar. n=6 mice per group. *p<0.05 versus WT. All flow cytometry data are representative of five independent experiments. Results are mean±SD.
Figure 23C:
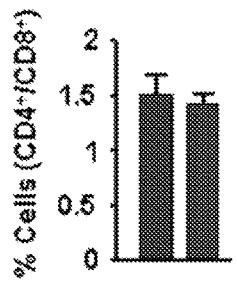
FIG. 23 are graphs showing the results of flow cytometry of CD4 and CD8 expression in the thymus (FIGS. 23A and 23B), the peripheral blood (FIGS. 23C and 23D), the lymph nodes (FIGS. 23E and 23F), and the spleen (FIGS. 23G and 23H) in wild type and βCat(ex3)$_{osb}$ mice. In every graph, the wild type group is represented by the left hand bar, and the βcat(ex3)$_{osb}$ mice group the right hand bar. n=6 mice per group. Results are mean±SD.
Figure 23D:
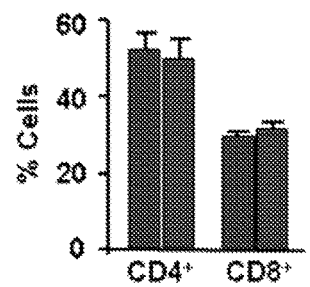
Figure 23E:
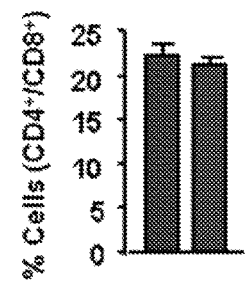
Figure 23F:
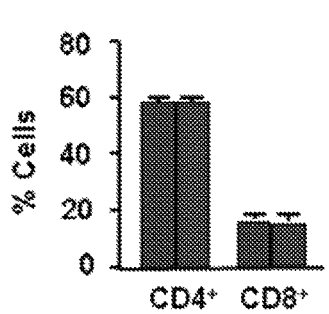
Figure 23G:
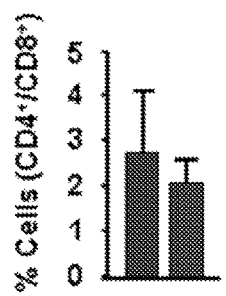
Figure 23H:
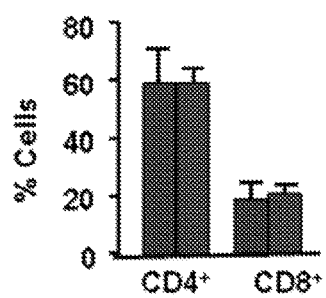

The increase in immature myeloid cells was confirmed by staining with myeloperodixase in long bones, spleen and liver (FIGS. 18A, B, and C). CD117 (c-kit) staining and CD13 was also observed in long bones (FIGS. 18D and E). In addition, as shown by flow cytometry, Bcat(ex3)$_{osb}$ mice had reduced B-cells and B-cell progenitors with a concomitant increase in the frequency of myeloid cells in the bone marrow, spleen, and lymph nodes (FIGS. 19, 20, and 21). The T-cell population in the thymus was not affected (FIGS. 22 and 23).

Figure 24A:
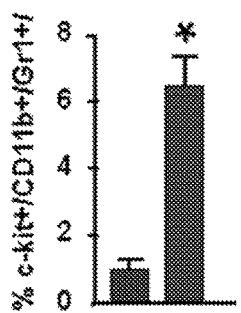
FIG. 24A is a graph of the percentage of undifferentiated immature myeloid cells and FIG. 24B are bone marrow sections stained with Giemsa of wild type (left hand panel) and βCat(ex3)$_{osb}$ mice (right hand panel) showing the lack of myeloid differentiation in βCat(ex3)$_{osb}$ mice bone marrow cells. In the graph, the wild type group is represented by the left hand bar, and the βcat(ex3)$_{osb}$ mice group the right hand bar. n=8 mice per wild type and n=12 mice per βCat(ex3)$_{osb}$ mice group. Results of representative of five independent experiments. *p,0.05 versus WT. Results of mean±SD.
Figure 24B:
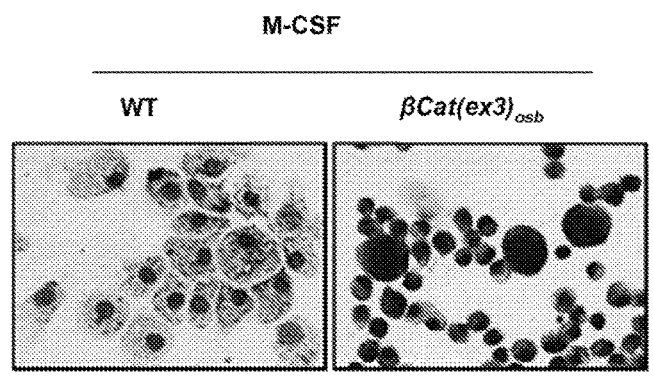

Differentiation blockade was demonstrated by the presence of immature myeloid progenitors in βcat(ex3)$_{osb}$ marrow and differentiation cultures. See FIGS. 24-26.

These data taken together: the detection of blasts in the blood; the increase in immature myeloid and monocytic cells with atypical features; and the decreased B-lymphopoiesis; fulfill the criteria of AML diagnosis in mice (Kogan et al., 2002) and principle features of human AML (Sternberg et al., 2005; Van de Loosdrecht et al., 2008).

Example 6—βcat(ex3)$_{osb}$ Mice have a Clonal Abnormalities and Chromosomal Alterations Because AML is associated with clonal evolution at the cytogenetic level, the βcat(ex3)$_{osb}$ mice were examined for genetic abnormalities.
Materials and Methods
Mice as described in Example 2 were used.
Karyotyping, array comparative genomic hybridization, and whole exome sequencing were performed as described in Example 1.
Results
A clonal abnormality was identified involving a Robertsonian translocation Rb(1;19) in 2 of 30 metaphases studied in spleen specimens derived from an 18-day old βcat(ex3)$_{osb}$ mouse (FIG. 27).

Genomic aberrances were searched for in the bone marrow of βcat(ex3)$_{osb}$ mice using array Comparative Genomic Hybridization (aCGH) to germline DNA with the Mouse Genome 244K platform. Recurrent numerical and structural chromosomal alterations were detected in the spleen of all mutant mice (n=5) examined (FIG. 28, Table 3). The most frequent, abnormalities were detected in chromosome 5, the mouse ortholog of human chromosome 7q which is associated with common cytogenetic abnormalities in MDS/AML patients (Raza and Galili, 2012); and 17, the mouse ortholog for human chromosome 6q. Other deletions affected the Mllt4 (AF6) locus frequently involved in MLL and MLLT4 translocations in human AML and the cell cycle-suppressing phosphatase Ppp2ca associated with human MDS (Meyer et al., 2009; Wei et al., 2009).

Whole-exome sequencing identified four non-silent somatic mutations in myeloid cells from three βcat(ex3)osb mice (Table 4 and FIG. 29), including a recurrent one in tnrsf21 and a single somatic mutation in Crb1 previously reported in human AML (The Cancer Genome Atlas Research Network, 2013).

The clonal abnormalities identified support the notion that constitutive activation of β-catenin in osteoblasts facilitates clonal progression in myeloid progenitors leading to AML.

TABLE 3

Structural Chromosomal Alterations Detected by aCGH in βcat(ex3)$_{osb}$ Mice (n = 5)

| Mouse Chromosome | Location (Mb) | Size (kb) | Genes | Copy number change | Mouse ID | Human chromosome | Location (Mb) |
|---|---|---|---|---|---|---|---|
| 2 | 54.7 | 114 | Glant13 | Deletion of ⅔ copies | 1 | No ortholog | |
| 3 | 93.4 | 608 | Tdpoz2, Tdpoz1, Tdpoz4, Tdpoz3, Tdpoz5, Gm10697, Gm9125, Gm10696 | Deletion of ⅓ copies | 1 | No orthologs | |
| 4 | 62.1 | 245 | Bspry, Hdhd3, Alad | Deletion of ⅓ copies | 3 | 9q32 | 115.16 115.17 115.2 |
| 5 | 26.3 | 980 | Speer4a, BC061212, A430089I19Rik | Deletion of ¾ copies | 2, 3 | No orthologs | |
| | 95.6 | 238 | AA792892, Gm16367, D5Ertd577e, 100041354 | Deletion of ⅓ copies | 5 | | |
| 5 | 5.1 | 196 | Pftk1 | Gain of <1 copy | 2 | 7q21.13 | 90.4 |
| | 13.5 | 181 | Sema3a | Gain of 1 copy | 2, 3 | 7q21.11 | 83.5 |
| | 15.7 | 398 | Cacna2d1 | Gain of <1 copy | 2, 3 | 7q21.11 | 81.6 |
| | 22.6 | 227 | Lhfpl3 | Gain of >1 copy | 2, 3, 4, 5 | 7q22.1 | 104 |
| 6 | 144 | 59 | Sox5 | Deletion of ¾ copies | 1, 2, 3, 4 | 12p12.1 | 23.9 |
| 7 | 123 | 59 | Sox6 | Deletion of ⅔ copies | 5 | 11p15.2-15.1 | 16.2 |
| 8 | 87.2 | 4.1 | Nfix | Deletion of ½ copies | 3, 4 | 19p13.2 | 13.2 |
| | 97.5 | 43 | Gpr56 | Deletion of ½ copies | 3 | No ortholog | |
| 8 | 75 | 16 | Slc35e1 Med26 | Gain of <1 copies | 3 | 19p13.11 19p13.11 | 16.5 16.6 |
| | 22.3 | 494 | Defa-rs7 Defa23 Defa25 Defa22 Defa3 Defa5 Defcr-rs1 Defa20 | Gain of <1 copies | 4 | No ortholog No ortholog No ortholog No ortholog 8p23.1 8p23.1 No ortholog No ortholog | 6.8 6.9 |
| 9 | 53.3 | 0.06 | Npat | Heterozygous deletion | 1 | 11q22.3 | 107.5 |
| 10 | 106.2 | 0.06 | Ppfia2 | Heterozygous deletion | 1, 3, 4 | 12q21.31 | 80.4 |
| 11 | 51.9 | 12.9 | Ppp2ca | Deletion of ⅔ copies | 5 | 5q31.1 | 133.5 |
| | 66.6 | 32 | No genes | Deletion of ½ copies | 4, 5 | | |
| | 90.1 | 5.9 | No genes | Deletion of ¾ copies | 4 | | |
| 12 | 8.9 | 0.05 | Matn3 | Heterozygous deletion | 5 | 2p24.1 | 20.1 |
| 12 | 114.7 | 475 | Adam6b, Adam6a | Gain of <1 copy | 4 | 14q32.33 | 105.5 |
| | 31 | 71 | Sntg2 | Gain of <1 copy | 1 | 2p25.3 | 1.1 |
| 13 | 67.5 | 163 | No genes | Deletion of ⅔ copies | 3 | | |

TABLE 3-continued

Structural Chromosomal Alterations Detected by aCGH in βcat(ex3)$_{osb}$ Mice (n = 5)

| Mouse Chromosome | Location (Mb) | Size (kb) | Genes | Copy number change | Mouse ID | Human chromosome | Location (Mb) |
|---|---|---|---|---|---|---|---|
| 14 | 108 | 380 | No genes | Heterozygous deletion | 1, 2, 3, 4 | | |
| | 110 | 19 | 1700112E06Rik | Deletion of ⅔ copies | 5 | No ortholog | |
| 15 | 23.7 | 201 | No genes | Deletion of ½ copies | 2, 3, 4 | | |
| 15 | 20.4 | 20 | No genes | Gain of <1 copy | 2, 3, 4, 5 | | |
| | 77.3 | 47 | Apol10a, Apol7c | Gain of <1 copy | 2, 3, 4, 5 | No ortholog | |
| 17 | 15.1 | 86 | Gm3448, Gm3417, 9030025P20Rik, Gm3435, Tcte3, 2210404J11Rik | Heterozygous deletion | 2, 3, 4, 5 | No ortholog No ortholog No ortholog No ortholog 6q27 No ortholog | 170.1 |
| | | 38 | LOC547349 | Deletion of ⅔ copies | 2, 5 | No ortholog | |
| | 35.4 | 4 | H2-T3, H2-Tw3 | Heterozygous deletion | 2, 5 | No ortholog | |
| | 36.3 | 60 | Crisp1 | Deletion of ¾ copies | 2, 5 | 6p12.3 | 49.8 |
| | 40.4 | 494 | Tcp10a, Tcte2, Mllt4 | Deletion of ⅓ copies | 4 | 6q27 No ortholog | 167.8 |
| | 33.1 | 33 | Zfp472, C920016K16Rik | Deletion of ⅔ copies | 4 | 6q27 No ortholog | 168 |
| | 38.4 | 60 | Olfr137, Olfr136 | Deletion of ¾ copies | 4 | No ortholog No ortholog | |
| 17 | 6.1 | 701 | Tulp4, Tmem181a, Dynlt1, Tmem181b, Tmem181c-ps, Tmem181d-ps, Sytl3 | Gain of <1 copy | 2 | 6q25.3 | 158.7 158.9 159 159 |
| | 7.4 | 45 | Rps6ka2, Tcp10b, Tcp10a | Gain of <1 copy | 2, 3 | 6q27 6q27 | 166.9 167.7 |
| | 35.5 | 65 | H2-Q8, H2-Q6, H2-Q7 | Gain of <1 copy | 2 | No ortholog | |
| | 36.1 | 241 | H2-T24, H2-T23, H2-T9, H2-T22, EG547347, H2-B1, H2-T10, Gm8909, H2-T3, H2-Tw3 | Gain of <1 copy | 2, 3, 5 | No ortholog | |
| | 37.5 | 19 | No genes | Gain of >1 copy | 2, 5 | | |
| | 38.4 | 60 | Olfr137, Olfr136 | Gain of >2 copies | 2, 3, 5 | No ortholog | |
| | 13.4 | 364 | Tcp10a | Deletion of ⅔ copies | 3, 5 | 6q27 | 167.7 |
| 19 | 37.4 | 114 | Ide | Deletion of ⅔ copies | 3, 4 | 10q23.33 | 94.3 |
| | 36.9 | 39 | Fgfbp3, Btaf1 | Deletion of ½ copies | 3 | 10q23.32 | 93.6, 93.7 |

TABLE 4

Results of Whole-Exome Sequencing

| Mouse | Gene | Mutation | Exon | Amino Acid Change | Location |
|---|---|---|---|---|---|
| 1 | Tnfrsf21 | C715 T | 2 | H239Y | Chr 17:43038213 |
| 2 | Tnfrsf21 | C715 T | 2 | H239Y | Chr 17::43038213 |
| 1 | Crb1 | G2305A | 1 | G769S | Chr 1:139243346 |
| 3 | 4930596D02Rik | G65A | 1 | R22H | Chr 14:35811883 |

Example 7—The AML Phenotype of the βcat(ex3)$_{osb}$ Mice is Transferrable and Cell Intrinsic To assess whether the AML phenotype of βcat(ex3)$_{osb}$ is transferrable and cell intrinsic, bone marrow cells from βcat(ex3)$_{osb}$ (CD45.2) mice with AML were transplanted into lethally irradiated WT B5.SJL (CD45.1) recipients.

Materials and Methods

The βcat(ex3)$_{osb}$ mice as described in Example 2 were used.

Bone marrow transplantation, hematological measurements, peripheral blood morphology, flow cytometry, PCR, and histological analysis were performed as described in Example 1.

Results

Figure 32:
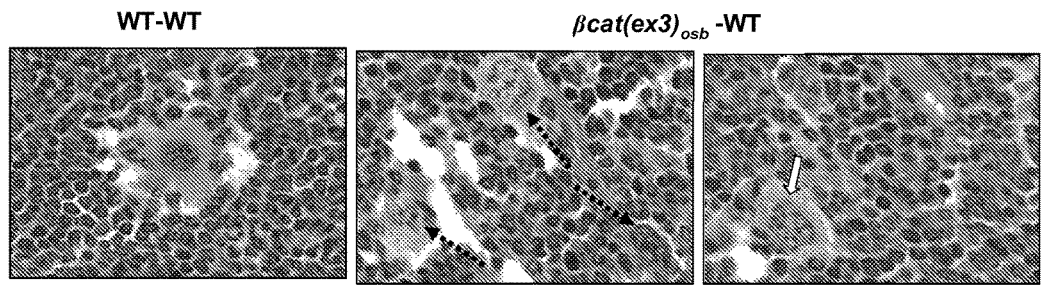
FIG. 32 are bone marrow sections of WT-WT mice (left hand panel) and βCat(ex3)$_{osb}$_WT (right hand panels), showing blasts (dotted arrows) and dysplastic megakaryocytes (white arrow) in the bone marrow of βCat(ex3)$_{osb}$_WT transplanted mice.
Figure 33:
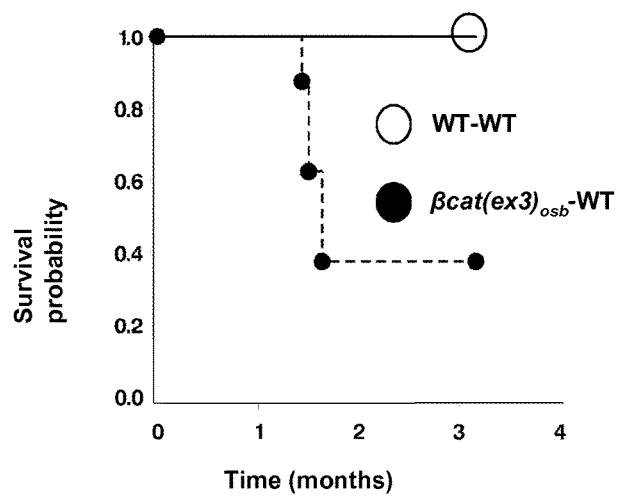
FIG. 33 is Kaplan-Meier survival curves comparing WT-WT and βCat(ex3)$_{osb}$_WT mice.
Figures 34A, 34B:
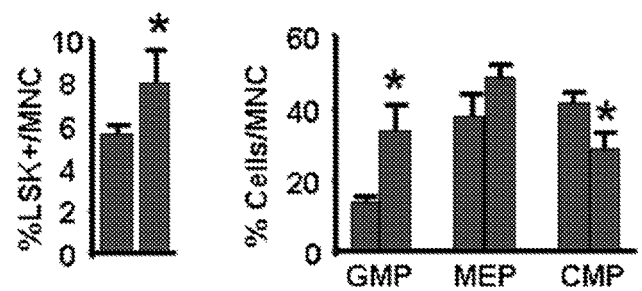
FIG. 34A shows LSK cells.
FIG. 34B, GMPs, MEPs and CMPs.
Figure 34C:
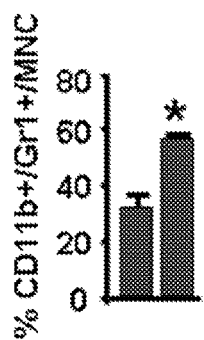
FIG. 34C, CD11b+/Mac+ cells.
Figure 34D:
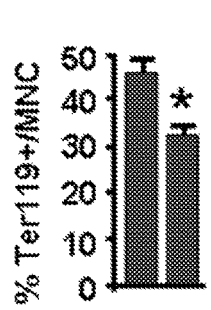
FIG. 34D, erythroid cells.
Figure 34E:
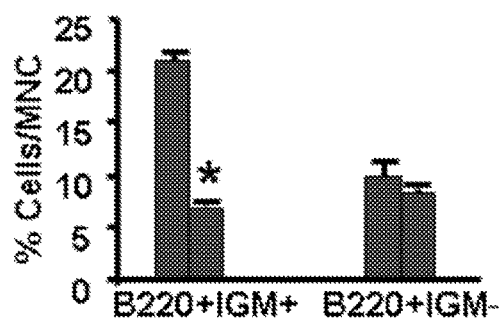
FIG. 34E, B-lymphopoiesis.

Assessment of peripheral blood and bone marrow 16 weeks after transplant showed 85-97% chimerism. Recipients, designated βcat(ex3)$_{osb}$-WT, developed all features of hematopoietic dysfunction and AML observed in βcat (ex3)$_{osb}$ mice, including an increase in LSK numbers and deregulation of HSC lineage differentiation (FIG. 30). Blasts and dysplastic neutrophils with nuclear hypersegmentation were seen in the blood of recipient mice (FIG. 31); their numbers ranged from 15-80% and 15-75%, respectively. The bone marrow of the βcat(ex3)$_{osb}$-WT mice was characterized by the presence of blasts (30 to 40%) and abnormal megakaryocytes indicative of dysplasia (FIG. 32), as well as early lethality (FIG. 33).

Figure 35A:
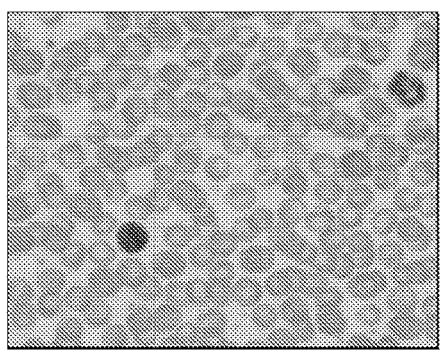
FIG. 35 are peripheral blood smears of wild type (FIG. 35A) and WT-βCat(ex3)$_{osb}$ showing blasts (FIG. 35B).
Figure 35B:
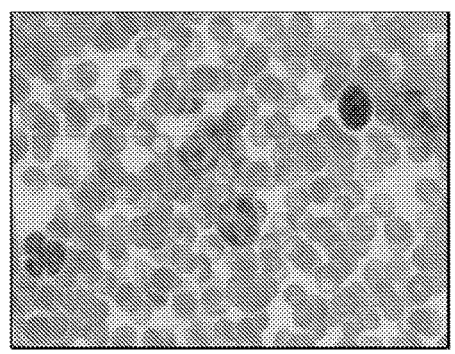
Figure 36A:
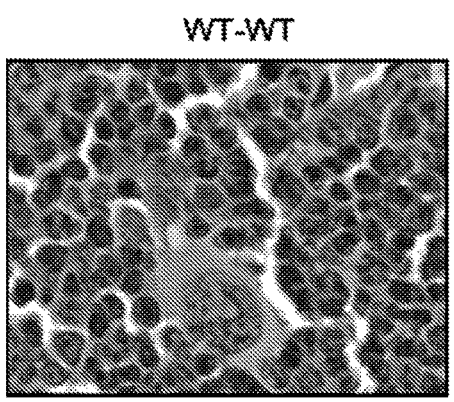
FIG. 36 are sections of bone marrow of WT-WT mice (FIG. 36A) and WT-βCat(ex3)$_{osb}$ mice (FIG. 36B).
Figure 36B:
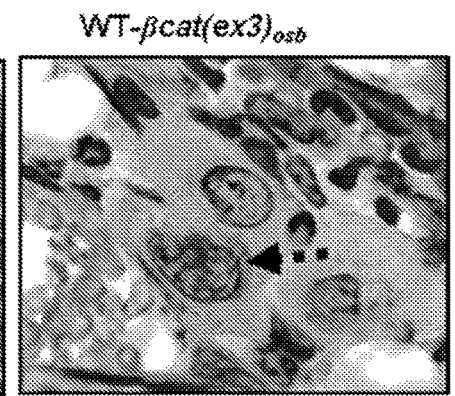
Figure 37:
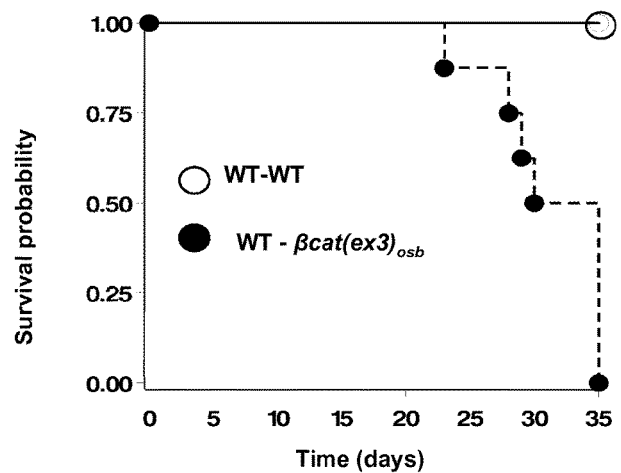
FIG. 37 are Kaplan-Meier survival curves comparing WT-WT and WT-βCat(ex3)$_{osb}$.

Transplantation of WT B5.SJL (CD45.1) bone marrow cells to lethally irradiated βcat(ex3)$_{osb}$ (CD45.2) mice (designated WT-βcat(ex3)$_{osb}$) also resulted in hematopoietic dysfunction and AML as shown by the same measurements (FIGS. 34-36), as well as early lethality (FIG. 37).

Figures 38A, 38B, 38C:
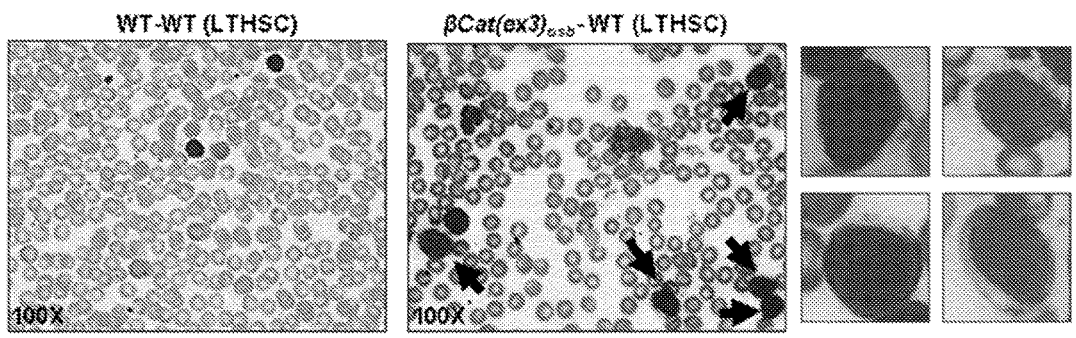
FIG. 38C shows 100× magnification of blasts. Blasts are shown in FIG. 38B by black arrows.
Figure 39:
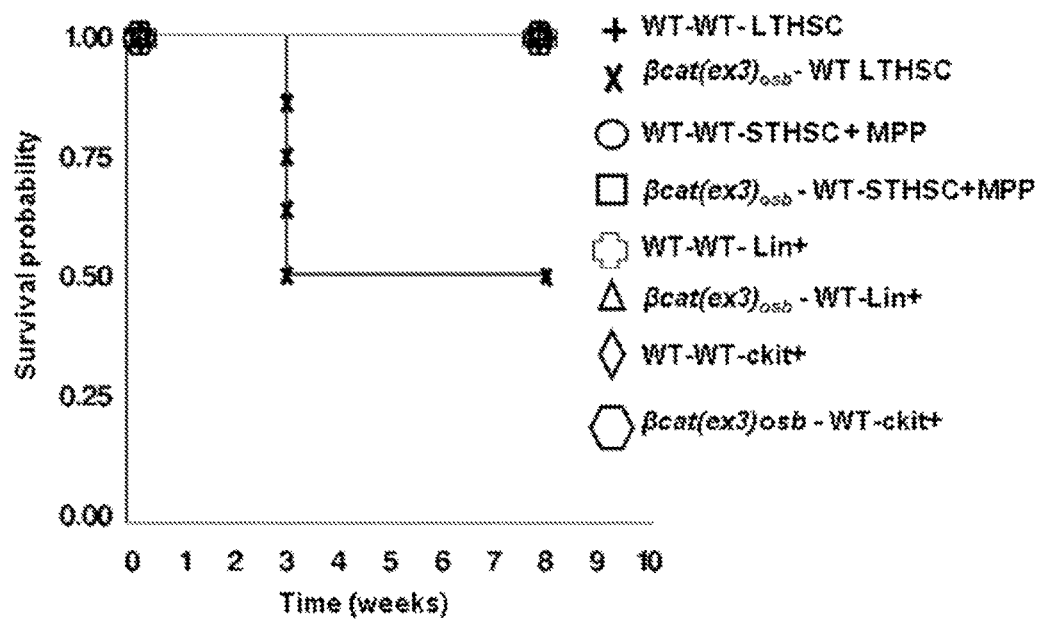
FIG. 39 are Kaplan-Meier survival curves comparing WT mice transplanted with the indicated hematopoietic populations from βCat(ex3)$_{osb}$ n=7. Results are representative of two independent experiments.
Figure 40A:
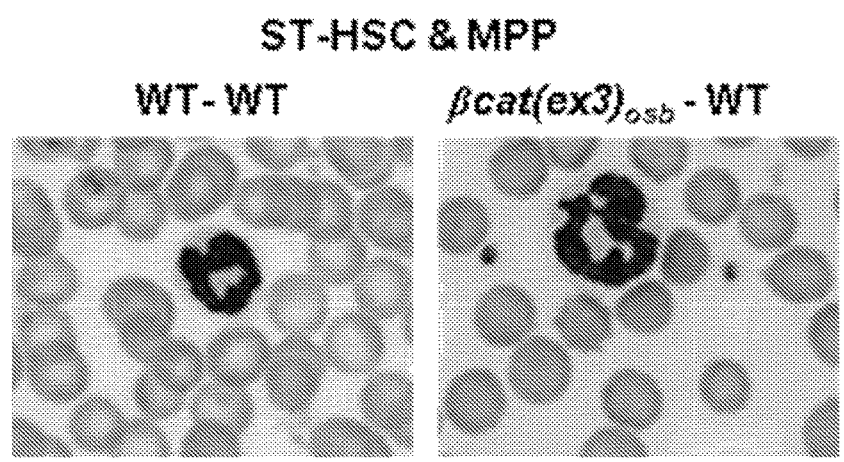
FIG. 40A show results of transplants with ST-HSC and MPP.
Figure 40B:
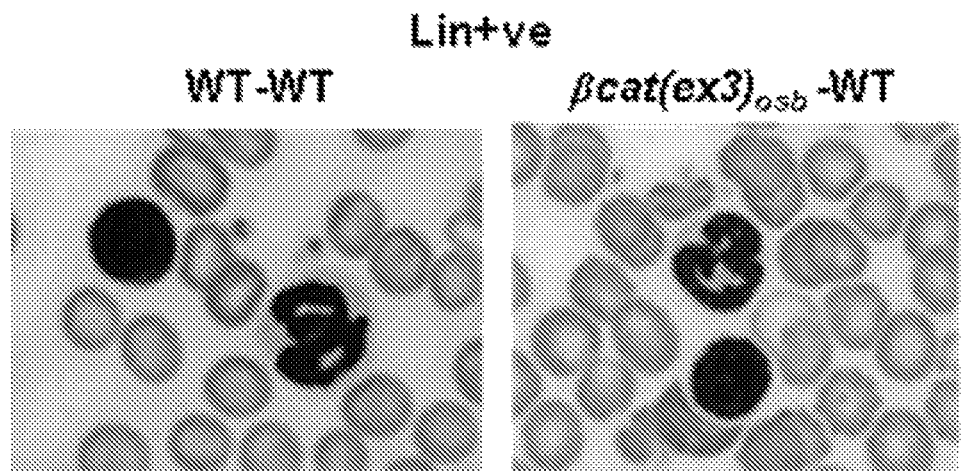
FIG. 40B shows results from lin+VE.
Figure 40C:
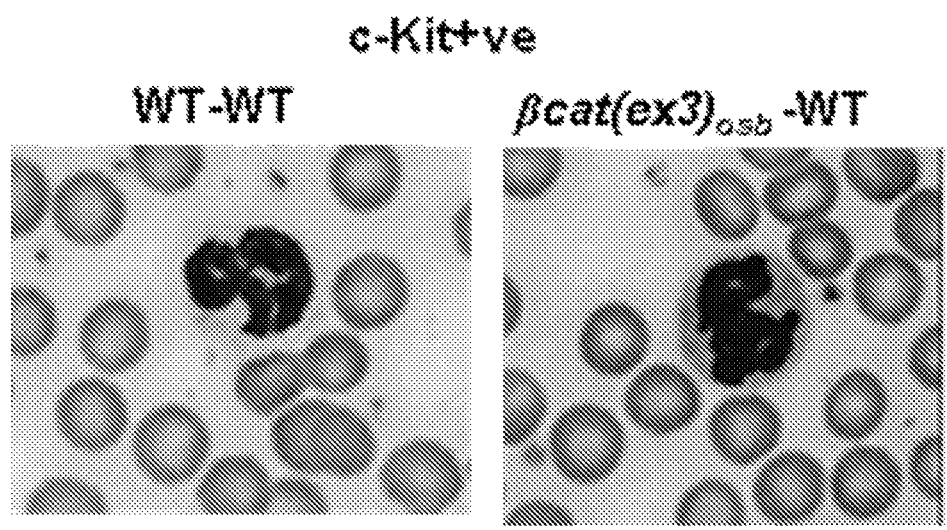
FIG. 40C shows the results for c-Kit+ve.
Figures 41A, 41B:
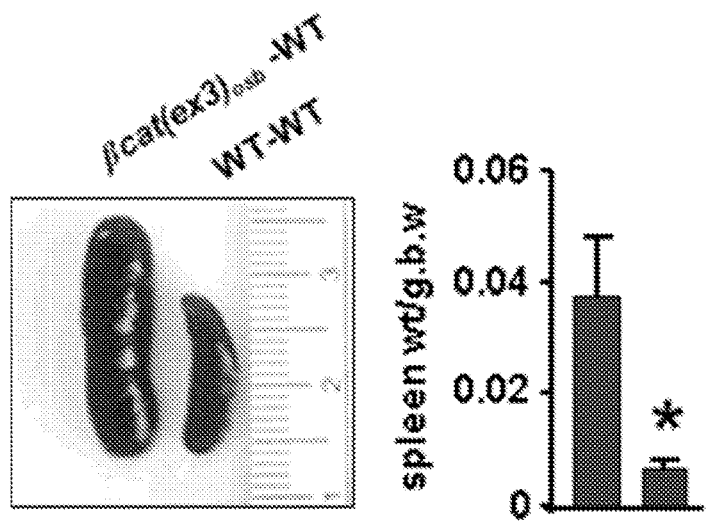
FIG. 41A shows a spleen of a WT-WT mouse and a βCat(ex3)$_{osb}$-WT mouse.
FIG. 41B shows the spleen weight of WT-WT mice and βCat(ex3)$_{osb}$-WT mice.
Figures 41C, 41D:
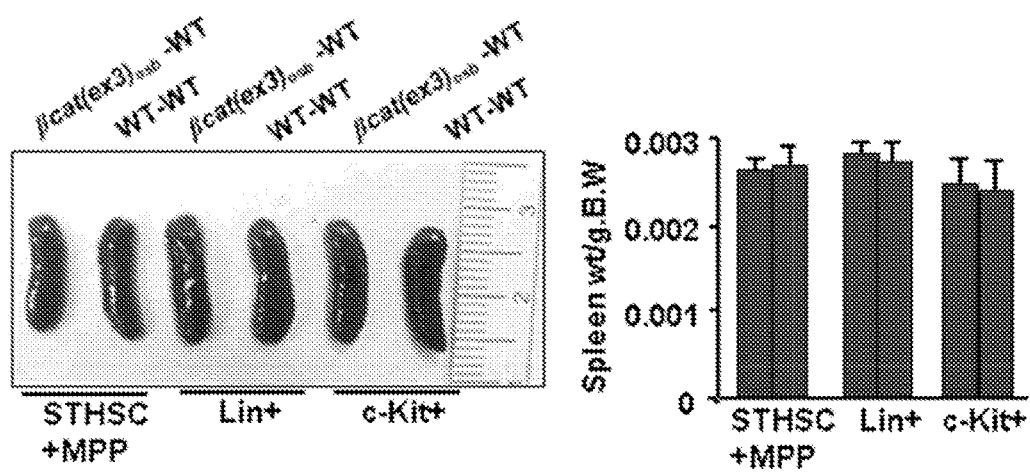
FIG. 41C shows spleens from WT-WT mice as well as mice transplanted with ST-HSC and MPP, Lin+, and c-KIT+.
FIG. 41D are graphical result of the weights of the various spleens. In every graph, the wild type group is represented by the left hand bar and the βcat(ex3)$_{osb}$-WT mice groups are the right hand bar.
Figure 42A:
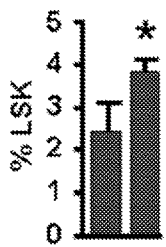
FIG. 42A are LSK cells.
Figure 42B:
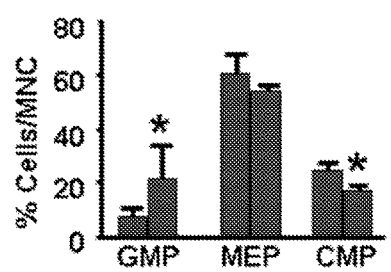
FIG. 42B, GMPs, MEPs, and CMPs.
Figure 42C:
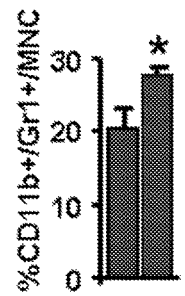
FIG. 42C, CD11b+/Mac+ cells.
Figure 42D:
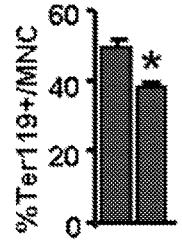
FIG. 42D, erythroid cells.
Figure 42E:
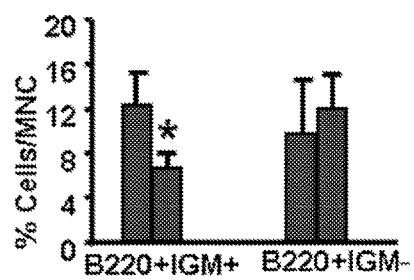
FIG. 42E, B-lymphopoiesis in the liver.
Figure 42F:
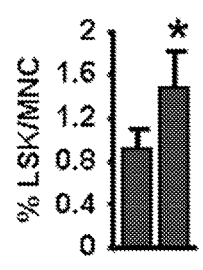
FIG. 42F shows LSK cells.
Figure 42G:
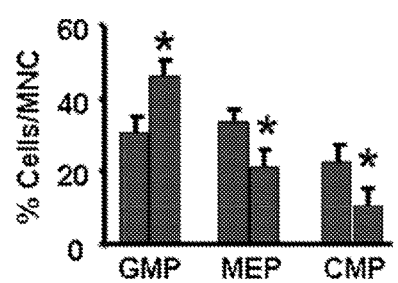
FIG. 42G, GMPs, MEPs and CMPs.
Figure 42H:
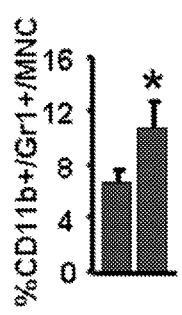
FIG. 42H, CD11b+/Mac+ cells.
Figure 42I:
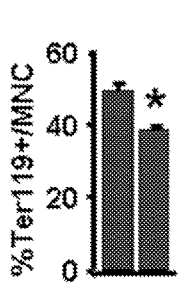
FIG. 42I, erythroid cells.
Figure 42J:
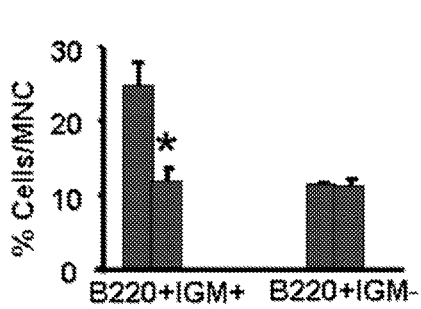
FIG. 42J, B-lymphopoiesis in the bone marrow of newborn mice. In every graph, the wild type group is represented by the left hand bar, and the βcat(ex3)$_{osb}$ mice (PI) group the right hand bar.
Figures 43A, 43B, 43C:
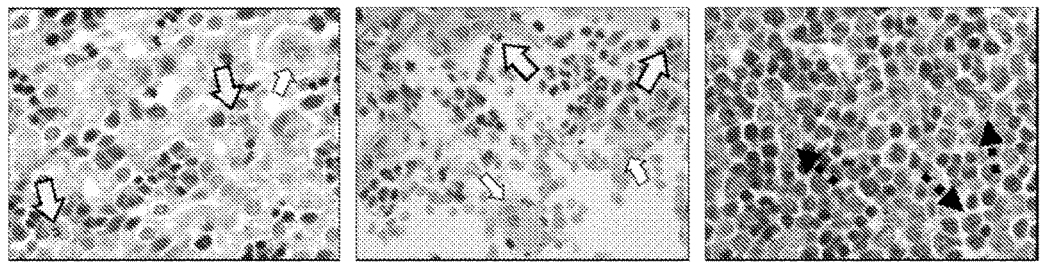
FIG. 43 are sections of the liver (FIG. 43A), bone marrow (FIG. 43B), and spleen (FIG. 43C) of newborn (P1) βCat (ex3)$_{osb}$ mice showing microhypolobated megakaryocytes (white arrows in FIG. 43A), Pelger Huet neutrophils (white arrows in FIG. 43B) or blasts (dotted arrows in FIG. 43C). Images were taken at 100×.

Transplantation of LT-HSCs but not other hematopoietic populations (ST-HSC and MPP; Lin+ve; and c-kit+ve) from βcat(ex3)osb mice to sublethally irradiated wild-type mice recipients resulted in AML with early lethality (FIG. 39 and Table 6) indicating that LT-HSCs are the leukemia-initiating cells (LICs) (FIGS. 38-41; Table 5 and 6). Mice that were transplanted with LT-HSCs had blasts (FIG. 38) but mice transplanted with other hematopoietic cells did not have blasts in their blood (FIG. 40). Mice transplanted with LT-HSCs also had much lower spleen weights than mice transplanted with other hematopoietic cells (FIG. 41). Additionally mice transplanted with LT-HSCs had lower HCT and platelet counts (Table 5) and went on to develop AML (Table 6).

whether AML development stems from previous MDS, hematopoiesis in newborn (P1) pups was examined.

Materials and Methods

The $\beta cat(ex3)_{osb}$ mice as described in Example 2 were used.

Hematological measurements, peripheral blood morphology, flow cytometry, PCR, and histological analysis were performed as described in Example 1.

Results

Livers of $\beta cat(ex3)_{osb}$ newborn mice showed an increase in LSK cells and cells of the myeloid lineage, and a decrease in erythroid and B-lymphoid cells (FIGS. 29A-E). Micro-hypolobated megakaryocytes, and Pelger Huet neutrophils, which can be seen in MDS and other congenital entities, and nuclear cytoplasmic asynchrony in the erythroid lineage were also seen (FIG. 30A). These abnormalities were also

TABLE 5

Peripheral Blood Measurements of mice transplanted with various hematopoietic cells

|  | WT-WT LT-HSC | $\beta cat(ex3)_{osb}$- WT LT-HSC | WT-WT ST-HSC + MPP | $\beta cat(ex3)_{osb}$- WT ST-HSC + MPP | WT-WT Lin + ve | $\beta cat(ex3)_{osb}$- WT-WT Lin + ve | WT-WT- c-kit + ve | $\beta cat(ex3)_{osb}$- WT c-kit + ve |
|---|---|---|---|---|---|---|---|---|
| WBC ($\times 10^3/\mu l$) | 3.46 ± 0.9 | 3.52 ± 2.1 | 4.1 ± 0.1 | 3.9 ± 0.3 | 3.4 ± 0.2 | 3.8 ± 0.5 | 3.9 ± 0.3 | 3.7 ± 0.8 |
| HCT (%) | 40.5 ± 2.6 | 21.2 ± 2.1* | 42.7 ± 4.3 | 43.7 ± 3.4 | 43.8 ± 1.8 | 42.5 ± 2.9 | 43.7 ± 1.8 | 46.7 ± 3.9 |
| Platelets ($10^3/\mu l$) | 136.1 ± 278.5 | 356.3 ± 165.8* | 1196.6 ± 180.8 | 1291 ± 184.1 | 1360 ± 98.7 | 1399 ± 79.1 | 1430 ± 59.4 | 1466.3 ± 36.1 |

White blood cells (WBC), Hematocrit (HCT)

TABLE 6

Disease development in mice transplanted with various hematopoietic cells

| Donor cells | Number of Donor cells | Number of Recipients | Wild type Donor AML | $\beta cat(ex3)_{osb}$ Donor AML | WT-WT Recipient Lethality Dead/Total | $\beta cat(ex3)_{osb}$- WT Recipient Lethality Dead/Total |
|---|---|---|---|---|---|---|
| LT-HSC | $7 \times 10^3$ | 7 | 0/7 | 7/7 | 0/7 | 4/7 |
| ST-HSC & MPP | $20 \times 10^3$ | 5 | 0/5 | 0/5 | 0/5 | 0/5 |
| Lin + ve | $10 \times 10^4$ | 5 | 0/5 | 0/5 | 0/5 | 0/5 |
| c-kit + ve | $10 \times 10^4$ | 5 | 0/5 | 0/5 | 0/5 | 0/5 |

These results demonstrate that osteoblasts are the cells responsible for AML development. More intriguingly, and in combination with the detection of cytogenetic abnormalities in $\beta cat(ex3)_{osb}$ marrow and spleen, they indicate that HSCs of $\beta cat(ex3)_{osb}$ mice have acquired a permanent self-perpetuating genetic alteration that becomes independent of the initial mutation in the βcat(ex3) osteoblast precursor.

Example 8—Deregulated Hematopoiesis with MDS is Found in Newborn $\beta cat(ex3)_{osb}$ Mice All (n=110) $\beta cat(ex3)_{osb}$ mice examined eventually develop AML between 2 (40%) and 3.5 (60%) weeks of age. To accurately determine the disease onset and to investigate observed in the bone marrow (FIGS. 29F and 29I and FIG. 30B). Spleens of mutant mice showed increased number of blasts and a shift towards the myeloid lineage compared to wild type littermates (FIG. 30C).

These characteristics indicate deregulated hematopoiesis along with neutrophil dyspoiesis at birth, suggesting that osteoprogenitors may affect the fate of fetal HSCs. Less than 20% blasts were seen in the marrow, consistent with a diagnosis of MDS with excess blasts (RAEB1/2).

Figure 44:
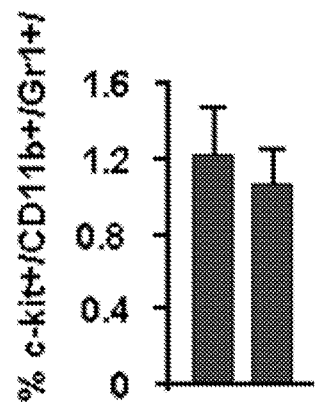
FIG. 44 is a graph depicting the number percentage of immature myeloid cells in the bone marrow of wild type and βCat(ex3)$_{osb}$ mice. In the graph, the wild type group is represented by the left hand bar, and the βcat(ex3)$_{osb}$ mice group the right hand bar.
Figure 45A:
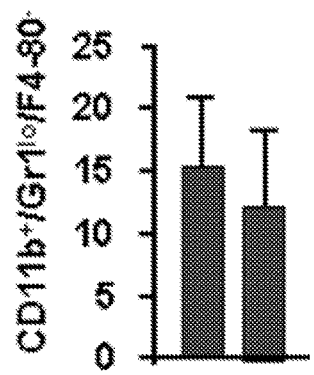
FIG. 45 are graphs of flow cytometry results of clonogenic assays in the bone marrow of wild type and newborn (P1) βCat(ex3)$_{osb}$ mice with M-CSF (FIG. 45A); GM-CSF (FIG. 45C); and G-CSF (FIG. 45E), and Giemsa-stained bone marrow section of the same mice wild type (left hand panels) and P1 βCat(ex3)$_{osb}$ mice (right hand panel). Treatment with M-CSF (FIG. 45B); GM-CSF (FIG. 45D); and G-CSF (FIG. 45F) are shown. Images are 100×. N=6 mice per group. Results are mean±SD and represent at least two independent experiments. *p<0.05 versus WT.
Figure 45B:
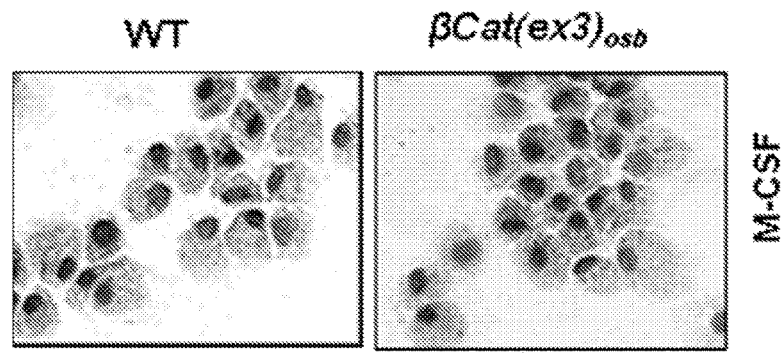
Figure 45C:
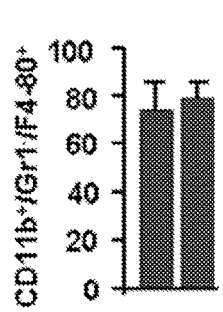
Figure 45D:
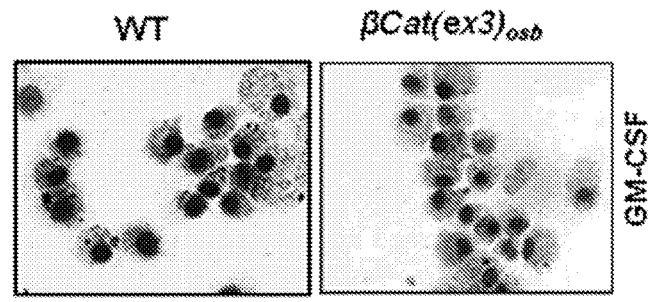
Figure 45E:
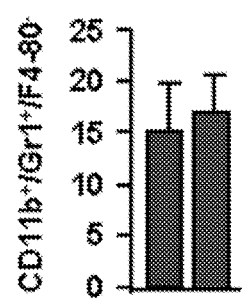
Figure 45F:
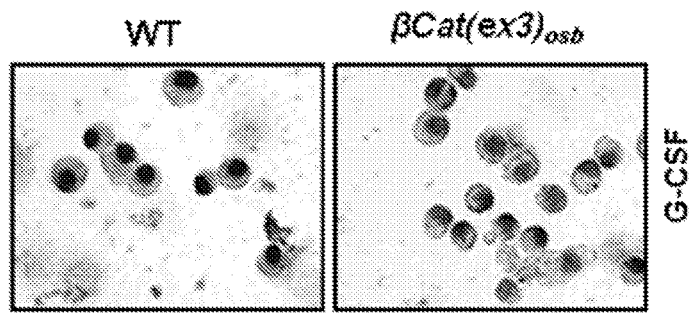
Figure 46A:
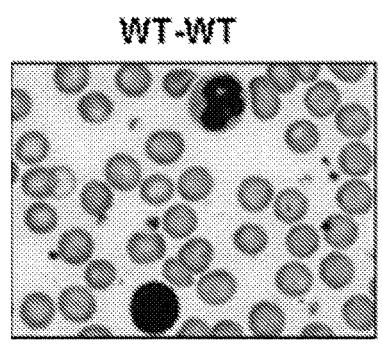
FIG. 46 are peripheral blood smears of wild type (FIG. 46A) and newborn (P1) βCat(ex3)$_{osb}$ mice (FIG. 46B). Images are 100×.
Figure 46B:
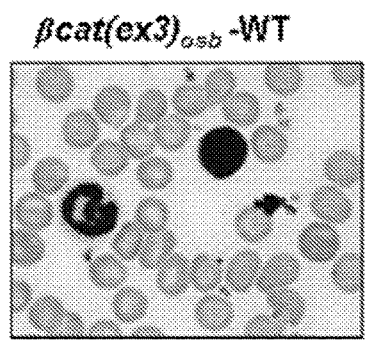

Differentiation blockade was not observed in newborn animals (FIGS. 44 and 45) and fetal HSCs did not transfer the disease (Table 7 and FIG. 46) due to lack of HSC-osteoblast interaction in the fetal liver. These results confirm that AML is induced by defective niche signals that are restricted to the bone marrow osteoblasts.

TABLE 7

Peripheral Blood Measurements in Mice
Transplanted with Newborn cells

|  | WT-WT | βcat(ex3)$_{osb}$-WT |
|---|---|---|
| WBC (×10$^3$/μl) | 4.06 ± 0.4 | 3.86 ± 0.2 |
| HCT (%) | 45.4 ± 4.2 | 46.3 ± 1.4 |
| Platelet (10$^3$/μl) | 1339 ± 83.5 | 1372.2 ± 75.5 |

White blood cells (WBC), Hematocrit (HCT),

Example 9—Constitutive Active β-Catenin Acts Through FoxO1 in Osteoblasts to Induce AML FOXO1 was identified as a molecule that transmits the β-catenin dependent signal from osteoblasts to HSCs.

Materials and Methods

Mice as described in Example 2 were used.

Gene expression and histological analysis were performed as described in Example 1.

Results

FoxO1 physically associated with β-catenin in osteoblasts and expression of β-catenin classical transcriptional targets, Axin2, Tcf1, Tcf3 and Lef1 increased following forced expression of FoxO1 in osteoblasts (FIGS. 47A and 47B). In contrast, expression of the FoxO1 targets cyclin D1, D2, p27Kip1, Superoxide Dismutase 2 (Sod2) and Gadd45 were not affected by forced expression of β-catenin in osteoblasts (FIG. 47C). In vivo expression of Axin2, Tcf1, Tcf3 and Lef1 was decreased in bones from mice with osteoblast-specific inactivation of FoxO1 (FoxO1$_{osb}$−/−) as compared to their wild type littermates (FIG. 47D). In contrast, expression of the FoxO1 targets was not altered in βcat(ex3)$_{osb}$ bone (FIG. 47E). FoxO1 protein levels were not altered in βcat(ex3)$_{osb}$ mice (FIG. 47F).

Taken together, these observations suggest that FoxO1 and β-catenin could form a functional complex in which FoxO1 acts as a coactivator of β-catenin transcriptional activity.

Example 10—FOX1 Deficiency Rescues AML Development in βcat(ex3)$_{osb}$ Mice To investigate whether FoxO1 synergizes with β-catenin in osteoblasts to induce AML in βcat(ex3)$_{osb}$ mice, one FoxO1 allele from osteoblasts of βcat(ex3)$_{osb}$ mice was removed. Indicators of AML were investigated in these mice.

Materials and Methods

βcat(ex3)$_{osb}$ mice with a missing FoxO1 allele from osteoblasts were generated as described in Example 1. These mice were designated βcat(ex3)$_{osb}$;FoxO1$_{osb}$+/− mice.

Hematological measurements, peripheral blood morphology, flow cytometry, PCR, and histological analysis were performed as described in Example 1.

Results

Figure 48G:
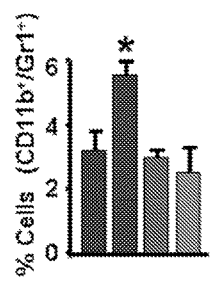
FIG. 48 are graphs depicting various measurements of cell type in WT, βcat(ex3)$_{osb}$,βcat(ex3)$_{osb}$;FoxO1$_{osb}$+/−, and FoxO1$_{osb}$+/− mice, respectively.
FIGS. 48A-E are counts of (A) white blood cells (WBCs); (B) red blood cells (RBCs); (C) Monocytes; (D) Lymphocytes; and (E) Neutrophils in the blood.
FIG. 48F shows the results of flow cytometry analysis and FIG. 48G the percentage of CD11b+/Gr1+ cells, FIG. 48H the percentage of LSK cells, and FIG. 48I the percentage of LT-HSCs, ST-HSCs and MPPs in the bone marrow.
FIGS. 48J-K depict the percentage of myeloid progenitor population in the (J) bone marrow and (K) spleen. n=6 mice per group. *p<0.05 versus WT and #p<0.05 versus βCat(ex3)$_{osb}$;FoxO1$_{osb}$+/−. Results are mean±SD. MNC: mononuclear cells.
Figure 48H:
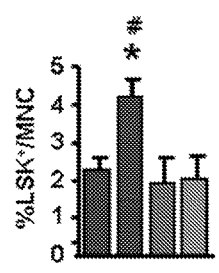
Figure 48I:
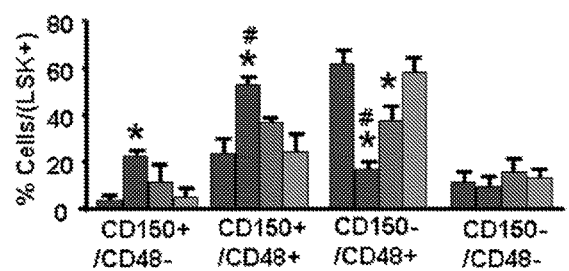
Figure 48J:
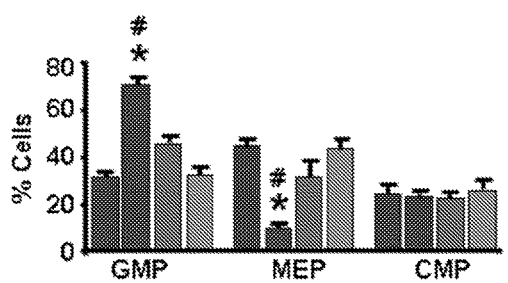
Figure 48K:
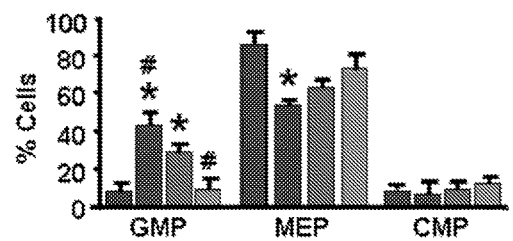
Figure 49A:
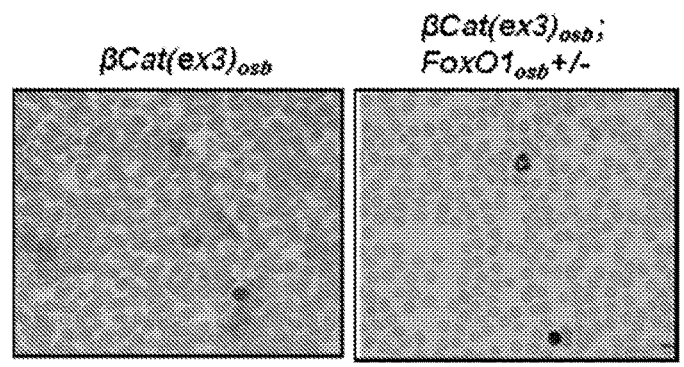
FIGS. 49A and B are peripheral blood smears.
Figure 49B:
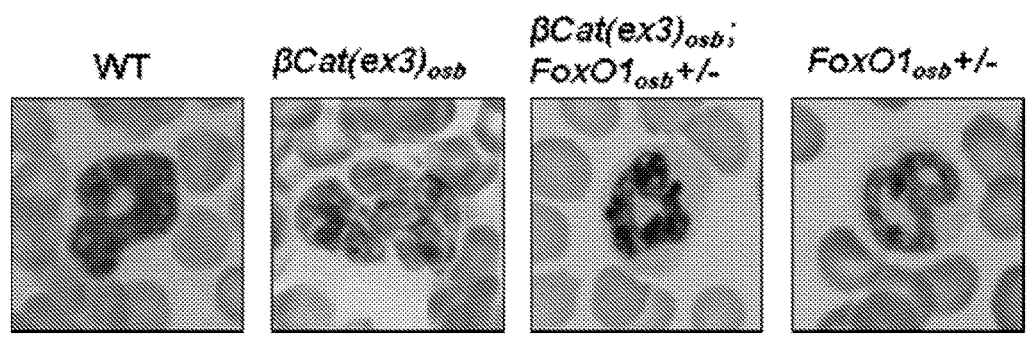
Figure 49C:
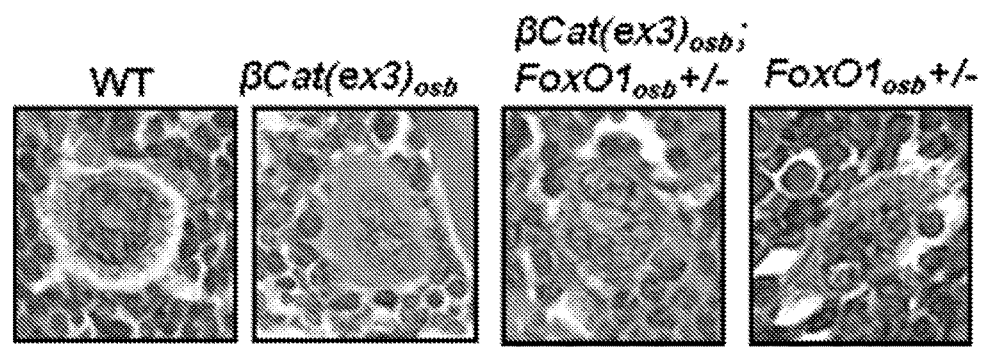
FIG. 49C is bone marrow, FIGS. 49D and E are spleen and a normal histology is seen in βcat(ex3)$_{osb}$;FoxO1$_{osb}$+/− mice.
Figure 49D:
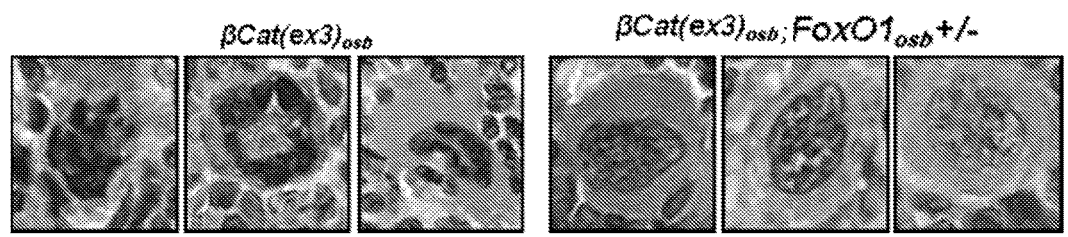
Figure 49E:
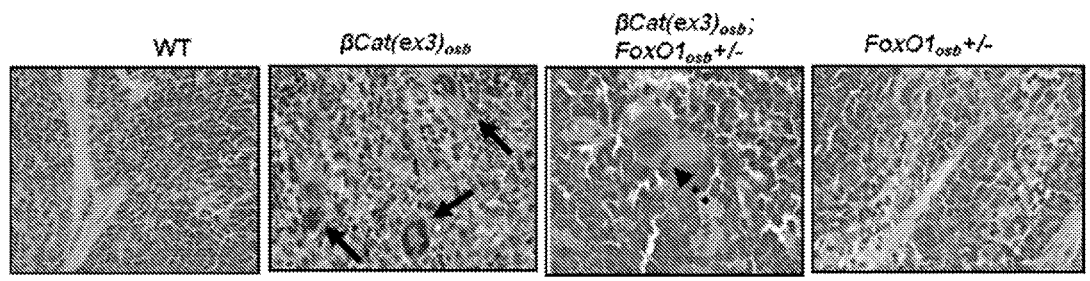
Figure 49F:
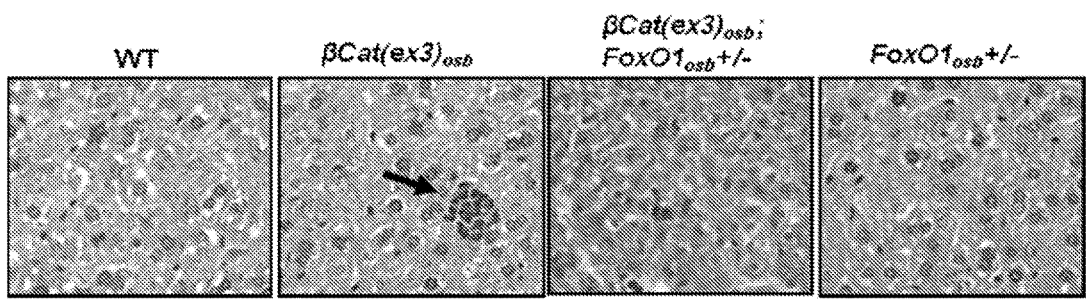
FIG. 49F is the liver, and normal liver histology in βCat(ex3)$_{osb}$;FoxO1$_{osb}$+/− mice. Arrow indicates a cluster of immature cells in βCat(ex3)$_{osb}$ mice.

As shown by the results in Table 8, anemia, peripheral monocytosis, neutrophilia and lymphocytopenia were all corrected in βcat(ex3)$_{osb}$;FoxO1$_{osb}$+/− mice (FIGS. 48A-E). Deregulation of the myeloid and erythroid lineages in the bone marrow and spleen were also rescued (FIGS. 48F and 48G), and the increase in LSK cells and LT-HSCs were reversed in βcat(ex3)$_{osb}$;FoxO1$_{osb}$+/− mice (FIGS. 48H and 48I). Lymphoid-biased multipotential progenitors and myeloid progenitors in the bone marrow and spleen (FIGS. 48J and 48K), returned to normal levels in βcat(ex3)$_{osb}$;FoxO1$_{osb}$+/− mice.

Figure 50A:
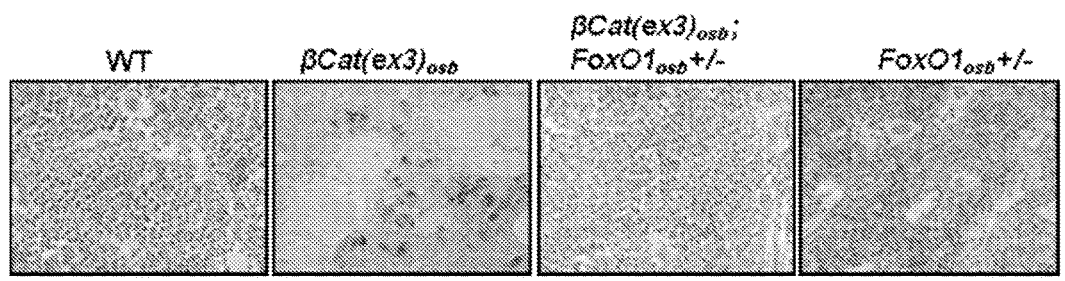
FIG. 50 is myeloperoxidase (MPO) staining of bone marrow (FIG. 50A), spleen (FIG. 50B), and liver (FIG. 50C) of WT (first panels), βcat(ex3)$_{osb}$, (second panels), βcat (ex3)$_{osb}$ FoxO1$_{osb}$+/−, (third panels); and FoxO1$_{osb}$+/− mice (fourth panels) showing massive invasion of myeloid cells in βCat(ex3)$_{osb}$ but not in βCat(ex3)$_{osb}$;FoxO1$_{osb}$+/− littermates. Images were taken at 60× magnification.
Figure 50B:
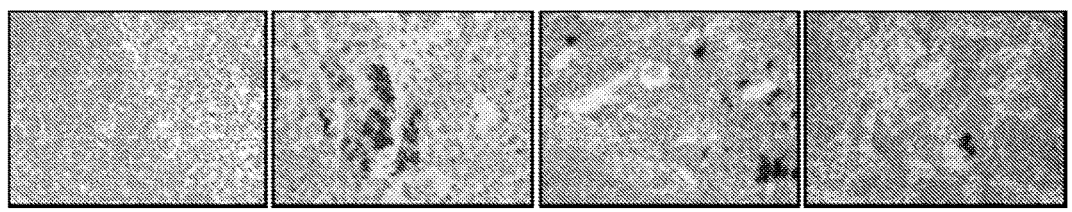
Figure 50C:
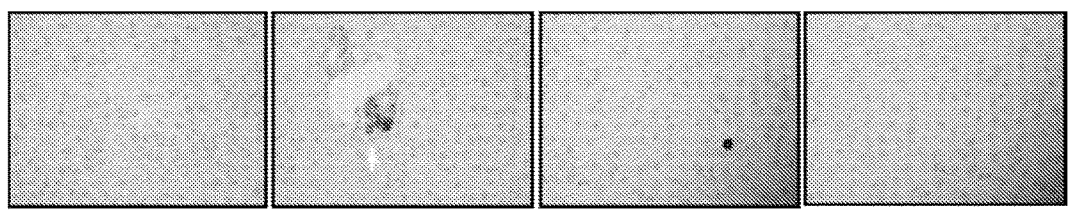
Figure 51A:
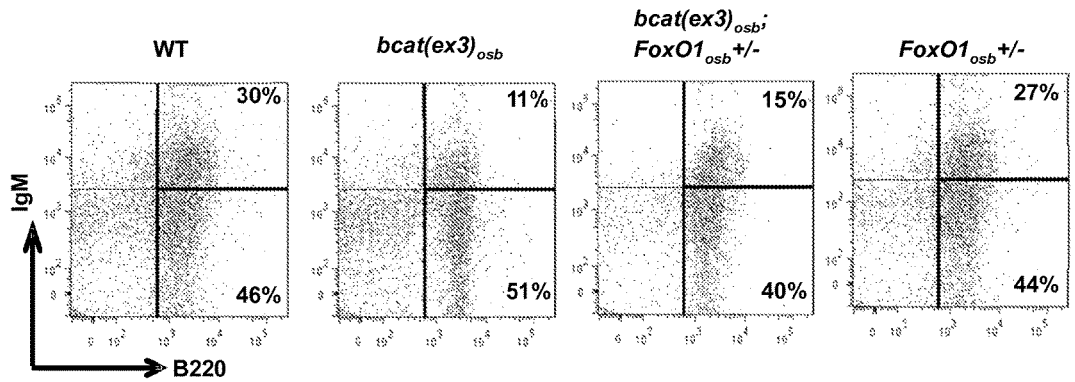
FIG. 51A is representative flow cytometry analysis image showing representative image for B-cell populations in the bone marrow of WT (first panels), βcat(ex3)$_{osb}$, (second panels), βcat(ex3)$_{osb}$ FoxO1$_{osb}$+/−, (third panels), and FoxO1$_{osb}$+/− mice (fourth panels).
Figure 51B:
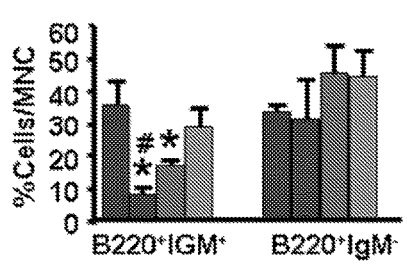
FIG. 51B shows the percentage of B-cell populations in the bone marrow for each type of mouse.
Figure 51D:
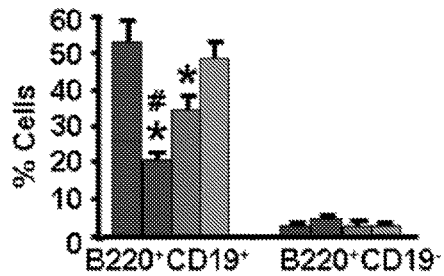
FIG. 51D is the percentage of B-cell populations in the spleen for each type of mouse. n=6 mice per group. *p<0.05 versus WT and #p<0.05 versus βCat (ex3)$_{osb}$;FoxO1$_{osb}$+/−. Results are mean±SD.
Figure 51C:
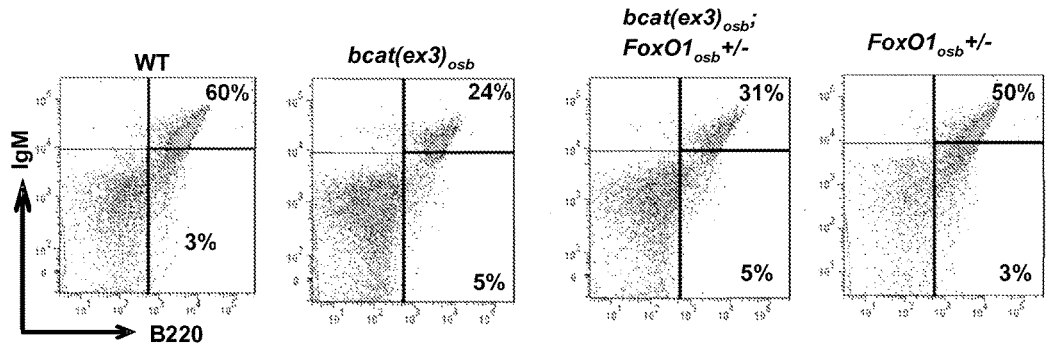
FIG. 51C is flow cytometry analysis showing representative image for B-cell populations in the spleen of WT (First panels), βcat(ex3)$_{osb}$, (second panels), βcat(ex3)$_{osb}$ FoxO1$_{osb}$+/−, (third panels), and FoxO1$_{osb}$+/− mice (fourth panels)
Figure 52:
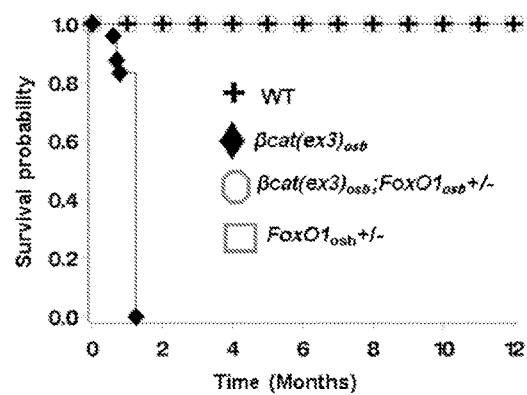
FIG. 52 are Kaplan-Meier survival curves for WT, βcat (ex3)$_{osb}$, βcat(ex3)$_{osb}$;FoxO1$_{osb}$+/−, and FoxO1$_{osb}$+/− mice.

Histological features, such as the presence of monocytic/myeloid cells and dysplastic neutrophils or atypical micro-megakaryocytes in the blood long bones, spleen and liver, associated with the AML phenotype of βcat(ex3)$_{osb}$ mice were also rescued in βcat(ex3)$_{osb}$;FoxO1$_{osb}$+/— animals (FIGS. 49A-F). Myeloperodixase staining in bone marrow, spleen and liver of βcat(ex3)$_{osb}$;FoxO1$_{osb}$+/− mice, was similar to that of wild type animals establishing that leukemogenesis did not occur in these mice (FIGS. 50A-C). B-lymphopoiesis was partially reversed in βcat(ex3)$_{osb}$;FoxO1$_{osb}$+/− mice (FIGS. 51A-D). As a result, βcat(ex3)$_{osb}$;FoxO1$_{osb}$+/− mice survived and remained healthy for at least one year, even though they remained osteopetrotic, hence suggesting that osteopetrosis by itself is not enough to drive AML features (FIG. 52).

Collectively, these results indicate that AML development by constitutive activation of β-catenin in osteoblasts depends on FoxO1.

TABLE 8

Hematopoietic parameters in wild type and βCat(ex3)$_{osb}$, βCat(ex3)$_{osb}$;
FoxO1$_{osb}$+/− and FoxO1$_{osb}$+/− mice at 4 weeks of age

| Parameter | WT | βcat(ex3)$_{osb}$ | βcat(ex3)$_{osb}$; FoxO1$_{osb}$+/− | FoxO1$_{osb}$+/− |
|---|---|---|---|---|
| WBC(×10$^3$/μl) | 3.37 ± 0.4 | 1.31 ± 0.3 | 5.44 ± 0.7 | 3.7 ± 0.6 |
| RBC (×10$^6$/μl) | 6.81 ± 0.5 | 4.79 ± 0.2 | 7.56 ± 0.4 | 7.78 ± 0.2 |
| HB (g/dl) | 10.2 ± 0.6 | 6.40 ± 1.3 | 11.02 ± 1.1 | 11.77 ± 0.8 |
| HCT (%) | 39.25 ± 2.8 | 25.73 ± 3.1 | 34.12 ± 2.5 | 33.32 ± 2.5 |
| Platelet(×10$^3$/μl) | 1290 ± 144.2 | 666.3 ± 87.4 | 1063.2 ± 80.4 | 1548.2 ± 378.4 |
| LY (%) | 72.32 ± 3.8 | 22.57 ± 3.1 | 59.47 ± 1.7 | 72.13 ± 4.9 |
| NE (%) | 21.12 ± 1.6 | 70.34 ± 1.3 | 31.02 ± 5.4 | 23.02 ± 4.4 |
| MO (%) | 5.36 ± 1.1 | 8.9 ± 0.2 | 6.21 ± 2.2 | 5.70 ± 1.6 |
| EO (%) | 1.78 ± 1.3 | 0.20 ± 0.3 | 1.69 ± 1.9 | 0.77 ± 0.24 |
| BA (%) | 0.4 ± 0.3 | 0.25 ± 0.1 | 0.51 ± 0.8 | 0.40 ± .24 |
| BM cell per femur (10$^5$) | 69.8 ± 0.38 | 17.4 ± 0.32 | 41.5 ± 0.28 | 70.2 ± 0.41 |

White blood cells (WBC), Red blood cells (RBC), Hemoglobin (HB) Hematocrit (HCT), lymphocytes (LY), Monocytes (MO), Eosinophils (EO), Basophils (BA)

Example 11—β-Catenin/FoxO1 in Osteoblasts Regulates HSC Function Through Notch Signaling In order to identify β-catenin/FoxO1 targets in osteoblasts that regulate HSC fate, microarray analysis was performed and four criteria were looked for as a target: acts on adjacent cells, activates many targets of which are increased in the array, had been implicated in hematopoiesis, and is regulated transcriptionally by β-catenin.

Materials and Methods

Microarray analysis, flow cytometry, reporter constructs, luciferase assays, and ChIP analysis was performed as described in Example 1.

Results

Figures 53A, 53B, 53C:
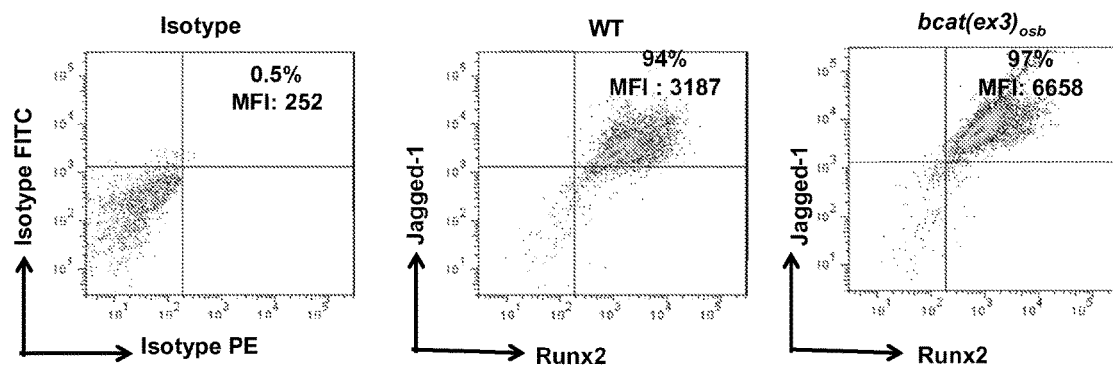
FIG. 53A shows a control.
Figure 54:
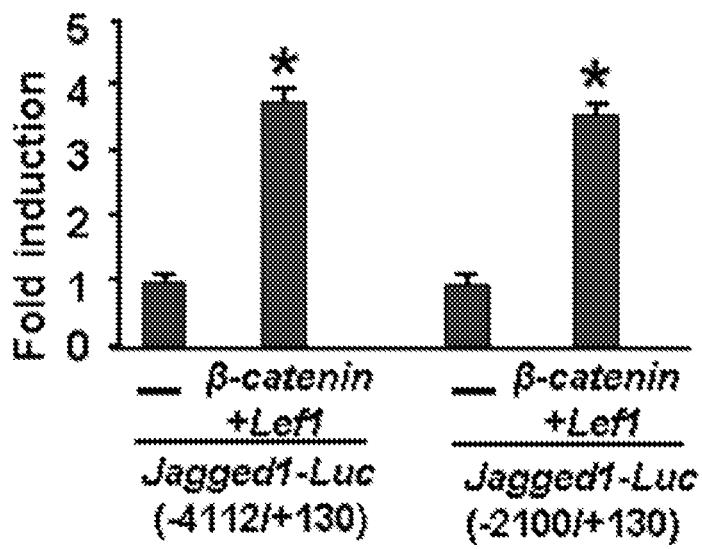
FIG. 54 are graphs of luciferase activity in HEK293T cells co-transfected with β-catenin, Lef1 and Jagged1-Luc reporter constructs (−4112/+130) and (−2100/+130). Results show 4-fold induction over respective Jagged-1 Luc reporter constructs. *p<0.05 versus respective Jagged1-Luc. Results are mean±SD.
Figure 55:
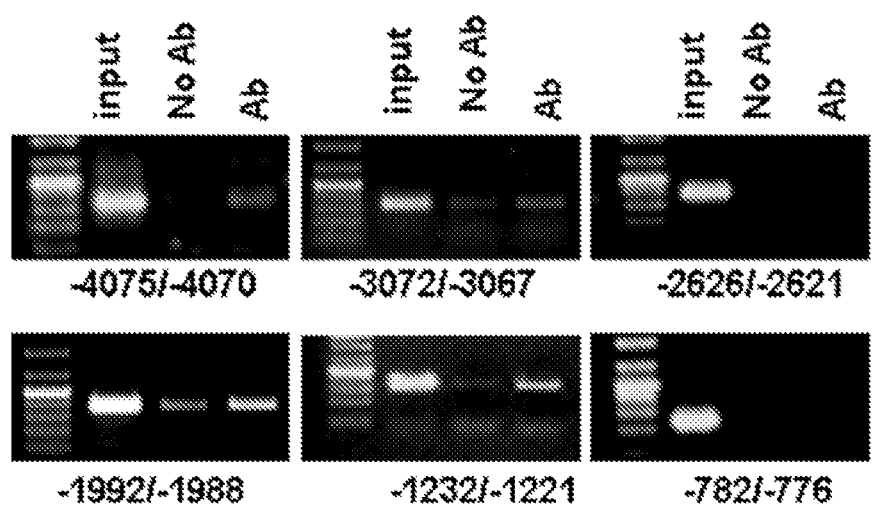
FIG. 55 are results of ChIP analysis in primary osteoblasts using an anti-β-catenin antibody. Primers spanned the putative TCF/LEF binding sites on the Jagged-1 promoter.

The microarray data from βcat(ex3)$_{osb}$ and FoxO1$_{osb}$−/− osteoblasts was performed and compared and it was found that one gene fulfilled the four necessary criteria (Estrich et al. refe 14) (Table 9): the Notch ligand Jagged-1 (FIGS. 53-55).

Figures 56A, 56B, 56C:
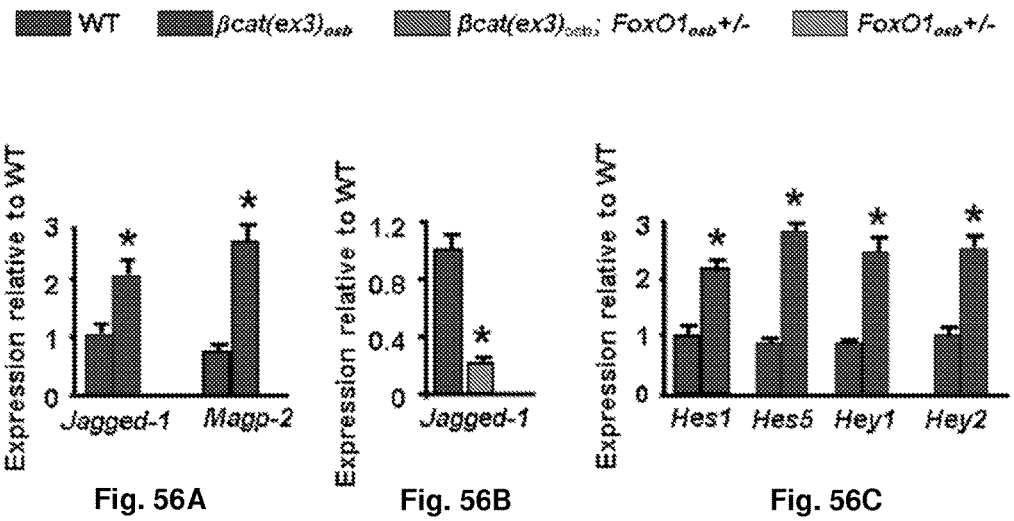
In FIGS. 56A, C, D, E, F, and G, the wild type group is represented by the left hand bar, and the βcat(ex3)$_{osb}$ mice group the right hand bar. In (A-H) n=4 mice per group and *p<0.05 versus WT.

Jagged-1 was upregulated 4-fold in βcat(ex3)$_{osb}$ and downregulated 5-fold in FoxO1$_{osb}$−/− compared to wild type osteoblasts. Accordingly, expression of Jagged-1 increased in βcat(ex3)$_{osb}$ bones and decreased in FoxO1$_{osb}$−/− bones (FIGS. 56A and 56B). In addition, expression of microfibril-associated glycoprotein 2 (Magp-2/Mfap-5), a gene encoding an extracellular matrix protein facilitating shedding of Jagged-1 from the cell membrane, was upregulated in βcat(ex3)$_{osb}$ bones (FIG. 56A).

Materials and Methods

βcat(ex3)$_{osb}$ mice, βcat(ex3)$_{osb}$;FoxO1$_{osb}$+/− mice, and FoxO1$_{osb}$+/− mice as described in Example 1 were used.

Gene expression, reporter constructs, and luciferase assays were performed as described in Example 1.

Results

Figures 56D, 56E:
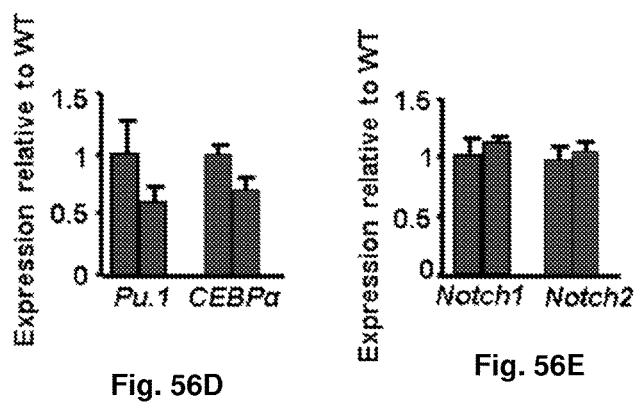
FIG. 56 show expression levels of (A) Jagged-1 and Magp-2 in WT (left hand bar) and βCat(ex3)$_{osb}$ (right hand bar) in bone; (B) Jagged-1 in WT (left hand bar) and FoxO1$_{osb+}$/− bone (right hand bar); (C) Hes1, Hes5, Hey1 and Hey2; (D) Pu.1 and CEBPα; and (E) Notch1 and Notch2 in LSK+ cells of WT and βCat(ex3)$_{osb}$.
FIG. 56F expression of Hes1 and FIG. 56G, Hes5 in LSK+ subpopulations of WT and βCat(ex3)$_{osb}$.

Expression of the Notch targets Hes1, Hes5, Hey1, and Hey2, was upregulated in βcat(ex3)$_{osb}$ LSK cells suggesting increased Notch signaling in this population (FIG. 56C). Consistent with this hypothesis, expression of the Hes1 targets, Cebpα and Pu.1 decreased in βcat(ex3)$_{osb}$ LSK cells (FIG. 56D). Notch1 and 2 expression was not affected in βcat(ex3)$_{osb}$ LSK cells suggesting that Notch signaling, rather than Notch expression is upregulated in these cells (FIG. 56E).

Figures 56F, 56G:
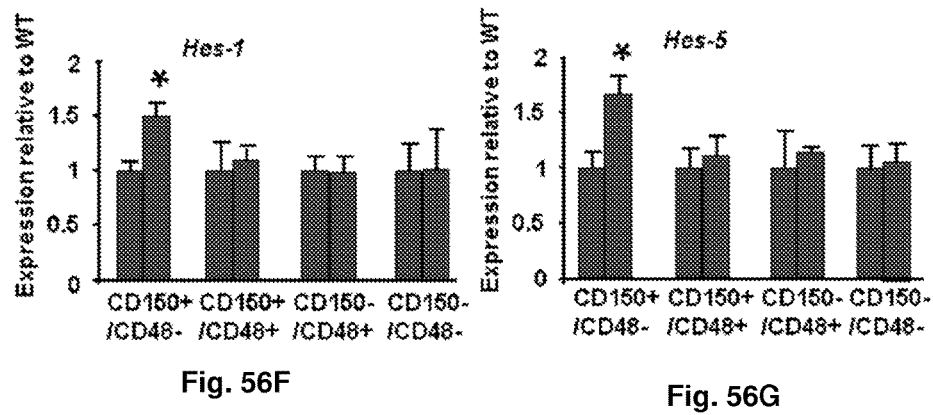

Similar to the reversal of LSK expansion, removal of one FoxO1 allele from osteoblasts of βcat(ex3)$_{osb}$ mice reversed the increase in Hes1 expression indicating that β-catenin and FoxO1 interact in osteoblasts to regulate HSC lineage commitment through Notch signaling. Expression of Notch targets and Notch signaling was increased in leukemia-inducing LT-HSCs but was not affected in any of the other LSK subpopulations (FIGS. 56F and G) suggesting that augmented Notch signaling occurs in the LT-HSCs compartment and the changes in the other LSK compartments are the outcome of augmented Notch signaling in HSCs. In support of this proposed model, there was no change in Notch signaling in HSC of βcat(ex3)$_{osb}$;FoxO1$_{osb}$+/− mice.

TABLE 9

Results of Microarray Analysis of βcat(ex3)$_{osb}$ osteoblasts

| Probe id | Gene symbol | Gene Title | βCat(ex3)$_{osb}$ Vs WT log2 Fold Change | βCat(ex3)$_{osb}$ % Change | βCat(ex3)$_{osb}$ Vs Wt P. Value |
|---|---|---|---|---|---|
| 1440397_at | Cacna2d1 | calcium channel, voltage-dependent, alpha2/delta subunit 1 | 0.51 | 43 | 7.E−02 |
| 1415999_at | Hey1 | hairy/enhancer-of-split related with YRPW motif 1 | 1.51 | 184 | 3.E−04 |
| 1421105_at | Jag1 | jagged 1 | 0.30 | 23 | 1.E−01 |
| 1449082_at | Mfap5/Magp-2 | microfibrillar associated protein 5 | 0.31 | 24 | 7.E−01 |
| 1453956_a_at | Pftk1 | PFTAIRE protein kinase 1 | 0.14 | 10 | 7.E−01 |
| 1418102_at | Hes1 | hairy and enhancer of split 1 (Drosophila) | 0.43 | 35 | 1.E−01 |
| 1432189_a_at | Sox5 | SRY-box containing gene 5 | 0.55 | 46 | 4.E−02 |
| 1418454_at | Mfap5/Magp-2 | microfibrillar associated protein 5 | 0.10 | 7 | 9.E−01 |
| 1417542_at | Rps6ka2 | ribosomal protein S6 kinase, polypeptide 2 | 0.28 | 22 | 6.E−02 |
| 1419250_a_at | Pftk1 | PFTAIRE protein kinase 1 | −0.37 | −0.23 | 2.E−02 |
| 1418106_at | Hey2 | hairy/enhancer-of-split related with YRPW motif 2 | 0.36 | 29 | 8.E−02 |
| 1427677_a_at | Sox6 | SRY-box containing gene 6 | −0.23 | −14 | 1.E−01 |

Example 12—Further Evidence that β-Catenin/FoxO1 in Osteoblasts Regulates HSC Function Through Notch Signaling In view of the results reported in Example 11, it was asked whether constitutive activation of β-catenin and the FoxO1/β-catenin interaction in osteoblasts affects Notch signaling in LSK cells, the affected hematopoietic population.

A close inspection of the DNA sequence of Jagged-1 promoter region revealed the presence of multiple potential TCF/LEF (C/TCTTTG) and FoxO1 (TGTTTT) elements located up to nucleotide −4075 (TCF-1: −4075, −3072, −2626, −2578, −2343, −1992, 1957, −1566, −1221, −782; FoxO1: −3875, −3861, −3270, −2805, −2442, −2048, −1847, −1835, −1430, −1294). The biological importance of these sites was examined by transient transfection assays.

Since, TCF1 and LEF1 share 75 out of 78 identical amino acid residues in their DNA binding domains (HMG boxes) and bind to the same consensus motif, an expression vector for LEF-1 was used as a prototype of LEF/TCF proteins, to measure activation by Jagged-1. While overexpression of β-catenin/LEF-1 or FoxO1 alone could not transactivate the Jagged-1 promoter, coexpression of both proteins stimulated its activity by 5-fold (FIG. 57A). Deletion mutants of Jagged-1 promoter lacking half of the TCF and FoxO1 responsive elements were equally responsive to the β-catenin/LEF-1/FoxO1 overexpression suggesting that the proximal promoter region is essential for the upregulation by β-catenin/LEF-1 and FoxO1. Thus, β-catenin and FoxO1 co-operatively promote the expression of Jagged-1.

Consistent with these data, treatment of primary osteoblasts with Wnt3a upregulated expression of Jagged-1 and Magp-2 (FIG. 57B). Moreover, treatment with Wnt3a stimulated Notch signaling in LSK cells cultured in the presence of primary osteoblasts (FIG. 57C). Taken together, these observations suggest that β-catenin activation in osteoblasts in synergy with FoxO1 induces expression of Notch ligands which in turn trigger downstream activation of Notch signaling in adjacent HSCs.

Example 13—Inhibition of Notch Signaling Reverses Leukemia in βcat(ex3)$_{osb}$ Mice Since AML development is caused by constitutive activation of β-catenin in osteoblasts due to activation of Notch signaling in hematopoietic progenitors, then the inhibition of Notch signaling in βcat(ex3)$_{osb}$ mice should rescue the AML phenotype.

Materials and Methods

βcat(ex3)$_{osb}$ mice as described in Example 2 were treated for 10 days with DBZ, a γ-secretase inhibitor with Notch inhibitory activity in vivo (Real et al., 2009; Pajvani et al., 2011), as described in Example 1.

Hematological measurements, peripheral blood morphology, flow cytometry, PCR, and histological analysis were performed as described in Example 1.

Results

Mice were treated with DBZ without any toxic effects as intestinal architecture was normal with absence of goblet cell metaplasia (FIG. 58).

Figures 60E, 60F, 61C:
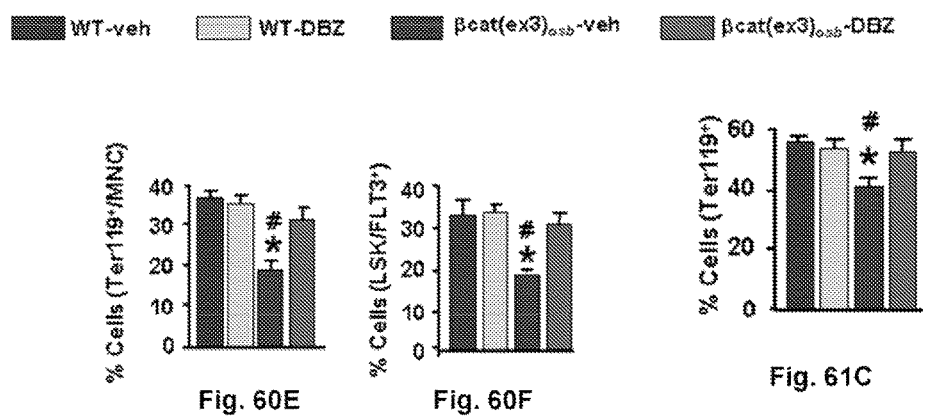
FIG. 60E shows percentage of erythroid cells.
FIG. 60F shows LSK+/FLT3+ population. N=8 mice per, group. *p<0.05 versus WT vehicle and #p<0.05 compared βCat(ex3)$_{osb}$-vehicle versusβCat (ex3)$_{osb}$-DBZ group. Results are mean±SD.
FIG. 61C shows erythroid cells, in WT mice treated with a vehicle, WT mice treated with DBZ, βcat(ex3)$_{osb}$ treated with a vehicle, and βcat(ex3)$_{osb}$ treated with DBZ, all in the spleen, respectively. n=8 mice per group. *p<0.05 versus WT vehicle and #p<0.05 compared βCat(ex3)$_{osb}$-vehicle versus βCat(ex3)$_{osb}$-DBZ group. Results are mean±SD.
Figures 61A, 61B:
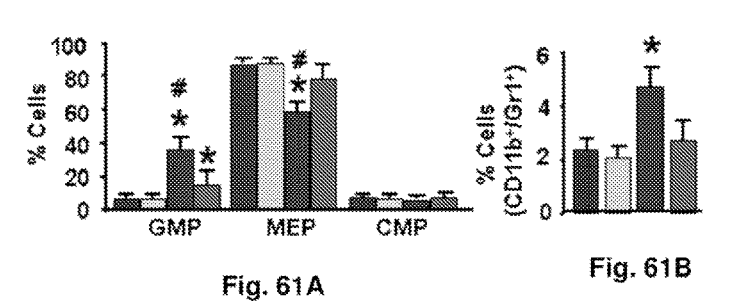
FIG. 61A shows percentages of myeloid progenitors.
FIG. 61B shows CD11b+/Gr1+ myeloid cells.

Moreover, DBZ reversed anemia, peripheral monocytosis, neutrophilia and lymphocytopenia in βcat(ex3)$_{osb}$ mice (Table 10, FIGS. 59A and B). Bone marrow cellularity was not affected (Table 10). DBZ also reversed the defects in the myeloid lineage, erythroid cells, LSK and LT-HSCs populations in the bone marrow (FIG. 60) and spleen (FIG. 61). LSK and the lymphoid-biased progenitors in the bone marrow and the LSK/FcgRII/III subset of myeloid progenitors in the spleen and bone marrow returned to normal levels following treatment of βcat(ex3)$_{osb}$ mice with DBZ (FIGS. 60 and 61).

Figures 62A, 62B:
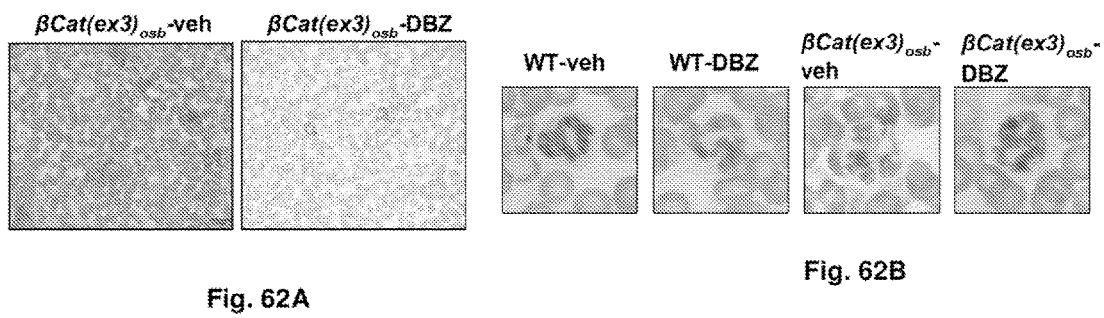
FIGS. 62A and 62B are peripheral blood smears (Wright and Giemsa)
Figure 62C:
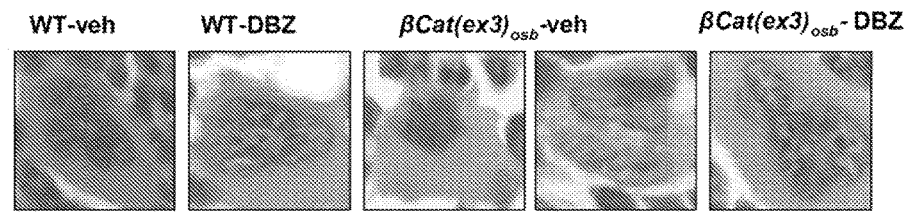
FIG. 62C are bone marrow.
Figure 62D:
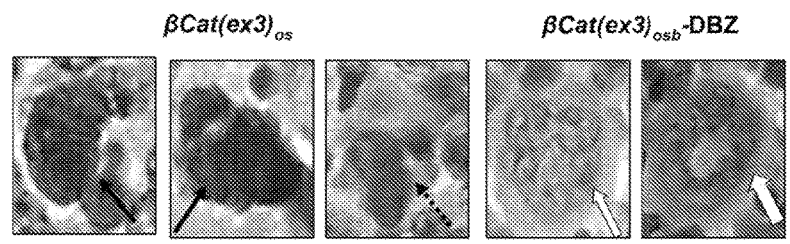
FIGS. 62D and 62E are spleen.
Figure 62E:
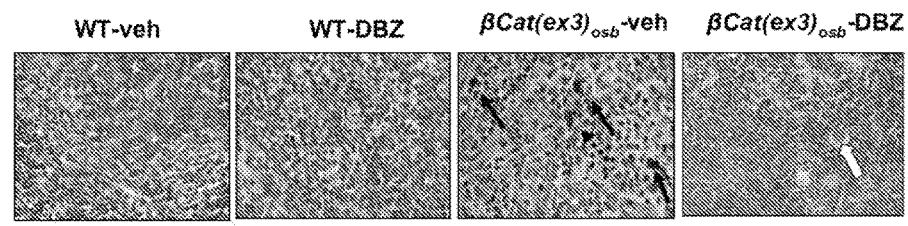
Figure 62F:
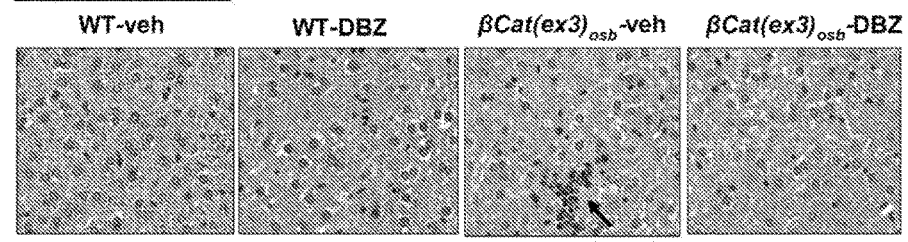
FIG. 62F are liver.
Figure 68D:
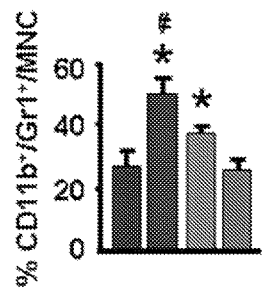
FIG. 68D shows CD11b+/Mac 1+ cells.
Figure 68E:
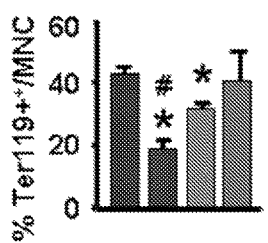
FIG. 68E shows erythroid progenitors.
Figure 68F:
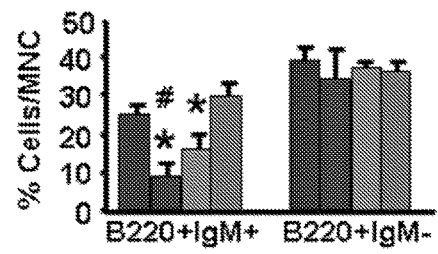
FIG. 68F shows B-lymphoid cells.
Figure 68G:
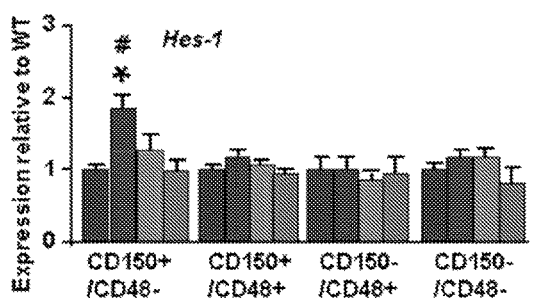
FIGS. 68G-J show the expression of Notch transcriptional targets, Hes-1 (68G), Hes-5 (68H), Hey-1 (68I) and Hey2 (68J), in bone marrow LSK subpopulations. n=6 mice per group *p<0.05 versus WT and #p<0.05 compared βCat(ex3)$_{osb}$ versus βcat(ex3)$_{osb}$;Jagged1$_{osb}$+/− mice. Results are mean±SD and show mean of three experiments.
Figure 68H:
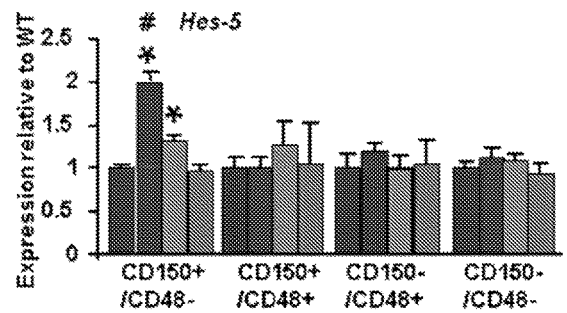
Figure 68I:
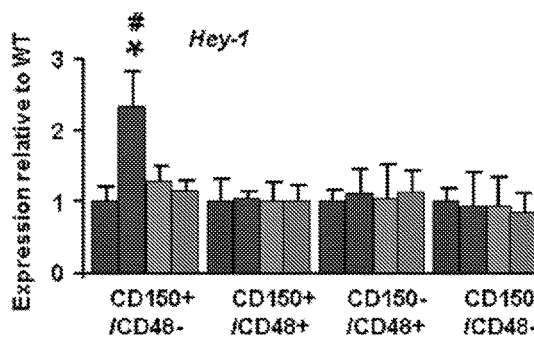
Figure 68J:
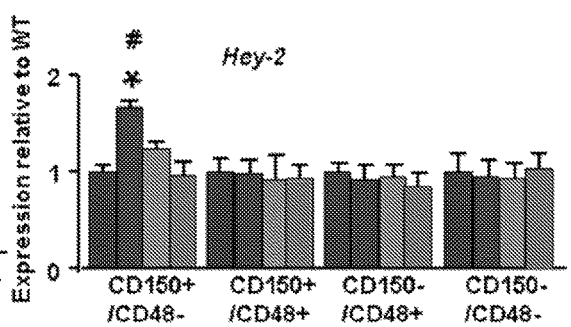

Blasts and hypersegmented neutrophils in the blood (FIGS. 62A and B) and infiltration with immature and atypical myeloid cells and atypical micro-megakarycotes in the bone marrow and spleen (FIGS. 62C-E) were not observed in βcat(ex3)$_{osb}$ animals following treatment with DBZ. Liver histology of DBZ-treated βcat(ex3)$_{osb}$ animals appeared normal (FIG. 62F). Myeloperodixase-staining in bone marrow, spleen and liver of DBZ-treated βcat(ex3)$_{osb}$ mice was identical to that of wild type animals, establishing that myeloid leukemia was inhibited (FIGS. 63A-C; FIG. 64). These samples show massive invasion of myeloid cells in βCat(ex3)$_{osb}$ but not in DBZ-treated βCat(ex3)$_{osb}$ mice. Treated mice also had increased survival (FIG. 65).

Moreover, compromised B-lymphopoiesis was partially rescued by inhibition of Notch signaling in βcat(ex3)$_{osb}$ mice (FIGS. 66A-D). The osteopetrotic phenotype of βcat (ex3)$_{osb}$ mice was not affected by DBZ treatment (FIG. 67), further indicating that osteopetrosis is not the cause of AML in βcat(ex3)$_{osb}$ mice.

TABLE 10

Peripheral blood counts and bone marrow cellularity in wild type and βCat(ex3)$_{osb}$ mice treated daily with vehicle or DBZ (2 µmol/kg body weight) for 10 days.

| Parameter | WT-Vehicle | WT-DBZ | βcat(ex3)$_{osb}$-Vehicle | βcat(ex3)$_{osb}$-DBZ |
|---|---|---|---|---|
| WBC(×10$^3$/µl) | 3.38 ± 0.4 | 3.54 ± 0.5 | 2.15 ± 1.2 | 3.1 ± 0.5 |
| RBC (×10$^6$/µl) | 9.16 ± 0.2 | 9.49 ± .0.3 | 5.12 ± 0.2 | 8.06 ± 0.5 |
| HB (g/dl) | 13.1 ± 0.4 | 12.8 ± 0 | 6.19 ± 0.5 | 11.2 ± 0.9 |
| HCT (%) | 43.25 ± 1.4 | 45.90 ± 2.5 | 29.2 ± 1.2 | 36.75 ± 3.2 |
| Platelet(10$^3$/µl) | 1244.5 ± 53.1 | 1119.5 ± 68.5 | 625.7 ± 114.6 | 650 ± 113.1 |
| LY (%) | 74.14 ± 6.1 | 78.54 ± 3.2 | 25.79 ± 1.5 | 49.76 ± 4.3 |
| NE (%) | 17.9 ± 4.8 | 14.41 ± 3.2 | 62.27 ± 3.1 | 42.21 ± 4.8 |
| MO (%) | 6.19 ± 0.8 | 5.01 ± 0.6 | 9.77 ± 0.2 | 7.46 ± 1.2 |
| EO (%) | 1.43 ± 0.3 | 1.55 ± 0.2 | 0.52 ± 0.6 | 1.87 ± 1.6 |
| BA (%) | 0.34 ± 0.1 | 0.5 ± 0.2 | 0.28 ± 0.3 | 0.67 ± 0.7 |
| BM cell per femur (10$^5$) | 75.2 ± 2.3 | 71.5 ± 4.3 | 17.3 ± 1.2 | 18.6 ± 3.5 |

White blood cells (WBC), Red blood cells (RBC), Hemoglobin (HB), Hematocrit (HCT), platelets lymphocytes (LY), Monocytes (MO), Eosinophils (EO), Basophils (BA), Bone Marrow (BM).

Example 14—Further Evidence on the Involvement of Notch Signaling

To establish genetically the involvement of Notch signaling it was asked whether Jagged-1 in osteoblasts contributes to AML development in Bcat(ex3)$_{osb}$ mice.

Materials and Methods

Compound mice constitutively expressing β-catenin in osteoblasts and lacking one allele of Jagged-1 in osteoblasts (βcat(ex3)$_{osb}$;Jagged1$_{osb}$+/−) were generated as described in Example 1.

Hematological measurements, peripheral blood morphology, flow cytometry, PCR, and histological analysis were performed as described in Example 1.

Results

Figure 69A:
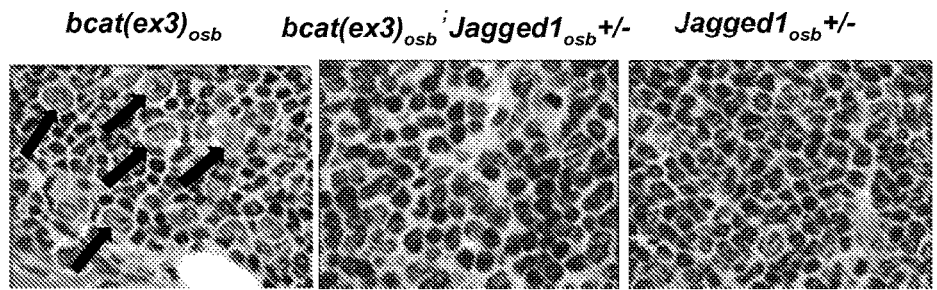
FIG. 69A are histological sections of normal blood in βcat(ex3)$_{osb}$;Jagged1$_{osb}$+/−mice.
Figure 69B:
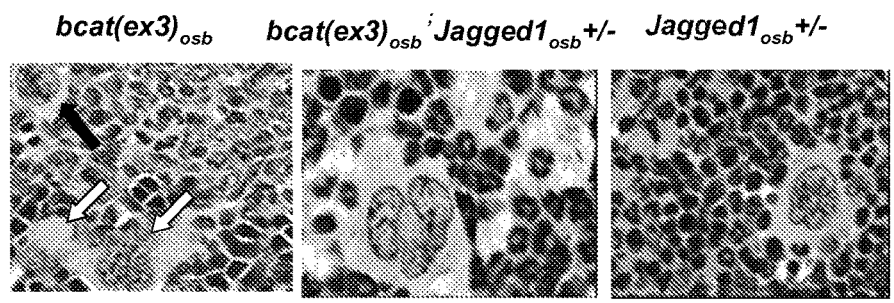
FIG. 69B shows bone marrow.
Figure 69C:
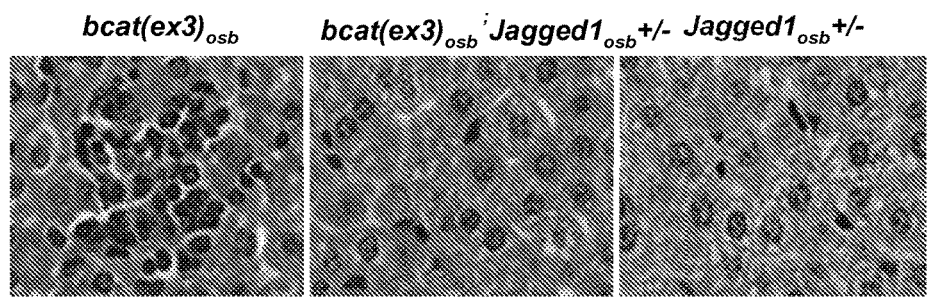
FIG. 69C shows spleen in βcat(ex3)$_{osb}$, βcat(ex3)$_{osb}$;Jagged1$_{osb}$+/− and Jagged1$_{osb}$+/−mice.
Figure 70:
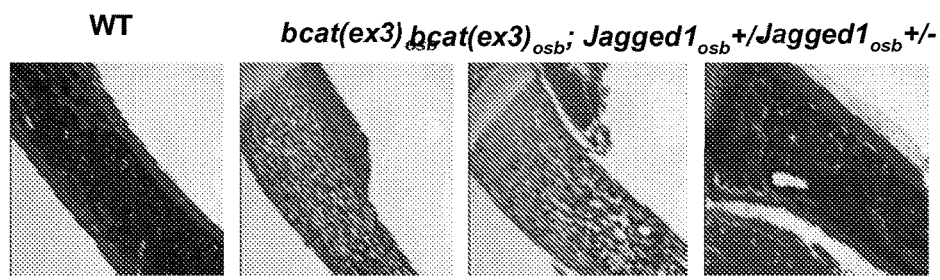
FIG. 70 are long bone sections imaged at 60× of WT mice βcat(ex3)$_{osb}$, βcat(ex3)$_{osb}$;Jagged1$_{osb}$+/− and Jagged1$_{osb}$+/− mice.

The genetic perturbation improved the hematopoietic dysfunction and leukemogenesis of osteoblast-activated β-catenin. Anemia, increased LSK numbers and deregulation of HSC lineage differentiation were all rescued in βcat(ex3)$_{osb}$;Jagged1$_{osb}$+/− mice (FIG. 68). Blasts were not detected and neutrophils were normal in the blood (FIG. 69A); and, the bone marrow, spleen and liver were free from blasts and dysplastic cells (FIGS. 69B-D) in βcat(ex3)$_{osb}$; Jagged1$_{osb}$+/− mice. βcat(ex3)$_{osb}$;Jagged1$_{osb}$+/− mice survived and were healthy for the entire time they were observed, although they were osteopetrotic (FIGS. 68, 69, and 70).

Taken together both pharmacological and genetic experiments support the hypothesis that Notch signaling is required for AML development caused by constitutive activation of β-catenin in osteoblasts.

Example 15—Nuclear Accumulation of β-Catenin in Osteoblasts Derived from MDS and AML Patients In an effort to add further relevance to the findings in mouse models to human MDS or AML, the cellular localization and activation of β-catenin signaling in bone marrow biopsies from MDS or AML patients was examined.
Materials and Methods A total of 107 biopsies from all MDS subtypes, AML, or MDS that had transformed to AML and 56 healthy controls were analyzed by immunohistochemistry (IHC) and immunofluorescence (IFC) in combination with confocal imaging as described in Example 1.

Flow cytometry and PCR was performed as described in Example 1.
Results

Figure 72C:
FIG. 72C shows membrane β-catenin staining in a healthy control.
Figure 73A:
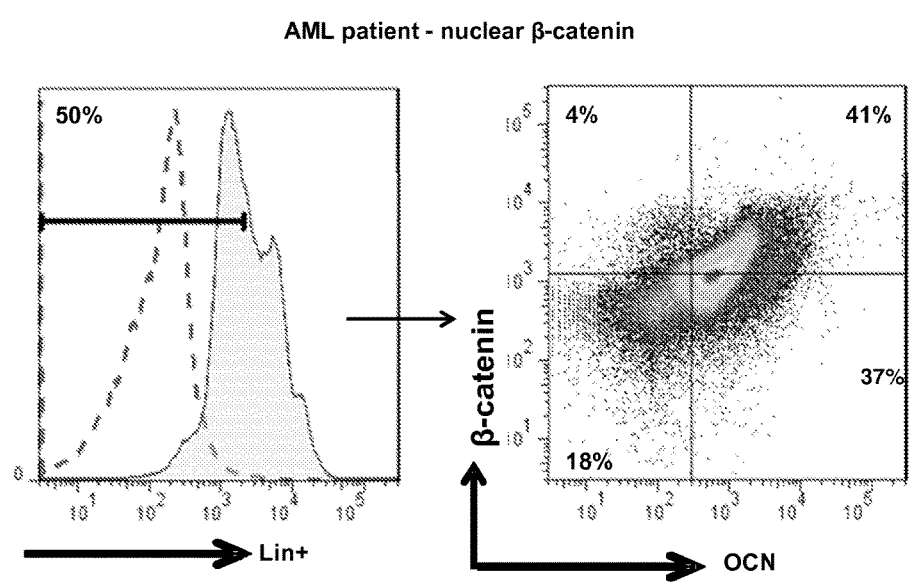
FIG. 73A shows an AML patient with nuclear β-catenin.
Figure 73B:
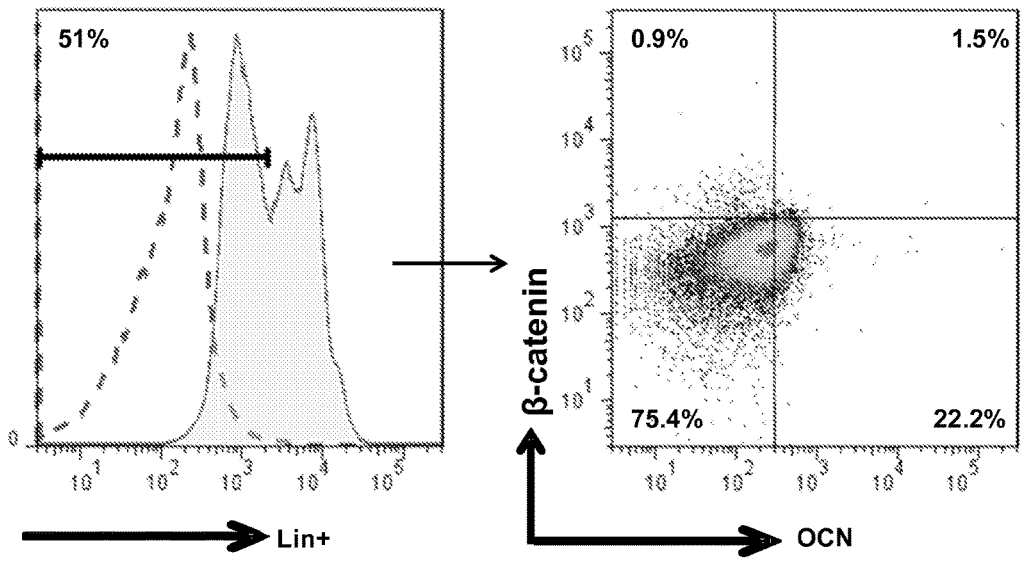
FIG. 73B shows an AML patient with membrane β-catenin.
Figure 73C:
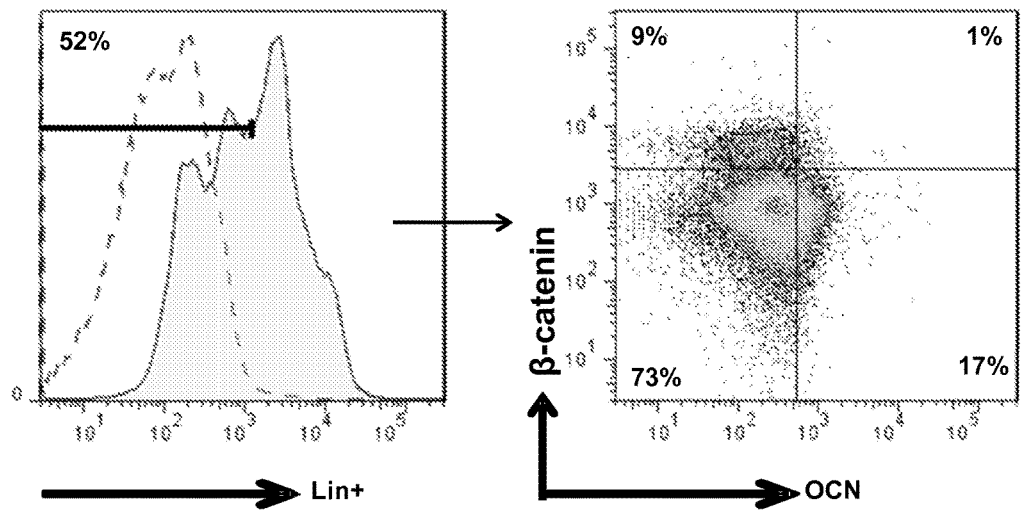
FIG. 73C shows a healthy control with membrane β-catenin.
Figure 76:
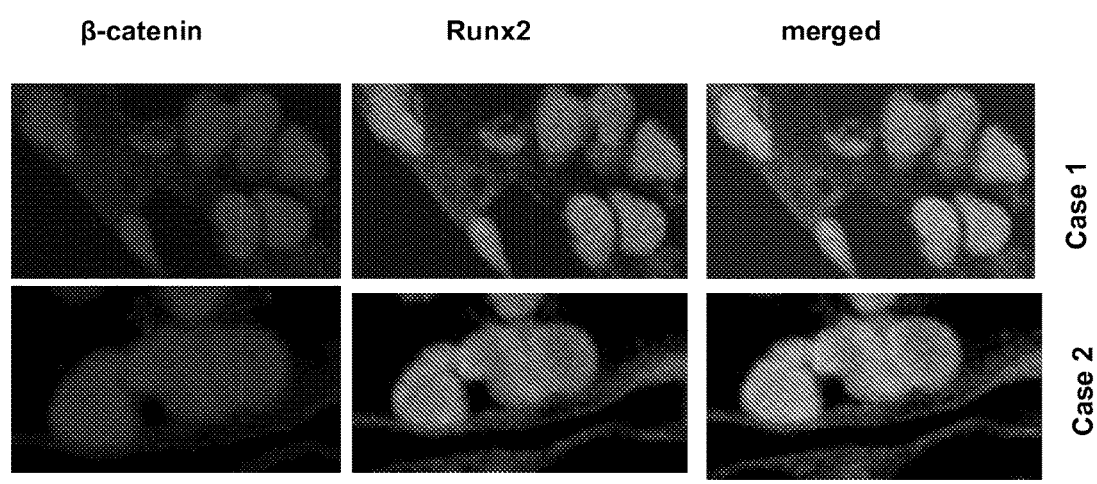
FIG. 76 are double immunofluorescence staining of osteoblasts with β-catenin (left panels) and Runx2 (middle panels) merged images on Runx2 and β-catenin (right panel) in bone marrow biopsies from the two patients first thought to be healthy controls but re-assessed has having MDS (Case 1—top panel) and MPN/MDS (Case 2—bottom panel). Images are 60×.

Forty-one out of 107 patients (38.3%) examined showed nuclear localization of β-catenin in osteoblasts (FIGS. 71-73, Table 11) but none of the fifty-six healthy controls showed this (FIGS. 71-73).

A preferential shift toward the higher risk cases was noted in the 38.3% of patients with malignancy-associated osteoblasts as compared to the remaining subjects examined. Specifically, β-catenin localized to the nucleus of osteoblasts in 16 of 45 patients with MDS (35%), 13 of 36 patients with AML (36%), and 12 of 26 patients (46%) with AML that arose from a prior MDS (Table 11). This was in contrast to membrane localization in osteoblasts of all healthy controls and the remaining 61.7% of patients (FIG. 72). Myeloid and erythroid cells and megakaryocytes in all test samples and in healthy controls showed membrane and cytoplasmic staining for β-catenin (FIGS. 71C and D, 72B and C, and 73B and C).

Flow cytometry using a non-phospho β-catenin antibody detecting nuclear/activated β-catenin verified nuclear accumulation of the protein in osteoblasts from the same 38.3% patients identified by IHC and IFC (FIG. 73). Moreover, 36% of patients with nuclear localization of β-catenin in osteoblasts had abnormalities of chromosome 5 and/or 7, the most common cytogenetic abnormalities observed in patients with MDS and AML (Graubert and Walter, 2011; Raza and Galili, 2012); and β-catenin nuclear staining was notably present in osteoblasts in 42% of the patients with abnormalities of chromosomes 5 and 7.

Notch signaling was specifically activated only in patients with nuclear accumulation of βcatenin as indicated by Hey-1 nuclear staining in their hematopoietic cells (FIG. 74).

The expression of β-catenin target genes and Notch ligands in osteoblasts of MDS and AML patients was also examined and the Notch signaling activity in leukemic cells isolated from these patients assessed. Expression of all examined β-catenin target genes and of JAGGED-1 and DLL-1 was upregulated in osteoblasts from MDS/AML patients that showed β-catenin nuclear localization in osteoblasts, but not in healthy controls (FIGS. 75A and B). Expression of Notch transcriptional targets was also increased two fold in hematopoietic cells from the same patients, but not in healthy controls (FIG. 75C).

TABLE 12

Summary of Two individuals re-evaluated and shown to have MDS and MPN/MDS

| ID | Diagnosis | Cytogenetics | B-catenin nuclear localization (% nuclear) | Age (years) |
|---|---|---|---|---|
| Case 1 | RAEB-1 | Normal | Y (21%) | 73 |
| Case 2 | MPN | V617F JAK2 | Y (28%) | 75 |

TABLE 11

β-Catenin Cellular Localization in Patients with MDS, AML, and AML arising from prior MDS with Associated Cytogenetic Abnormalities

| Patient ID | Diagnosis | Cytogenetics | β-catenin nuclear localization (% Nuclear) | Age (years) |
|---|---|---|---|---|
| 1 | AML | 45, XX, add(2)(p13), add(3)(q26.2), [g]/45, idem, add(7)(46, XX [20] | Y (25%) | 82 |
| 2 | AML | 47, XY, +8[10]/46, XY[10] | Y (38%) | 70 |
| 3 | AML | 46, XY[20] | Y (27%) | 72 |
| 4 | AML | 42-43, XY, del(1)(q11), −3, del(5)(p13), −6, −7, −8, add(9)(p22), −12, −17, −18, | Y (14%) | 48 |
| 5 | AML | 46, XY, t(2; 8)(q37; q22) two copies of chromosome 16q22 | Y (26%) | 66 |
| 6 | AML | 47, XY, add(5)(p13), +13 [2] 46, XY, add(5)(p13) [14] | Y (33%) | 57 |
| 7 | AML | Add (5p), trisoray 13 | Y (25%) | 44 |
| 8 | AML | NL | Y (30%) | 49 |
| 9 | AML | 46, XX{20} | Y (80%) | 68 |
| 10 | AML | NL | Y (37%) | 64 |
| 11 | AML | NL | Y (46%) | 62 |
| 12 | AML | NL | Y (35% | 69 |
| 13 | AML | NL | Y (25%) | 62 |
| 14 | AML from MDS | 47, XY, del(7)(q22), +21 [11] | Y (17%) | 73 |

TABLE 11-continued

β-Catenin Cellular Localization in Patients with MDS, AML, and
AML arising from prior MDS with Associated Cytogenetic Abnormalities

| Patient ID | Diagnosis | Cytogenetics | β-catenin nuclear localization (% Nuclear) | Age (years) |
|---|---|---|---|---|
| 15 | AML from MDS | 47, XY, +8 [12] | Y (32%) | 73 |
| 16 | AML from MDS | 46, XY, del(5)(q13q31), del(20)(q11.2q12) | Y (30%) | 74 |
| 17 | AML from MDS | 46-49, XY, +1, del(5)(q15q31), del(7)(q22q32), +6, +8 | Y (24%) | 60 |
| 18 | AML from MDS | 44-45, XX, −1, −2, t(3; 4)(p21; q35), del(5)(q15q31), hsr(6)(p25), −7, del(13)(q21), −15, −16, +1 | Y (34%) | 64 |
| 19 | AML from MDS | 45, XX, del(5)(q13q33), −20; Monosomy 5, 7, 17 FISH | Y (28%) | 57 |
| 20 | AML from MDS | 46, XY[20] | Y (27%) | 70 |
| 21 | AML from MDS | monosomy 7 FISH Only; Karyotype NL | Y (34%) | 63 |
| 22 | AML from MDS | 46, XX, ?t(2; 17)(q31; q25), del(7)(q32), inc.[cp3] | Y (100%) | 66 |
| 23 | AML from MDS | 46, XY[20] | Y (25%) | 69 |
| 24 | AML from MDS | 47, XX, +8[3]/46, XX[17] | Y (75%) | 79 |
| 25 | AML from MDS | 46, XY[20] | Y (33%) | 78 |
| 26 | RAEB-2 | 46, XX, del(5)(q13q35) [16] | Y (26%) | 67 |
| 27 | RAEB-2 | 46, X, add(X)(q28), −5, del(6)(q13), −7, +8, add(19)(p13) | Y (16%) | 64 |
| 28 | RAEB-2 | 47, XY, +mar?c[20] | Y (20%) | 65 |
| 29 | RAEB-2 | 46, XY[20] | Y (255) | 67 |
| 30 | RAEB-2 | 46, XY, del(20)(q11.2q13.3)[4] | Y (50%) | 73 |
| 31 | RAEB-1 | 46, XY[20] | Y (23%) | 77 |
| 32 | RAEB-1 | 46, X, idic(X)(q13)[12]/47, IDEM, +idic(X)(q13)[3]/45] | Y (33%) | 77 |
| 33 | RAEB-1 | — | Y (20%) | 76 |
| 34 | RCMD | 46, XX, t(3: 3)(q21; q26.3){19}/46, XX{1} | Y (23%) | 64 |
| 35 | RARS | 46, XY[20] | Y (11%) | 76 |
| 36 | RARS | NL | Y (25%) | 57 |
| 37 | RCMD | Not available | Y (18%) | 75 |
| 38 | RCMD | 46, XY, t(7; 17)(q22; p13)[18]/48, idem, +1, −2, −4, −8, −10, −1 | Y (23%) | 70 |
| 39 | RCMD | 46, XY, del(11)(q14q23)[16]/46, idem, del(20)(q11.2q1) | Y (25%) | 74 |
| 40 | RCMD | NL | Y (20%) | 67 |
| 41 | RCMD | FISH: 1p36; del(7q); loss of p53; Karyotype NE | Y (16%) | 76 |
| 42 | AML | NL | N | 49 |
| 43 | AML | NL | N | 71 |
| 44 | AML | NL | N | 49 |
| 45 | AML | complex54-57, X, add(X)(q28), +X, +1, −4, add(4)(p15), del(4)(q21), add(5)(p15), del(5)(q13q33), del(6)(q21q25), del(7)(q22), inv(7)(q22), +8, add(9)(p22), +11x2, del(12)(q12), add(12)(p13), −13, +14x2, −18, +19, +20, +21, +22 | N | 64 |
| 46 | AML | 47, XX, t(2; 7)(q13; q22), t(9; 11)(p22; q23), +19 | N | 60 |
| 47 | AML | 46, XX, del(7)(q11.2), ?del(10)(p11.2) | N | 61 |
| 48 | AML | 46, XX, del(7)(q22q32) | N | 75 |
| 49 | AML | 46, XX, ?t(11; 19)(q23; p13.1) | N | 61 |
| 50 | AML | 46, XX, del(13q)(q12q14), del(20)(q11.2) | N | 60 |
| 51 | AML | 50, XX, +2, ins(3; ?)(q21; ?)x2, del(5)(q23q31), +6, +8, +10, amp(11)(q23), +del(13)(q12q14), −18 | N | 71 |
| 52 | AML | 40-42, XY, dup(1)(p13p22), −3, −4, −5, del(6)(q21q25), −7, t(9; 11)(q13; p13), +11, −13, −16, Add(17)(p13), −22 | N | 64 |
| 53 | AML | Normal Karyotype; FISH del(7q) 4.6% | N | 59 |
| 54 | AML | trisomy c-13 71% | N | 71 |
| 55 | AML | 48, XY, +9, +13; FISH: extra copy of 9 - 40% | N | 79 |
| 56 | AML | 46, XY, del(9)(q13q22) | N | 50 |
| 57 | AML | NL | N | 31 |
| 58 | AML | NL | N | 72 |
| 59 | AML | NE | N | 24 |
| 60 | AML | t(1q32; 4q21) | N | 34 |
| 61 | AML | trisomy(8, 14, 16, 18) | N | 37 |
| 62 | AML | NL | N | 68 |
| 63 | AML | NL | N | 41 |
| 64 | AML | NL | N | 62 |
| 65 | AML from MDS | 47, XY, +8 | N | 73 |
| 66 | AML from MDS | NL | N | 51 |

TABLE 11-continued

β-Catenin Cellular Localization in Patients with MDS, AML, and
AML arising from prior MDS with Associated Cytogenetic Abnormalities

| Patient ID | Diagnosis | Cytogenetics | β-catenin nuclear localization (% Nuclear) | Age (years) |
|---|---|---|---|---|
| 67 | AML from MDS | Karyotype NE; FISH: 5q deletion in 65% | N | 47 |
| 68 | AML from MDS | 51-60, XY, +Y, +1, +2, +2, −2, −4, +5, del(5)(q13q31), +6, +7, del(7)(q22), +8, −9, −10, i(11)(q10), −12, +13, +14, −15, −17, −21, +22 | N | 42 |
| 69 | AML from MDS | NL | N | 74 |
| 70 | AML from MDS | Karyotype NE; FISH: del(7q) in 3% | N | 67 |
| 71 | AML from MDS | Karyotype NE; FISH del(7q) in 7.6% and trisomy 11 in 40% of cells | N | 64 |
| 72 | AML from MDS | NE | N | 65 |
| 73 | AML from MDS | 46, XX, del(11)(q23), der(17)t(3; 17)(p21; p11); FISH: del 7q in 69% and deletion of 11q23 in 7% of interphase cells | N | 67 |
| 74 | AML from MDS | 46, XY[20] | N | 74 |
| 75 | AML from MDS | 46, XY[20] | N | 69 |
| 76 | AML from MDS | 46, XY, del(4)(q21q27), add(5)(q15), −7, −11, +r1, +r2[18] | N | 90 |
| 77 | AML from MDS | 46, XY{20} | N | 70 |
| 78 | AML from MDS | — | N | 76 |
| 79 | RAEB-2 | Karyotype NE; FISH, monosomy of chromosome 7 in 13.33% | N | 36 |
| 80 | RAEB-2 | NL | N | 71 |
| 81 | RAEB-2 | NL | N | 86 |
| 82 | RAEB-2 | 46, XY, add(17)q11.2), add(21)q11.2), add(21)(q22) | N | 77 |
| 83 | RAEB-2 | 45, XY, del(5)(q13q35), der(10)inv(10)(p11.2q22)t (10) | N | 80 |
| 84 | RAEB-2 | 46, XY[20] | N | 63 |
| 85 | RAEB-2 | 46, XY, del(14)(q32){15]/46, XY{5} | N | 62 |
| 86 | RAEB-2 | 45, XX, −7{2}/46, XX, −7, t(12; 18)(p13;q21), +mar{2}/46 | N | 61 |
| 87 | RAEB-2 | 46, Y, del(X)(q24), −7, +8, dup(11)(q13q24.2), add(18) (p | N | 72 |
| 88 | RAEB-2 | 47, XX, +8[6]/46, XX[14] | N | 67 |
| 89 | RAEB-2 | NL | N | 67 |
| 90 | RAEB-2 | Karyotype NE; FISH: 5q deletion in 54% | N | 71 |
| 91 | RAEB-1 | 45, XY, −7[4]/46, IDEM, +MAR[16] | N | 76 |
| 92 | RAEB-1 | 46, XX, del(5)(q13q33)[7]/46, XX[13] | N | 81 |
| 93 | RAEB-1 | 46, XY{20} | N | 73 |
| 94 | RAEB-1 | 47, XY, +8 | N | 68 |
| 95 | RAEB-1 | 45, XY, −7 | N | 60 |
| 96 | RAEB-1 | Del (5q), del(7q), +8, and i(11q) | N | 42 |
| 97 | RAEB-1 | NE | N | 78 |
| 98 | RARS | 47, XY, +8[4]/47, idem, del(13)(q12q14)[12]/46, XY[4] | N | 75 |
| 99 | RCMD | 46, XY[20] | N | 73 |
| 100 | RCMD | 46, XY[20] | N | 68 |
| 101 | RCMD | 45, X, −Y[15]/46, XY[5] | N | 81 |
| 102 | RCMD | 47, XX, +8[6]/46, XX[14] | N | 77 |
| 103 | RCMD | NL | N | 40 |
| 104 | RCMD | NL | N | 70 |
| 105 | RCMD | ND | N | 46 |
| 106 | RCMD | NL | N | 75 |
| 107 | RCUD | 47, XY, der(7)t(1; 7)(q10; p10), +8 | N | 77 |

Example 16—Inhibition of Proliferation and Promotion of Differentiation of Jagged-1 Stimulated HSCs and Primary Leukemic LSKs with Anti-Jagged1 Antibody Materials and Methods Hematopoietic stem cells from healthy controls and from patients with MDS/AML are plated on Jagged-1 coated plates at a concentration of 5 to 100 nM or with osteoblasts from βcat(ex3)$_{osb}$ mice.

The cells are treated with anti-Jagged1 antibody.

Flow cytometry, and clonogenic assays are done as described in Example 1.

Results

HSCs from healthy controls that are plated with Jagged-1 or osteoblasts from βcat(ex3)$_{osb}$ mice develop an increase in the percentage of cells of the myeloid lineage both early (CD33) and mature (CD14, CD11b, Cd15, and Cd66b) suggesting a shift to the differentiation of HSCs to the myeloid lineage. Likewise, HSCs from patients with MDS/AML also show an increase in these cells suggesting a shift of these cells to the myeloid lineage. Differentiation blockade is also shown by the presence of immature myeloid progenitors.

After treatment with the anti-Jagged1 antibody, the defects in the myeloid lineage are reversed in all the cells.

Example 17—Further Evidence that Inhibition of Notch Signaling Reverses Leukemia in βcat(ex3)$_{osb}$ Mice As shown in Example 13, inhibition of Notch signaling in βcat(ex3)$_{osb}$ mice rescues the AML phenotype. Further evidence of this can be shown by treating βcat(ex3)$_{osb}$ mice with an anti-Jagged antibody Materials and Methods βcat(ex3)$_{osb}$ mice as described in Example 1 are used.

The mice are treated as follows (n=10 for each group) for six weeks:
wild-type with vehicle (saline);
βcat(ex3)$_{osb}$ mice with vehicle (saline);
wild-type with 10 mg/kg of anti-Jagged1 antibody;
βcat(ex3)$_{osb}$ mice treated with 10 mg/kg of anti-Jagged1 antibody;
wild-type with 30 mg/kg of anti-Jagged1 antibody;
βcat(ex3)$_{osb}$ mice with 30 mg/kg of anti-Jagged1 antibody;
βcat(ex3)$_{osb}$ mice with DBZ as described in Example 1 and 13 except they are injected with 2 μmol/kg daily.

The following endpoints are analyzed: survival, complete hematopoietic profile in the marrow, leukemia presence in peripheral blood, bone marrow, spleen and liver, potential end organ toxicity, and gene expression profiling of Notch targets Hes1, Hes5, Hey1, and Hey2, and the Hes1 targets, Cebpα and Pu.1.

Hematological measurements, peripheral blood morphology, flow cytometry, PCR, histological analysis, and gene expression profiling are performed as described in Example 1.

Results

As seen in Example 13, DBZ treated βcat(ex3)$_{osb}$ mice have a reversal of anemia, peripheral monocytosis, neutrophilia and lymphocytopenia and the defects in the myeloid lineage, erythroid cells, LSK and LT-HSCs populations in the bone marrow. LSK and the lymphoid-biased progenitors in the bone marrow and the LSK/FcgRII/III subset of myeloid progenitors in the spleen and bone marrow return to normal levels following treatment as well. Myeloperodixase-staining in bone marrow, spleen and liver of DBZ-treated βcat(ex3)$_{osb}$ mice is identical to that of control animals, establishing that myeloid leukemia is inhibited. These samples show no invasion of myeloid cells in DBZ-treated βCat(ex3)$_{osb}$ mice. DBZ-treated mice also have increased survival and a decrease in expression of Notch targets Hes1, Hes5, Hey1, and Hey2, and the Hes1 targets, Cebpα and Pu.1. DBZ treatment has no toxic effect on the intestines.

Consistent with these results, βcat(ex3)$_{osb}$ mice treated with anti-Jagged1 antibody also have a reversal of anemia, peripheral monocytosis, neutrophilia and lymphocytopenia and the defects in the myeloid lineage, erythroid cells, LSK and LT-HSCs populations in the bone marrow. LSK and the lymphoid-biased progenitors in the bone marrow and the LSK/FcgRII/III subset of myeloid progenitors in the spleen and bone marrow return to normal levels following treatment as well. Myeloperodixase-staining in bone marrow, spleen and liver of antibody-treated βcat(ex3)$_{osb}$ mice is identical to that of control animals, establishing that myeloid leukemia is inhibited. The samples show no invasion of myeloid cells in βCat(ex3)$_{osb}$ mice treated with antibody. These antibody-treated mice also have increased survival and a decrease in expression of Notch targets Hes1, Hes5, Hey1, and Hey2, and the Hes1 targets, Cebpα and Pu.1. The anti-Jagged1 antibody treatment has no toxic effect on the intestines.

In contrast, βCat(ex3)$_{osb}$ mice treated with vehicle have no reversal of the leukemic phenotype. These mice have anemia, peripheral monocytosis, neutrophilia and lymphocytopenia and the defects in the myeloid lineage, erythroid cells, LSK and LT-HSCs populations in the bone marrow. Stained bone marrow, spleen and liver show massive invasion of myeloid cells. These mice have reduced survival and increased expression of Notch targets Hes1, Hes5, Hey1, and Hey2, and the Hes1 targets, Cebpα and Pu.1.

REFERENCES

Almeida et al. (2007) *J Bio. Chem.* 282:27298-27305
Arai et al. (2004) *Cell* 118: 149-161
Ausubel et al. (1994) *Current Protocols in Molecular Biology*
Barrett et al. (2005) *Nucleic Acids Res.* 33:D562-D566
Butler et al. (2010) *Cell Stem Cell* 6:251-264
Calvi et al. (2003) *Nature* 425:841-846
Chan et al. (2009) *Nature* 457:490-494
Chen et al. (2009) *Nature* 457:887-891
Dacquin et al. (2002) *Dev. Dyn.* 224:245-54
Day et al. (2005) *Dev. Cell* 8:739-750
Delaney et al. (2010) *Nat. Med.* 16:232-236
Ding et al. (2012) *Nature* 481:457-462
Eghbali-Fatourechi et al. (2005) *N. Engl. J Med.* 352:1959-1966
Essers et al. (2005) *Science* 308:1181-1184
Estrach et al. (2006) *Development* 133:4427-4438
Flores-Figueroa et al. (2005) *Leuk. Res.* 29:215-224
Ghosh-Choudhury et al. (1994) *Crit. Rev. Eukaryot. Gene Expr.* 4:345-355
Glass et al. (2005) *Dev. Cell* 8:751-764
Gowen et al. (1999) *J. Bone Miner. Res.* 14:1654-1663
Graubert and Walter (2011) *Hematology. Am. Soc. Hematol. Educ. Program.* 2011:543-549
Guangyu Wu et al. (2001) *Mol. Cell. Biol.* 21:7403-7415
Harada et al. (1999) *EMBO* 18:5931-42
Heissig et al. (2002) *Cell* 109:625-637
Hill et al. (2005) *Dev. Cell* 8:727-738
Holmen et al. (2005) *J. Biol. Chem.* 280:21162-68
Hurlbut et al. (2007) *Curr. Opin. Cell Biol.* 19:166-175
Hubbell et al. (2002) *Bioinformatics* 18:1585-1592
Iwamoto et al. (2007) *J. Clin. Invest.* 117:1049
Kiel and Morrison (2008) *Nat. Rev Immunol.* 8:290-301
Kiel et al. (2005) *Cell* 121:1109-1121
Kiernan et al. (2006) *PloS Genetics* 2:e4
Kim et al. (2008) *Blood* 112:4628-4638
Klinakis et al. (2011) *Nature* 473:230-233
Kogan et al. (2002) *Blood* 100:238-245
Kornak et al. (2001) *Cell* 104:205-215
Kriegler (1990) *Gene Transfer and Expression: A Laboratory Manual*
Kuhnert et al. (2011) *Vascular Cell* 3:20.
The Leukemia and Lymphoma Society, Facts 2013
Li and Durbin (2010) *Bioinformatics* 26:589-595
Lo et al. (2009) *Nature* 457:92-96
Lowell et al. (1996) *Blood* 87:1780-1792
Manavalan et al. (2012) *J Clin. Endocrinol. Metab* 97:3240-3250.
Mayack and Wagers (2008) *Blood* 112:519-531
Mendez-Ferrer et al. (2010) *Nature* 466:829-834
Mercher et al. (2009) *J Clin. Invest.* 119:852-864
Meyer et al. (2009) *Leukemia* 23:1490-1499
Miyamoto et al. (2011) *J Exp. Med.* 208:2175-2181
Paik et al. (2007) *Cell* 128:309-23
Pajvani et al. (2011) *Nat. Med.* 17:961-967

Parfitt et al. (1987) *J Bone Miner. Res.* 2:595-610.
Parfitt The physiologic and clinical significance of bone histomorphometric data in *Bone histomorphometry: techniques and interpretation* (ed. Recker, R. R.) 143-223 (CRC Press, Boca Raton, 1983)
Raaijmakers et al. (2010) *Nature* 464:852-857
Rached et al. (2010a) *J. Clin. Invest.* 120:357-68
Rached et al. (2010b) *Cell Metab.* 11:147-160
Rankin et al. (2012) *Cell* 149:63-74
Raza and Galili (2012) *Nat. Rev. Cancer* 12:849-859
Real et al. (2009) *Nat. Med.* 15:50-58
Recker. et al. (2011) *Bone* 49:955-964
Robert-Moreno et al. (2008) *EMBO J* 27:1886-1895
Rodda and McMahon (2006) *Development* 133:3231-3244
Rubin et al. (2011) *J Clin. Endocrinol. Metab* 96:176-186.
Sambrook et al. (1989) *Molecular Cloning, A Laboratory Manual*
Schaniel et al (2011) *Blood* 118:2420-2429
Shiozawa et al. (2011) *J Clin. Invest* 121:1298-1312
Simon et al. *Class Comparison in Design and Analysis of DNA Microarray Investigations* (ed. K. Dietz, M.G.K-.K.J.S.A.T.) 65-94 (Springer, N.Y., 2003).
Smyth (2004) *Stat. Appl. Genet. Mol. Biol* 3, Article3
Soriano et al. (1991) *Cell* 64:693-702
Sternberg et al. (2005) *Blood* 106:2982-2991
Sugiyama et al. (2006) *Immunity* 25:977-988.
Sykes et al. (2011) *Cell* 146:697-708
Taichman and Emerson (1994) *J. Exp. Med.* 179:1677-1682
Taichman et al. (1996) *Blood* 87:518-524
The Cancer Genome Atlas Research Network Genomic and Epigenomic Landscapes of Adult De novo Acute Myeloid Leukemia (2013) *N. Engl. J Med.* 368:2059-2074
Tiacci et al. (2011) *N Engl. J Med.* 364:2305-2315
Van de Loosdrecht et al. (2008) *Blood* 111:1067-1077
Van Es et al. (2005) *Nature* 435:959
Visnjic et al. (2004) *Blood* 103:3258-3264
Walkley et al. (2007) *Cell* 129:1097-1110
Wei et al. (2009) *Proc. Natl. Acad. Sci. USA* 106:12974-12979
Winkler et al. (2012) *Nat. Med.* 18:1651-1657
Wu et al. (2008) *Proc. Natl. Acad. Sci. USA* 105:16976-16981
Zhang et al. (2003) *Nature* 425:836-841
Zhu et al. (2007) *Blood* 109:3706-3712
Zuniga-Pflucker (2004) *Nat. Rev. Immunol.* 4:67-72

The invention claimed is:

1. A method of treating and/or preventing acute myeloid leukemia (AML) and/or myelodysplastic syndrome (MDS), comprising administering to a subject in need thereof a therapeutically effective amount of an anti-Jagged-1 antibody.

2. The method of claim 1, wherein the subject is a mammal.

3. The method of claim 1, wherein the subject is a human.

4. The method of claim 1, wherein the anti-Jagged-1 antibody inhibits the activation, expression and/or activity of Notch ligands in osteoblasts.

* * * * *